(12) United States Patent
Lee et al.

(10) Patent No.: US 9,118,021 B2
(45) Date of Patent: *Aug. 25, 2015

(54) HETEROCYCLIC COMPOUND AND ORGANIC LIGHT-EMITTING DEVICE INCLUDING THE SAME

(71) Applicant: Samsung Display Co., Ltd., Yongin (KR)

(72) Inventors: Sun-Young Lee, Yongin (KR); Yoon-Hyun Kwak, Yongin (KR); Bum-Woo Park, Yongin (KR); Jong-Won Choi, Yongin (KR); Wha-Il Choi, Yongin (KR); So-Yeon Kim, Yongin (KR); Ji-Youn Lee, Yongin (KR); Bo-Ra Lee, Yongin (KR)

(73) Assignee: Samsung Display Co., Ltd., Gihueng-Gu, Yongin, Gyeonggi-Do (KR)

( * ) Notice: Subject to any disclaimer, the term of this patent is extended or adjusted under 35 U.S.C. 154(b) by 124 days.

This patent is subject to a terminal disclaimer.

(21) Appl. No.: 13/690,600

(22) Filed: Nov. 30, 2012

(65) Prior Publication Data
US 2014/0103300 A1    Apr. 17, 2014

(30) Foreign Application Priority Data
Jul. 26, 2012  (KR) .......................... 10-2012-0081965

(51) Int. Cl.
| H01L 51/54 | (2006.01) |
|---|---|
| C09K 11/06 | (2006.01) |
| H01L 51/00 | (2006.01) |
| C07D 491/04 | (2006.01) |
| C07D 493/04 | (2006.01) |
| C07D 495/04 | (2006.01) |
| C07D 491/153 | (2006.01) |
| C07D 495/14 | (2006.01) |
| H05B 33/14 | (2006.01) |
| H01L 51/50 | (2006.01) |

(52) U.S. Cl.
CPC .......... *H01L 51/0061* (2013.01); *C07D 491/04* (2013.01); *C07D 491/153* (2013.01); *C07D 493/04* (2013.01); *C07D 495/04* (2013.01); *C07D 495/14* (2013.01); *C09K 11/06* (2013.01); *H01L 51/0071* (2013.01); *H01L 51/0072* (2013.01); *H01L 51/0073* (2013.01); *H01L 51/0074* (2013.01); *H05B 33/14* (2013.01); *C09K 2211/1007* (2013.01); *C09K 2211/1011* (2013.01); *C09K 2211/1022* (2013.01); *C09K 2211/1029* (2013.01); *C09K 2211/1033* (2013.01); *C09K 2211/1037* (2013.01); *C09K 2211/1044* (2013.01); *C09K 2211/1088* (2013.01); *C09K 2211/1092* (2013.01); *H01L 51/506* (2013.01); *H01L 51/5012* (2013.01); *H01L 51/5016* (2013.01); *H01L 51/5072* (2013.01)

(58) Field of Classification Search
None
See application file for complete search history.

(56) References Cited

U.S. PATENT DOCUMENTS

| 5,635,308 | A | 6/1997 | Inoue et al. |
|---|---|---|---|
| 5,645,948 | A | 7/1997 | Shi et al. |
| 5,972,247 | A | 10/1999 | Shi et al. |
| 6,465,115 | B2 | 10/2002 | Shi et al. |
| 6,596,415 | B2 | 7/2003 | Shi et al. |
| 2009/0066235 | A1 | 3/2009 | Yabunouchi et al. |
| 2011/0031484 | A1* | 2/2011 | Lee et al. .......................... 257/40 |
| 2011/0156016 | A1 | 6/2011 | Kawamura et al. |
| 2011/0210318 | A1 | 9/2011 | Bae et al. |
| 2011/0288292 | A1 | 11/2011 | Parham et al. |

FOREIGN PATENT DOCUMENTS

| JP | 08012600 | 1/1996 |
|---|---|---|
| JP | 2000003782 | 1/2000 |
| KR | 1020100003624 | 1/2010 |
| KR | 1020100023783 | 3/2010 |
| KR | 1020100038193 | 4/2010 |
| KR | 1020110119726 | 11/2011 |

OTHER PUBLICATIONS

Tang et al., Organic electroluminescent diodes, Appl. Phys. Lett. (1987) 51, pp. 913-915.
Yamaguchi et al., Diphenylamino-Substituted 2,5-Diarylsiloles for Single-Layer Organic Electroluminescent Devices, Chem. Lett. (2001) pp. 98-99.
Sakamoto et al., Synthesis, Characterization, and Electron-Transport Property of Perfluorinated Phenylene Dendrimers, J. Am. Chem. Soc. (2000) 122, pp. 1832-1833.
Adachi et al., Confinement of charge carriers and molecular excitons within 5-nm-thick emitter layer in organic electroluminescent devices with a double heterostructure, Appl. Phys. Lett. (1990) 57, pp. 531-533.

* cited by examiner

*Primary Examiner* — Andrew K Bohaty
(74) *Attorney, Agent, or Firm* — Robert E. Bushnell, Esq.

(57) ABSTRACT

Novel heterocyclic compounds that impart improved luminescence efficiency characteristics such as low voltage, high luminance and long lifetime to organic light-emitting devices are described. Synthetic methods for the subject heterocyclic compounds are described. Methods for the construction of an organic light-emitting device comprising at least one of the subject heterocyclic compounds and comprising various hole transport layers, various electron transport layers and an emission layer are disclosed. The emission layer can comprise red, green, blue and white emission layers; one of said emission layers can comprise a phosphorescent compound. In certain embodiments, the heterocyclic compounds are useful as either fluorescent dopants or as phosphorescent hosts in the emission layer.

20 Claims, 1 Drawing Sheet

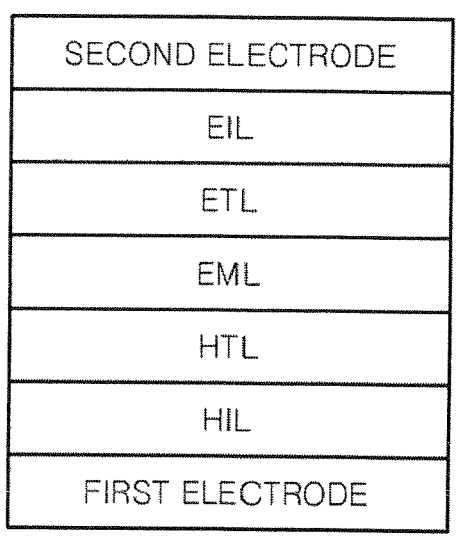

HETEROCYCLIC COMPOUND AND ORGANIC LIGHT-EMITTING DEVICE INCLUDING THE SAME

CLAIM OF PRIORITY

This application makes reference to, incorporates the same herein, and claims all benefits accruing under 35 U.S.C. §119 from an application for NOVEL HETEROCYCLIC COMPOUND AND ORGANIC LIGHT-EMITTING DEVICE INCLUDING THE SAME earlier filed in the Korean Intellectual Property Office on 26 Jul. 2012 and there duly assigned Serial No. 10-2012-0081965.

BACKGROUND OF THE INVENTION

1. Field of the Invention

The present invention relates to a novel heterocyclic compound and an organic light-emitting device including the same.

2. Description of the Related Art

Organic light-emitting devices (OLEDs), which are self-emitting devices, have advantages such as wide viewing angles, excellent contrast, quick response, high brightness, and excellent driving voltage characteristics and can provide multicolored images.

A typical OLED has a layer structure including a substrate, an anode, a hole transport layer (HTL), an emission layer (EML), an electron transport layer (ETL) and a cathode, the layers being sequentially stacked on the substrate. In this regard, the HTL, the EML and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

A major factor affecting luminescent efficiency of an OLED is the luminescent material used. Light-emitting materials used in the prior art have typically been fluorescent materials or phosphorescent materials. Prior art light-emitting materials are not satisfactory in terms of efficiency, driving voltage, and lifetime, and thus there has been a demand for development of a more stable material with improved performance.

SUMMARY OF THE INVENTION

The present invention provides novel heterocyclic compounds with improved luminescence efficiency characteristics and a high efficiency, low voltage, high luminance and long lifetime organic light-emitting device including at least one of the presently disclosed novel heterocyclic compounds. The novel heterocyclic compounds of the present invention have improved electrical characteristics, good charge transport capabilities, improved emission capability and glass transition temperature ($T_g$) high enough to prevent crystallization. The novel heterocyclic compounds are suitable as charge transporting materials for fluorescent or phosphorescent devices of any color, or as red, green, blue, or white light-emitting materials with higher emission efficiency, longer lifetime and appropriate color coordinates, as compared with existing materials.

According to an aspect of the present invention, there is provided a heterocyclic compound represented by one of Formulae 1 to 4 below:

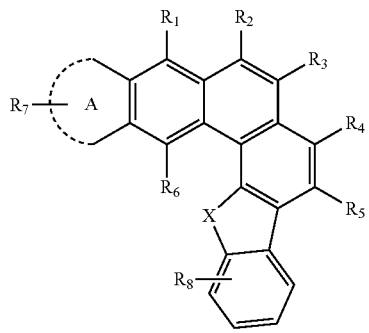

Formula 1

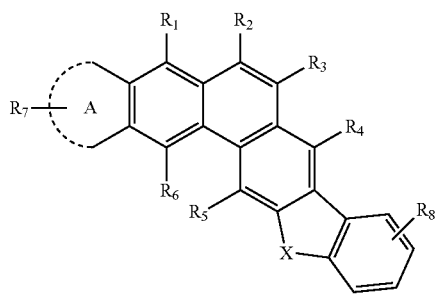

Formula 2

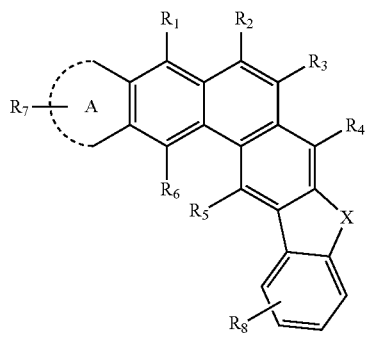

Formula 3

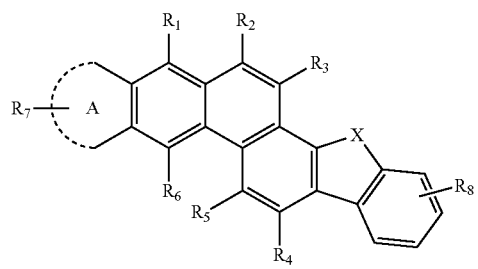

Formula 4

$R_1$ to $R_8$ in Formula 1 being each independently selected from a hydrogen atom, a deuterium atom, a halogen atom, a cyano group, a substituted or unsubstituted $C_1$-$C_{60}$ alkyl group, a substituted or unsubstituted $C_5$-$C_{60}$ aryl group, a substituted or unsubstituted $C_3$-$C_{60}$ heteroaryl group, and a substituted or unsubstituted $C_6$-$C_{60}$ condensed polycyclic group;

X is —O—, —S—, or —NR$_{20}$—; and R$_{20}$ is selected from a substituted or unsubstituted $C_1$-$C_{30}$ alkyl group, or a substituted or unsubstituted $C_5$-$C_{30}$ aryl group; and A is a moiety selected from a substituted or unsubstituted furan group, a substituted or unsubstituted thiophene group, a substituted or unsubstituted pyrrole group, a substituted or unsubstituted benzofuran group, a substituted or unsubstituted benzothiophene group, or a substituted or unsubstituted benzopyrrole group, said moiety being fused to the skeleton of one of Formulae 1 to 4.

According to another aspect of the present invention, there is provided an organic light-emitting device including: a first electrode; a second electrode; and an organic layer between the first electrode and the second electrode, the organic layer comprising at least one of the above-described heterocyclic compounds.

According to another aspect of the present invention, there is provided a flat panel display device comprising the above-described organic light-emitting device, the first electrode of the organic light-emitting device being electrically connected to a source electrode of a thin-film transistor or a drain electrode of a thin-film transistor.

BRIEF DESCRIPTION OF THE DRAWING

The above and other features and advantages of the present invention will become more apparent by describing in detail exemplary embodiments thereof with reference to the attached drawing in which:

FIG. 1 schematically illustrates the structure of an organic light-emitting device according to an embodiment of the present invention.

DETAILED DESCRIPTION OF THE INVENTION

As used herein, the term "and/or" includes any and all combinations of one or more of the associated listed items. Expressions such as "at least one of", when preceding a list of elements, modify the entire list of elements and do not modify the individual elements of the list.

According to an aspect of the present invention, there are provided heterocyclic compounds represented by Formulae 1 to 4 below:

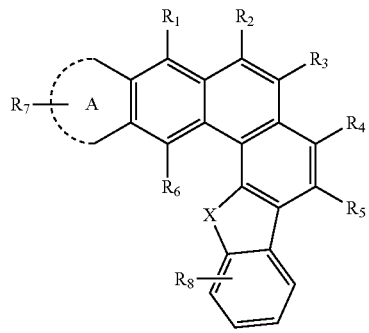

Formula 1

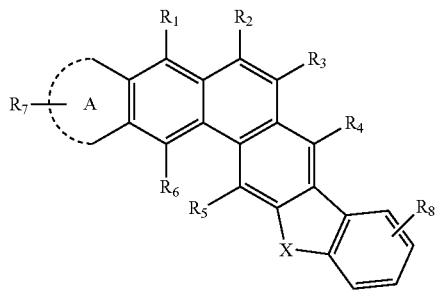

Formula 2

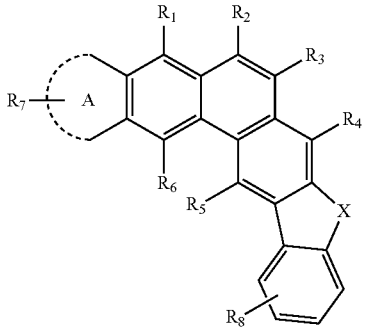

Formula 3

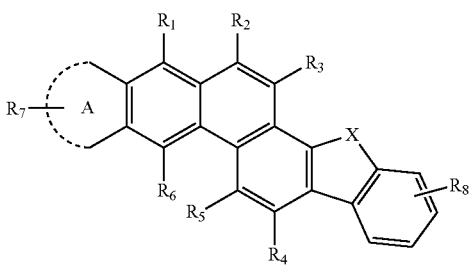

Formula 4

$R_1$ to $R_8$ in Formula 1 are each independently selected from a hydrogen atom, a deuterium atom, a halogen atom, a cyano group, a substituted or unsubstituted $C_1$-$C_{60}$ alkyl group, a substituted or unsubstituted $C_5$-$C_{60}$ aryl group, a substituted or unsubstituted $C_3$-$C_{60}$ heteroaryl group, and a substituted or unsubstituted $C_6$-$C_{60}$ condensed polycyclic group;

X is —O—, —S—, or —NR$_{20}$—; and R$_{20}$ is selected from a substituted or unsubstituted $C_1$-$C_{30}$ alkyl group and a substituted or unsubstituted $C_5$-$C_{30}$ aryl group; and A is a moiety selected from a substituted or unsubstituted furan group, a substituted or unsubstituted thiophene group, a substituted or unsubstituted pyrrole group, a substituted or unsubstituted benzofuran group, a substituted or unsubstituted benzothiophene group and a substituted or unsubstituted benzopyrrole group, said moiety being fused to the skeleton of one of Formulae 1 to 4.

In some embodiments the heterocyclic compounds of Formulae 1 to 4 may be used as light-emitting materials and/or a hole-transport material or a hole-injection material. The heterocyclic compounds of Formula 1, each having at least one heterocyclic group in the molecule thereof, have high glass transition temperatures (Tg) or high melting points due to inclusion of the heterocyclic groups. Thus, the heterocyclic compounds of the present invention have high heat resistance against Joule heating generated in organic layers, between organic layers, or between an organic layer and a metal electrode when light emission occurs, and have high durability in high temperature environments. An organic light-emitting device manufactured using one or more of the heterocyclic compounds of Formulae 1 to 4 described above can have high durability when stored or operated.

Substituents in the heterocyclic compounds of Formulae 1 to 4 will now be described in detail.

In some embodiments, $R_1$, $R_4$, $R_6$, and $R_8$ in Formulae 1 to 4 are each independently a hydrogen atom or a deuterium atom.

In some embodiments, A in Formulae 1 to 4 is a moiety selected from a substituted or unsubstituted furan group, a substituted or unsubstituted thiophene group, a substituted or unsubstituted pyrrole group, a substituted or unsubstituted benzofuran group, a substituted or unsubstituted benzothiophene group, and a substituted or unsubstituted benzopyrrole group said moiety being fused to the skeleton of Formula 1, 2, 3, or 4 at positions 2 and 3 in Formula 11 below, or positions 2 and 3 in Formula 12 (Substituents in Formulae 11 and 12 are omitted):

Formula 11

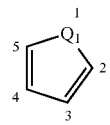

Formula 12

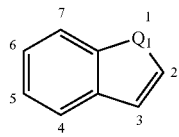

$Q_1$ being —O—, —$NR_{30}$—, or —S— in Formulae 11 and 12, $R_{30}$ being selected from a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, and a substituted or unsubstituted $C_6$-$C_{20}$ condensed polycyclic group.

Formulae 11 and 12 above are only for illustrating a position at which A in Formulae 1 to 4 is fused to the skeleton of Formula 1, 2, 3 or 4, and no substituent is represented in Formulae 11 and 12 though the corresponding positions of Formulae 1, 2, 3 or 4 can be substituted.

In some embodiments, $R_2$ and $R_3$ in Formulae 1 to 4 can be each independently selected from one of the groups represented by Formulae 2a to 2f below.

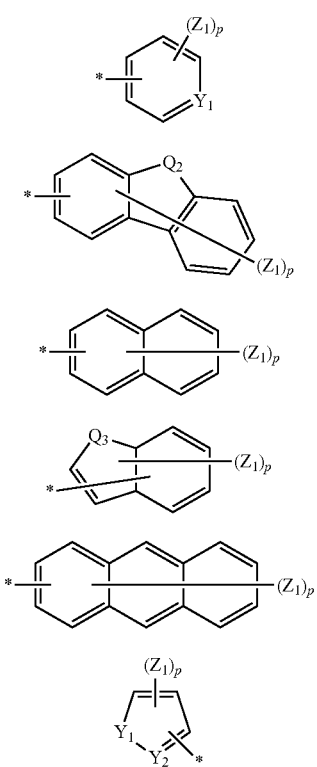

In Formulae 2a to 2f, $Q_2$ is a linking group selected from —$N(R_{30})$—, —$CR_{31}R_{32}$—, —S—, and —O—;

$Q_3$ is a linking group selected from —S— and —O—;

$Y_1$ and $Y_2$ are each independently selected from —N=, —$N(R_{30})$—, and —CH=;

$Z_1$, $R_{30}$, $R_{31}$, and $R_{32}$ are each independently selected from a hydrogen atom, a deuterium atom, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_5$-$C_{20}$ aryl group or a $C_3$-$C_{20}$ heteroaryl group, a halogen group, a cyano group, a nitro group, a hydroxyl group, and a carboxy group;

p is an integer from 1 to 9; and

* indicates a binding site.

Hereinafter, substituents described with reference to the formulae will now be described in detail. In this regard, the numbers of carbons in substituents are presented only for illustrative purposes and do not limit the characteristics of the substituents.

The unsubstituted $C_1$-$C_{60}$ alkyl group used herein can be linear or branched. Examples of the alkyl group can include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group can be substituted with a deuterium atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group comprises an unsaturated linear or branched hydrocarbon chain having at least one carbon-carbon double bond in the center or at a terminal of the chain. Examples of the alkenyl group are an ethenyl group, a propenyl group, a butenyl group, and the like. At least one hydrogen atom in the unsubstituted alkenyl group may be substituted with a substituent described above in conjunction with the alkyl group.

The unsubstituted $C_2$-$C_{60}$ alkynyl group comprises a linear or branched hydrocarbon chain having at least one carbon-carbon triple bond in the center or at a terminal of the chain. Non-limiting examples of the unsubstituted $C_2$-$C_{20}$ alkynyl group are acetylene, propylene, phenylacetylene, naphthylacetylene, isopropylacetylene, t-butylacetylene, and diphenylacetylene. At least one hydrogen atom in the alkynyl group can be substituted with a substituent described above in conjunction with the alkyl group.

The unsubstituted $C_3$-$C_{60}$ cycloalkyl group comprises a $C_3$-$C_{60}$ cyclic alkyl group wherein at least one hydrogen atom in the cycloalkyl group can be substituted with a substituent described above in conjunction with the $C_1$-$C_{60}$ alkyl group.

The unsubstituted $C_1$-$C_{60}$ alkoxy group comprises a group having a structure of —OA wherein A is an unsubstituted $C_1$-$C_{60}$ alkyl group as described above. Non-limiting examples of the unsubstituted $C_1$-$C_{60}$ alkoxy group can be a methoxy group, an ethoxy group, a propoxy group, an isopropyloxy group, a butoxy group, and a pentoxy group. At least one hydrogen atom of the alkoxy group can be substituted with a substituent such as those described above in conjunction with the alkyl group.

The unsubstituted $C_5$-$C_{60}$ aryl group comprises a carbocyclic aromatic system containing at least one ring. At least two rings can be fused to each other or linked to each other by a single bond. The term 'aryl' refers to an aromatic system, such as phenyl, naphthyl, or anthracenyl. At least one hydrogen atom in the aryl group can be substituted with a substituent described above in conjunction with the unsubstituted $C_1$-$C_{60}$ alkyl group.

Non-limiting examples of the substituted or unsubstituted $C_5$-$C_{60}$ aryl group are a phenyl group, a $C_1$-$C_{10}$ alkylphenyl group (for example, ethylphenyl group), a halophenyl group (for example, ortho-, meta-, and para-fluorophenyl group, dichlorophenyl group), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, an ortho-, meta-, and para-tolyl group, an ortho-, meta-, and para-cumenyl group, a mesityl group, a phenoxyphenyl group, an (α,α-dimethylbenzene)phenyl group, a (N,N-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinonyl group, a methylanthryl group, a phenanthryl group, a triphenylene group, a pyrenyl group, a chrycenyl group, an ethyl-chrycenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_3$-$C_{60}$ heteroaryl group used herein includes one, two or three hetero atoms selected from N, O, P and S. At least two rings can be fused to each other or linked to each other by a single bond. Non-limiting examples of the unsubstituted $C_4$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group can be substituted with a substituent described above in conjunction with the unsubstituted $C_1$-$C_{60}$ alkyl group.

The unsubstituted $C_5$-$C_{60}$ aryloxy group is a group represented by —$OA_1$ wherein $A_1$ can be a $C_5$-$C_{60}$ aryl group. An example of the aryloxy group is a phenoxy group. At least one hydrogen atom in the aryloxy group can be substituted with a substituent described above in conjunction with the unsubstituted $C_1$-$C_{60}$ alkyl group.

The unsubstituted $C_5$-$C_{60}$ arylthio group is a group represented by —$OA_1$ wherein $A_1$ may be a $C_5$-$C_{60}$ aryl group. Non-limiting examples of the arylthio group are a benzenethio group and a naphthylthio group. At least one hydrogen atom in the arylthio group may be substituted with a substituent described above in conjunction with the unsubstituted $C_1$-$C_{60}$ alkyl group.

The unsubstituted $C_6$-$C_{60}$ condensed polycyclic group used herein refers to a substituent including at least two rings, the substituent comprising at least one aromatic ring and/or at least one non-aromatic ring that are fused to each other, or refers to a substituent having an unsaturated group in a ring that may not form a conjugate structure. The unsubstituted $C_6$-$C_{60}$ condensed polycyclic group are distinct from an aryl group or a heteroaryl group in terms of being non-aromatic.

Representative compounds forming core structures of the heterocyclic compounds of Formulae 1 to 4 are presented in the following table.

| Core Structure | | |
|---|---|---|
| 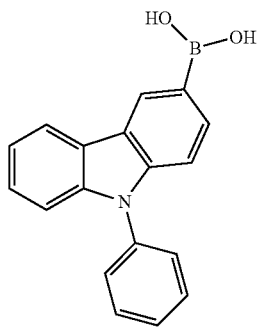 [SMILES: OB(O)c1ccc2c(c1)c1ccccc1n2-c1ccccc1] 1 | 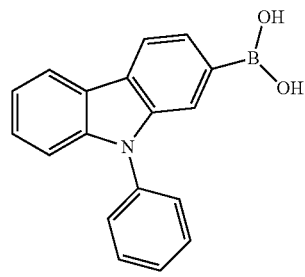 [SMILES: OB(O)c1ccc2c3ccccc3n(-c3ccccc3)c2c1] 2 | |
| 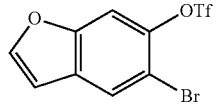 10 | 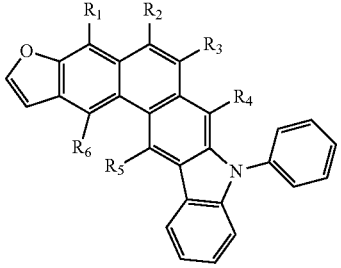 11 | 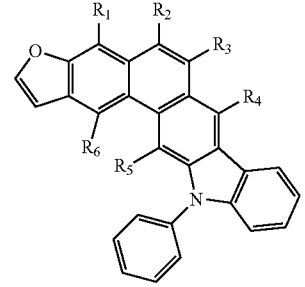 12 |

-continued
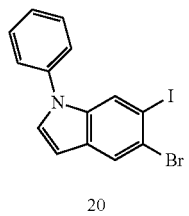
20
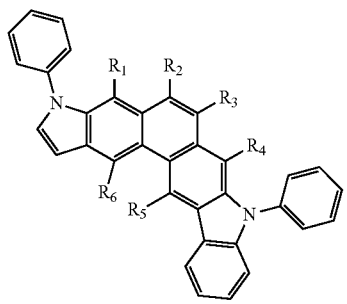
21
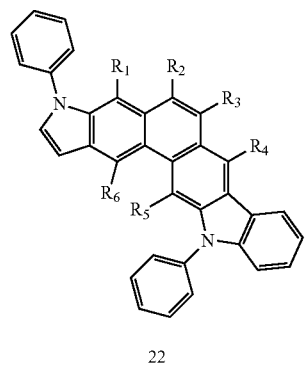
22
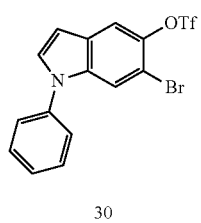
30
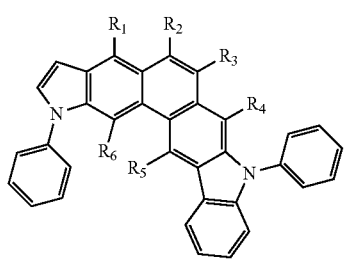
31
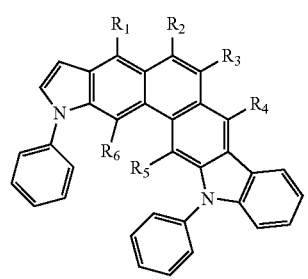
32
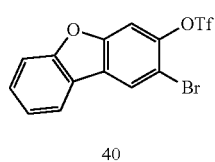
40
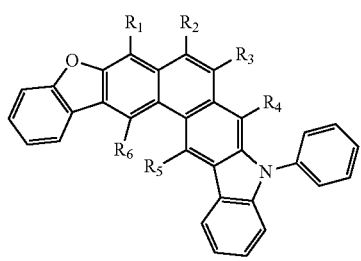
41
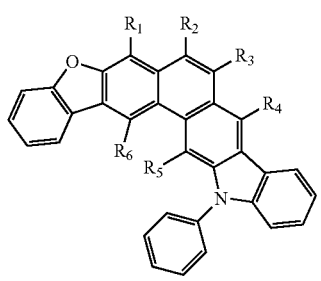
42
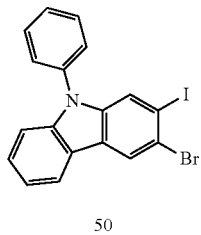
50
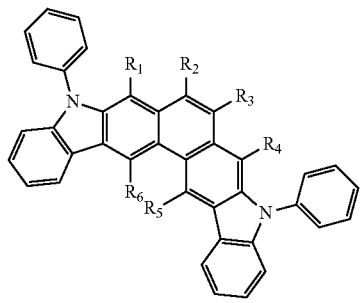
51
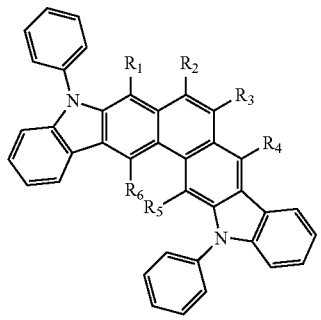
52

-continued
| | | |
|---|---|---|
| 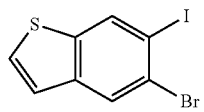 [SMILES: Brc1cc2ccsc2cc1I]<br>60 | 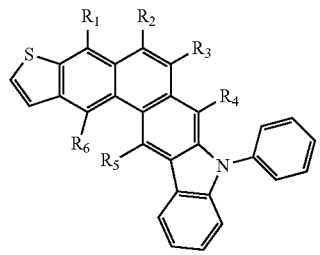<br>61 | 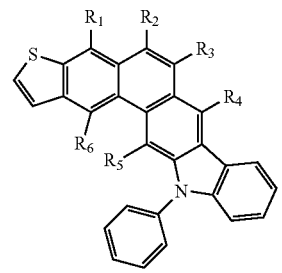<br>62 |
| 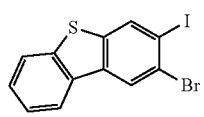<br>70 | 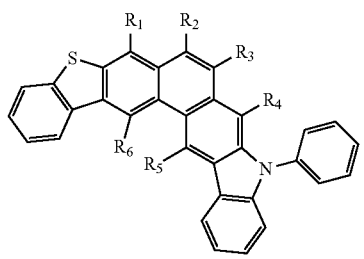<br>71 | 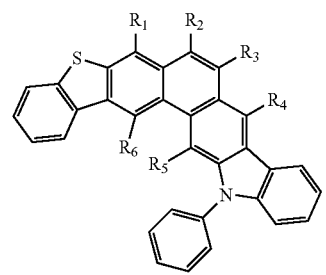<br>72 |
| Core Structure | 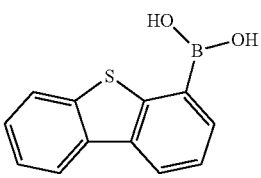 [SMILES: OB(O)c1cccc2c1sc1ccccc12]<br>3 | 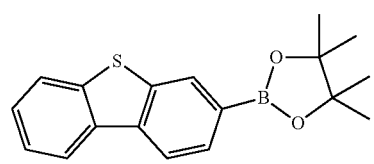 [SMILES: CC1(C)OB(c2ccc3c(c2)sc2ccccc23)OC1(C)C]<br>4 |
| 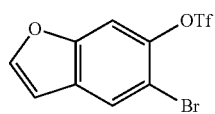 [SMILES: O=S(=O)(Oc1cc2occc2cc1Br)C(F)(F)F]<br>10 | 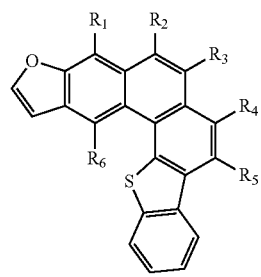<br>13 | 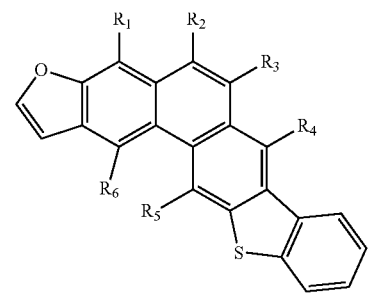<br>14 |
| 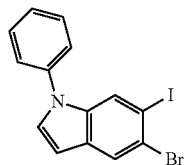 [SMILES: Brc1cc2ccn(-c3ccccc3)c2cc1I]<br>20 | 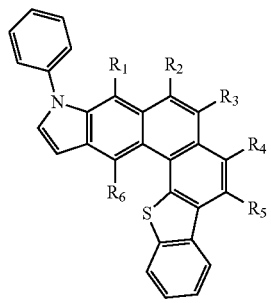<br>23 | 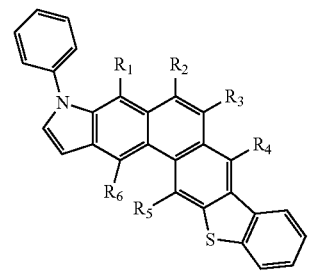<br>24 |

-continued
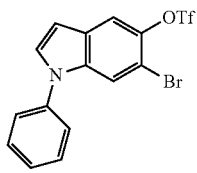 [SMILES: O=S(=O)(Oc1cc2ccn(-c3ccccc3)c2cc1Br)C(F)(F)F]
30
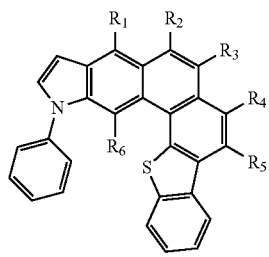
33
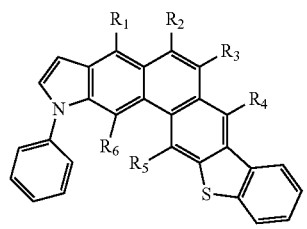
34
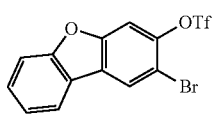 [SMILES: O=S(=O)(Oc1cc2oc3ccccc3c2cc1Br)C(F)(F)F]
40
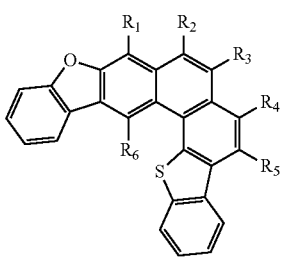
43
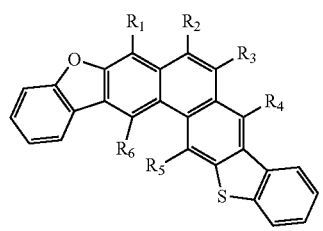
44
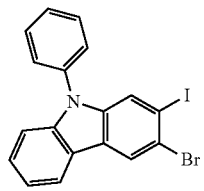 [SMILES: Brc1cc2c3ccccc3n(-c3ccccc3)c2cc1I]
50
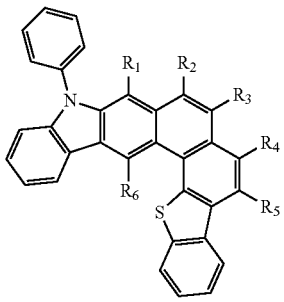
53
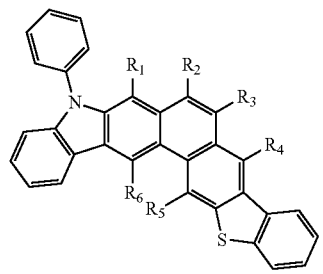
54
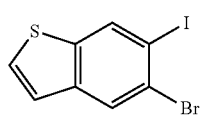 [SMILES: Brc1cc2ccsc2cc1I]
60
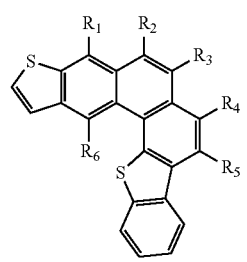
63
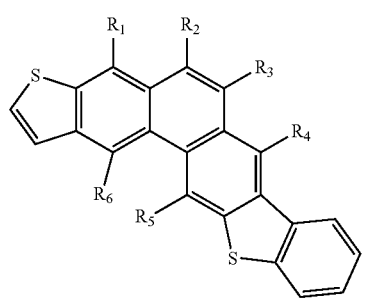
64
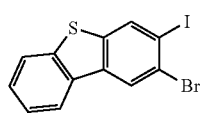 [SMILES: Brc1cc2c(cc1I)sc1ccccc12]
70
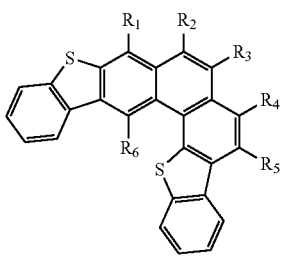
73
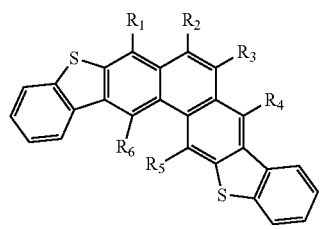
74

-continued
| Core Structure | 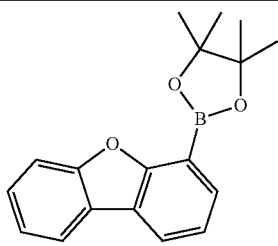 5 | 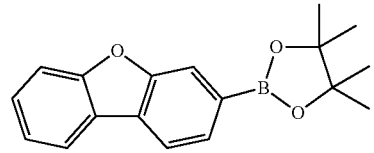 [SMILES: CC1(C)OB(c2ccc3c(c2)oc2ccccc23)OC1(C)C] 6 |
|---|---|---|
| 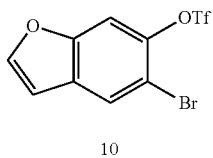 10 | 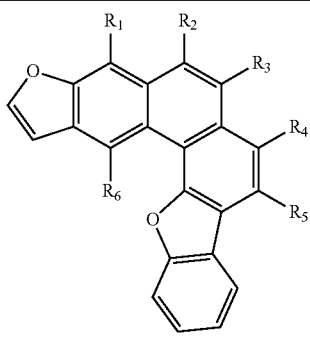 15 | 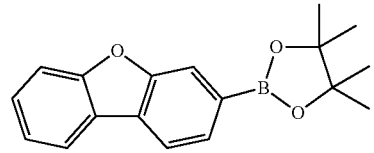 [SMILES: CC1(C)OB(c2ccc3c(c2)oc2ccccc23)OC1(C)C] 16 |
| 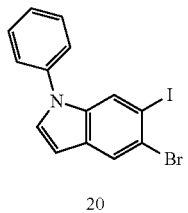 20 | 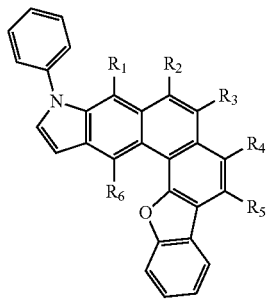 25 | 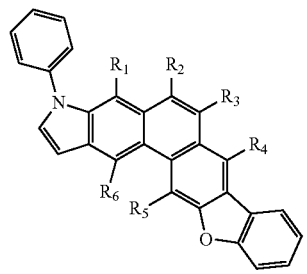 26 |
| 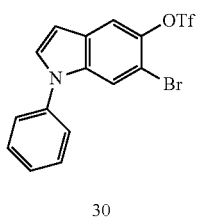 30 | 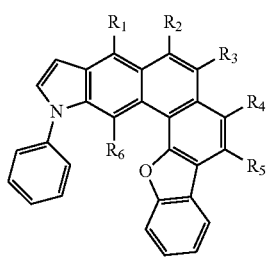 35 | 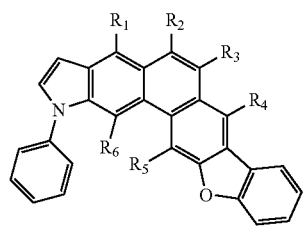 36 |
| 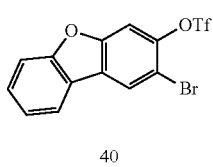 40 | 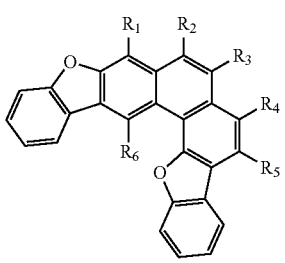 45 | 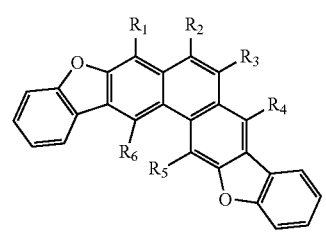 46 |

-continued
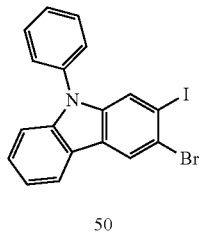
50
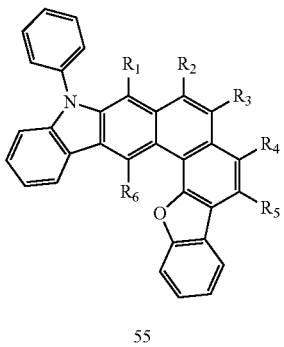
55
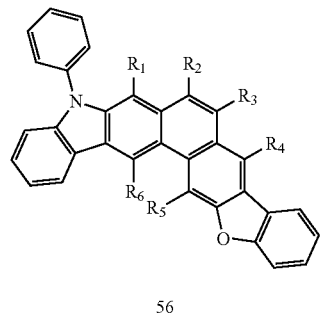
56
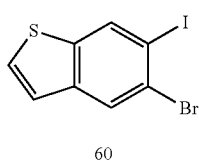
60
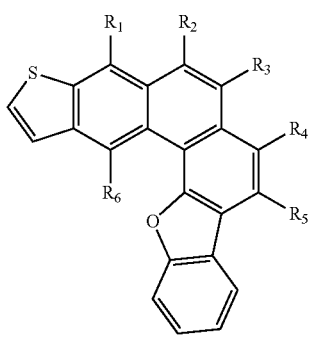
65
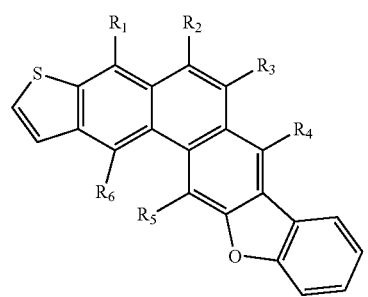
66
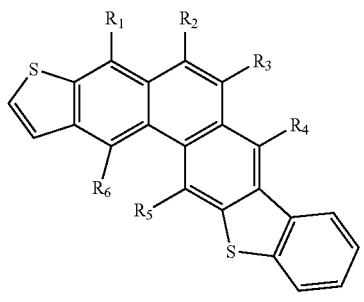
70
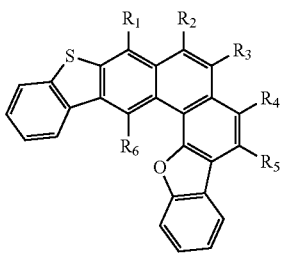
75
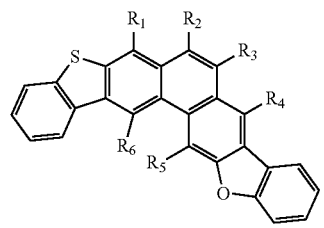
76
Non-limiting examples of the heterocyclic compounds represented by Formulae 1 to 4 are compounds represented by the following Formulae.
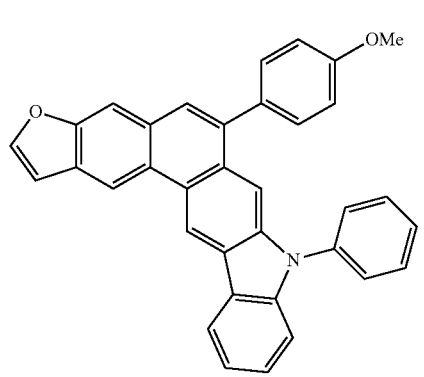
11-A
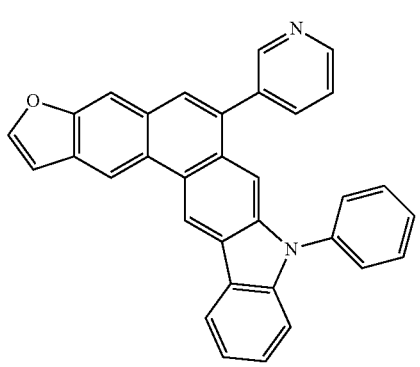
11-B 11-C
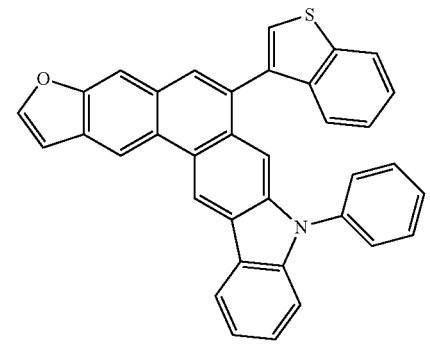
11-D
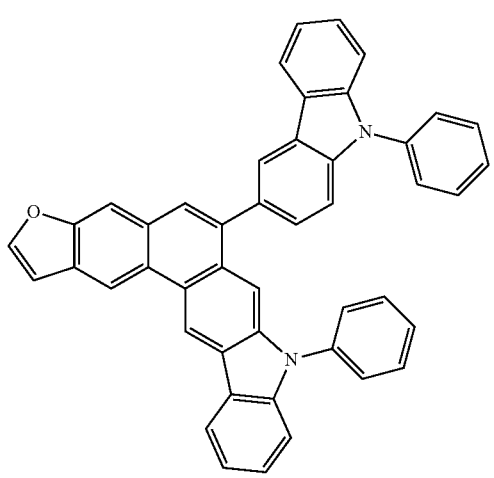
11-E
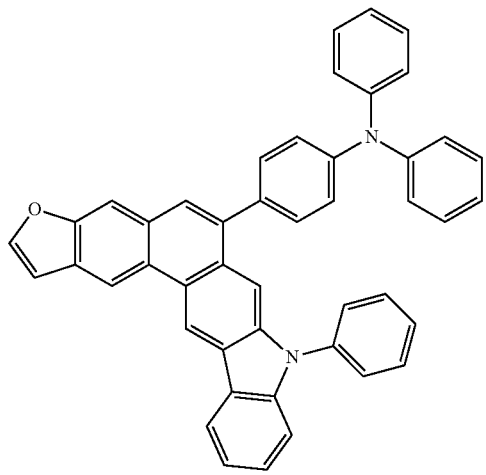
11-F
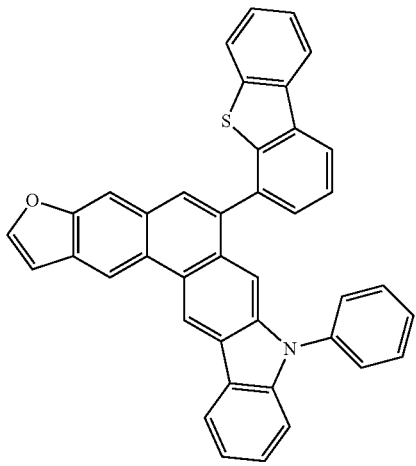
11-G
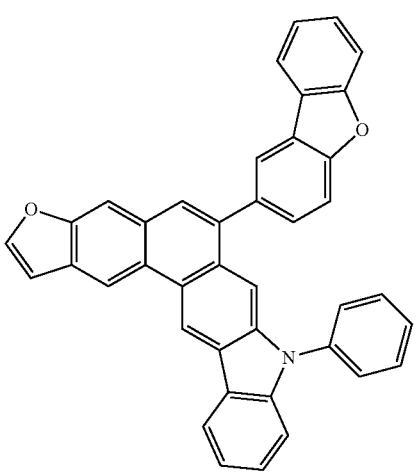
11-H
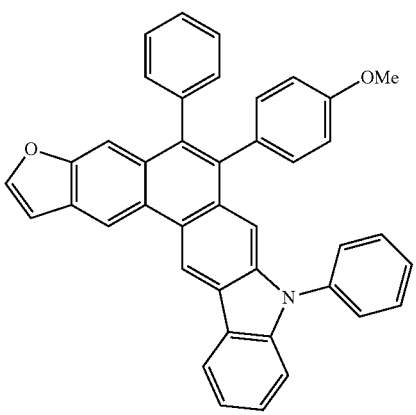

-continued
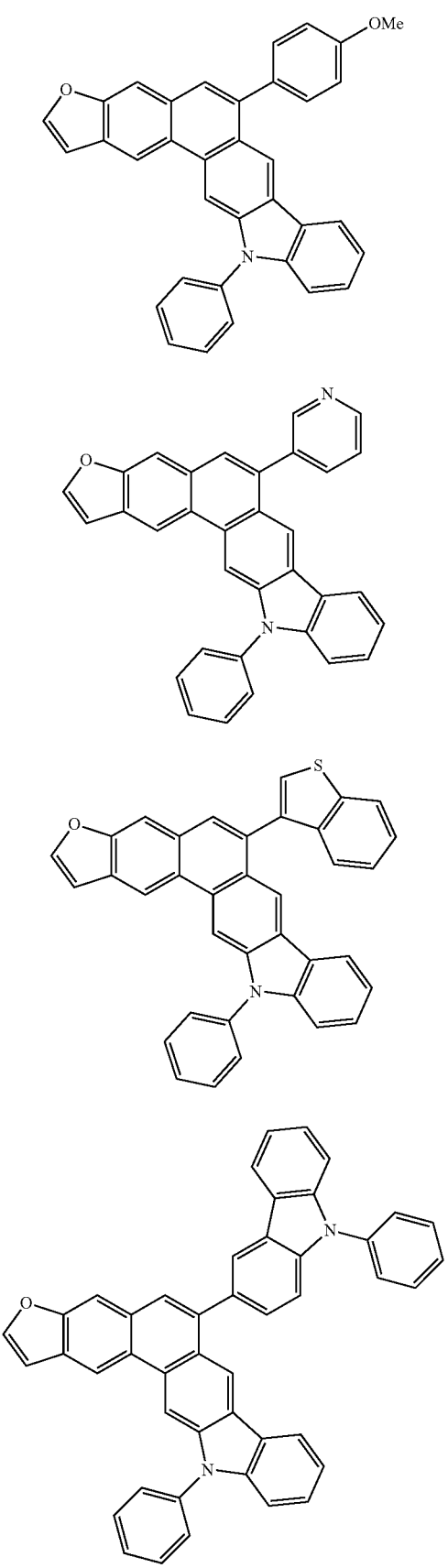
12-A
12-B
12-C
12-D
-continued
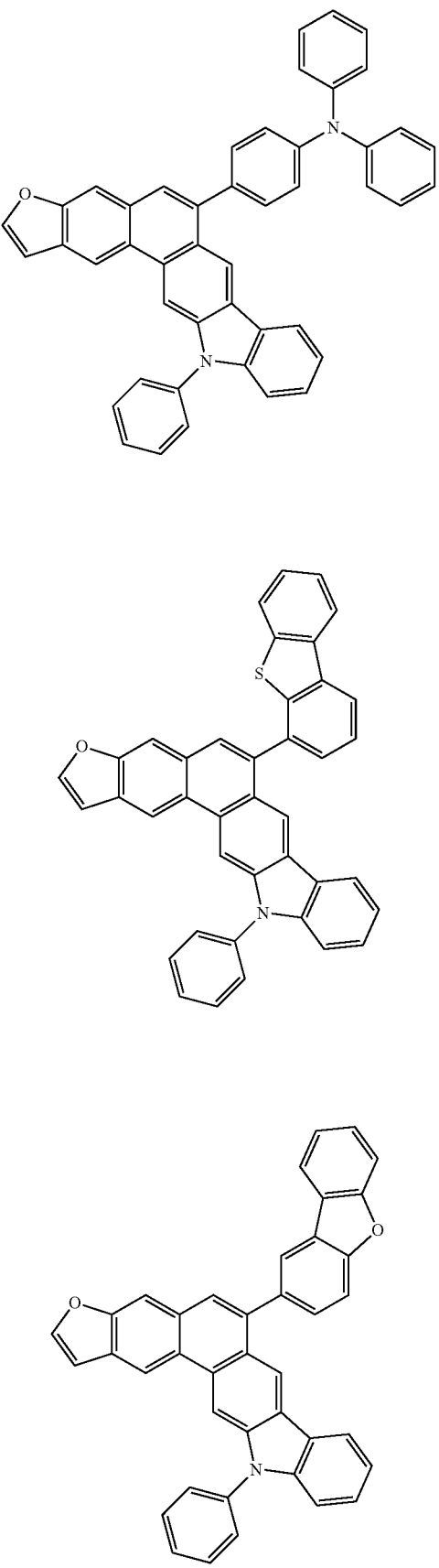
12-E
12-F
12-G

12-H
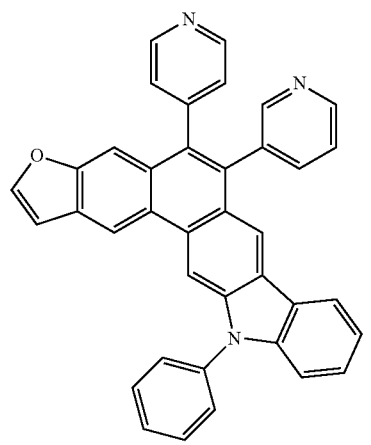
13-A
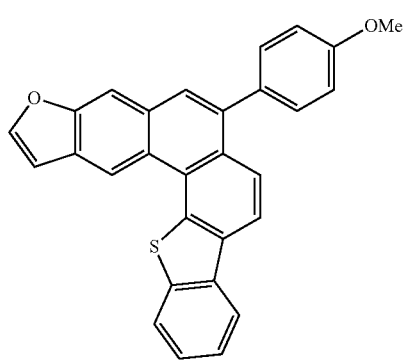
13-B
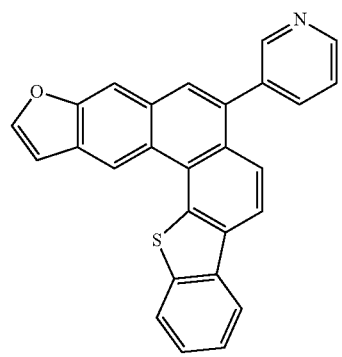
13-C
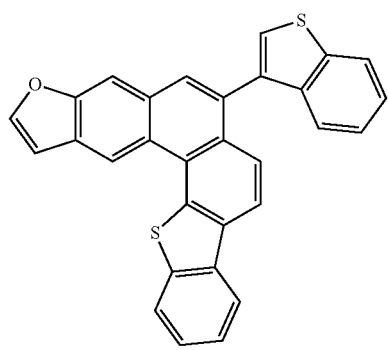
13-D
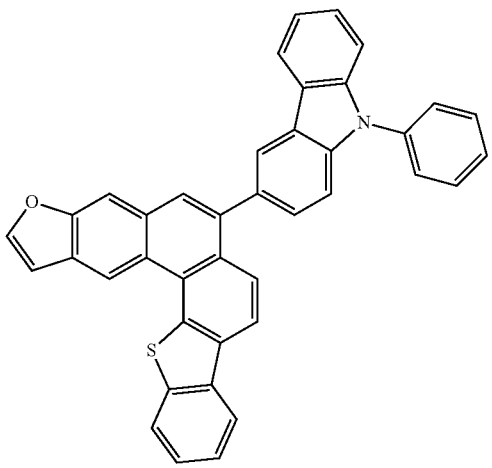
13-E
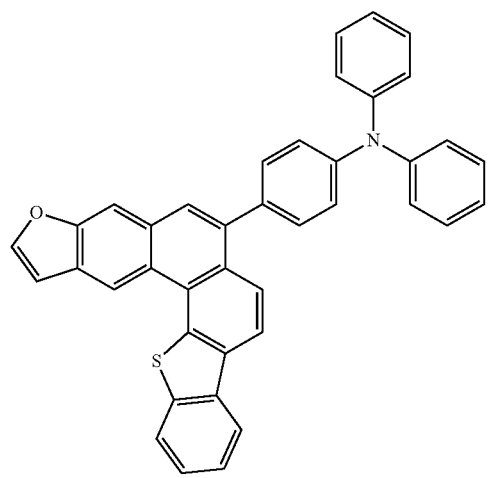
13-F
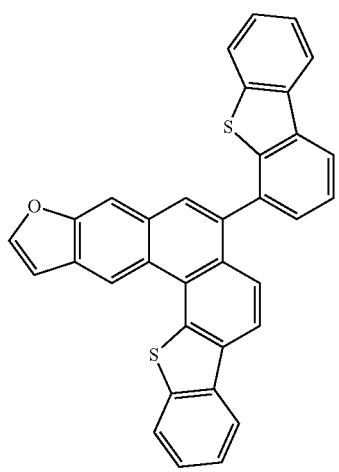

13-G
13-H
14-A
14-B
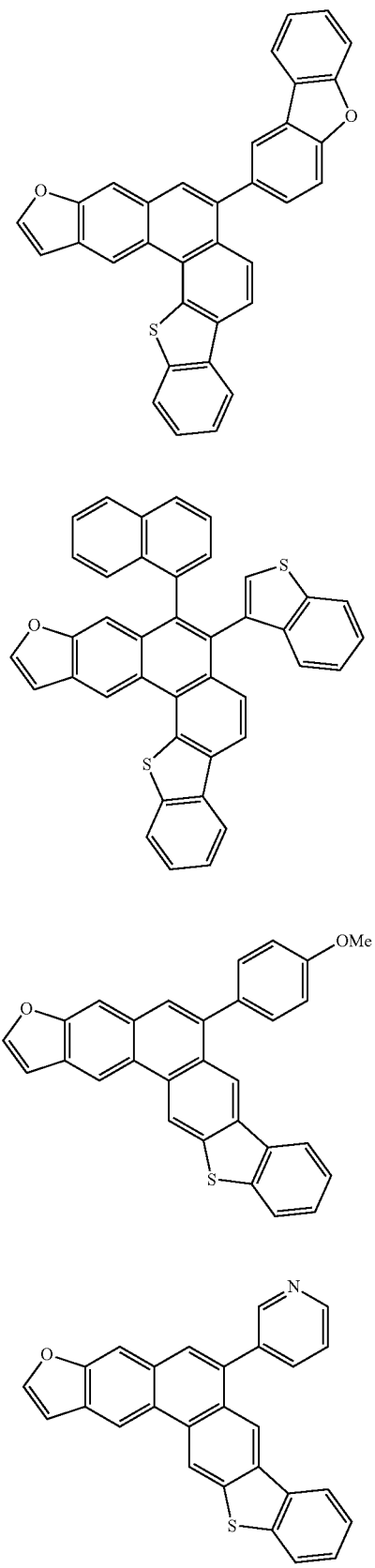
14-C
14-D
14-E
14-F
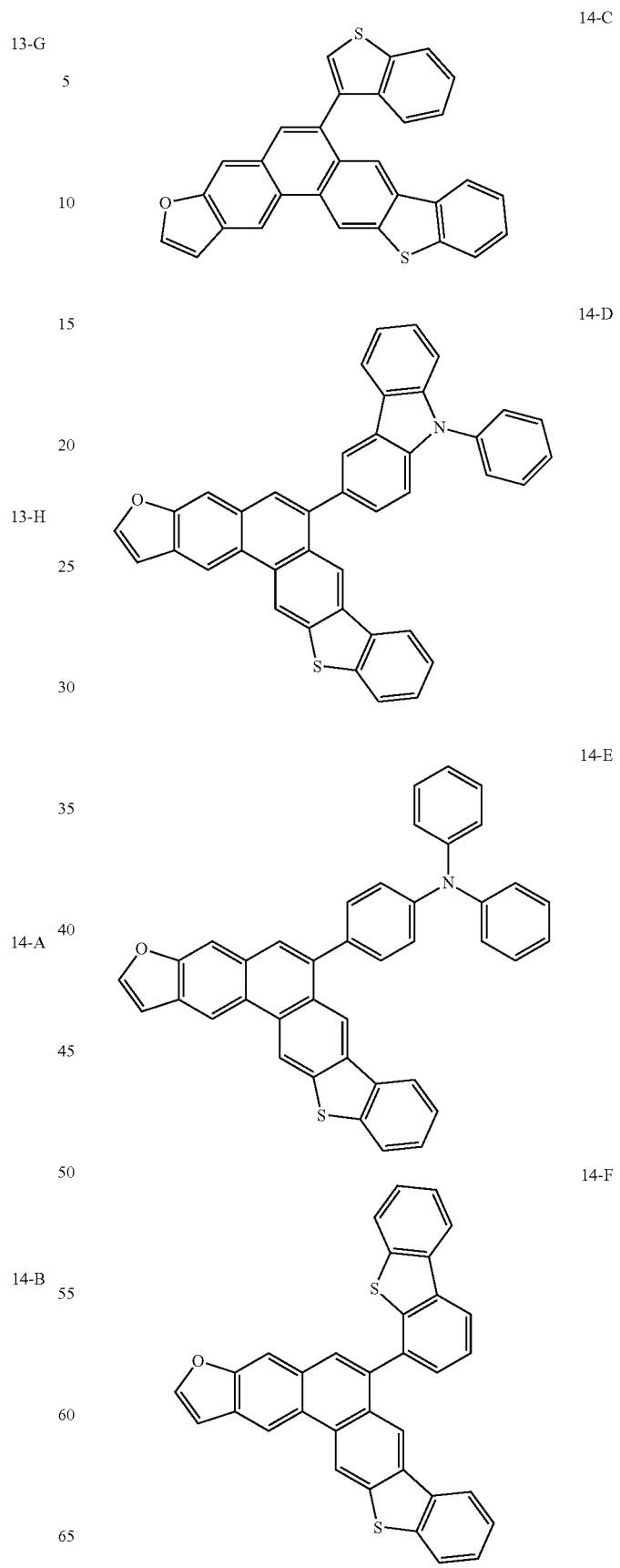

14-G
14-H
15-A
15-B
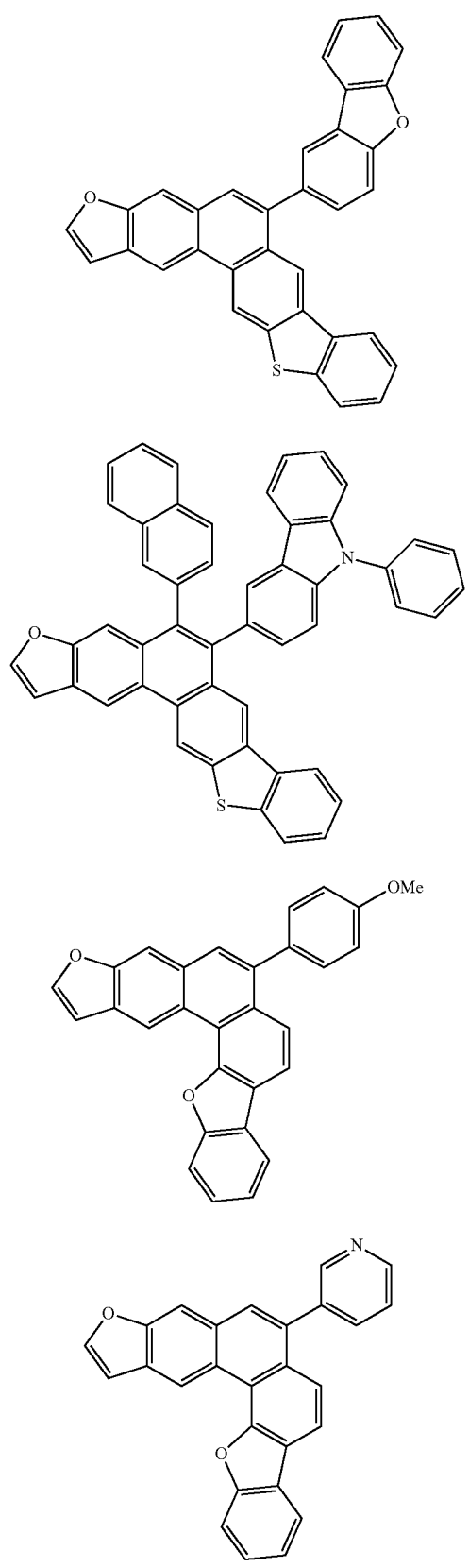
15-C
15-D
15-E
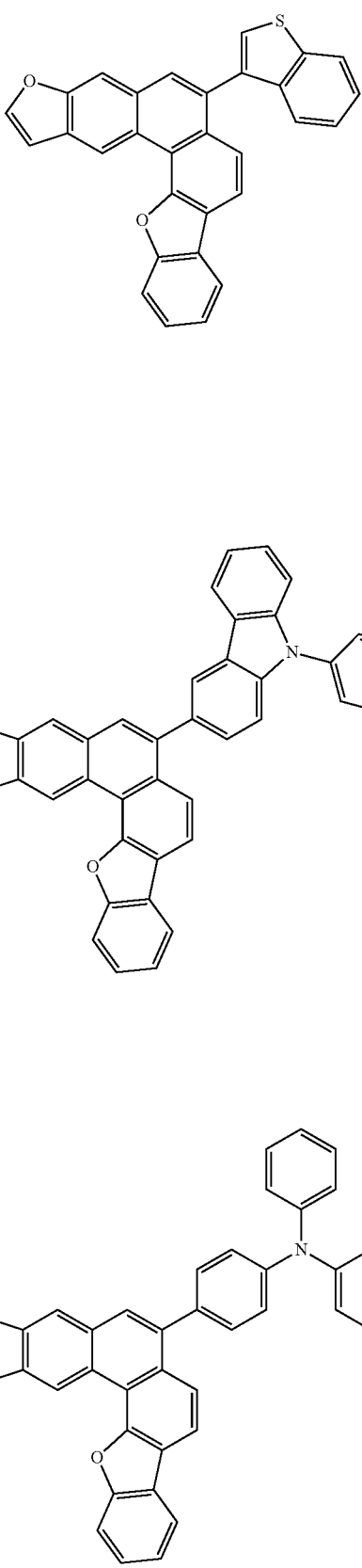

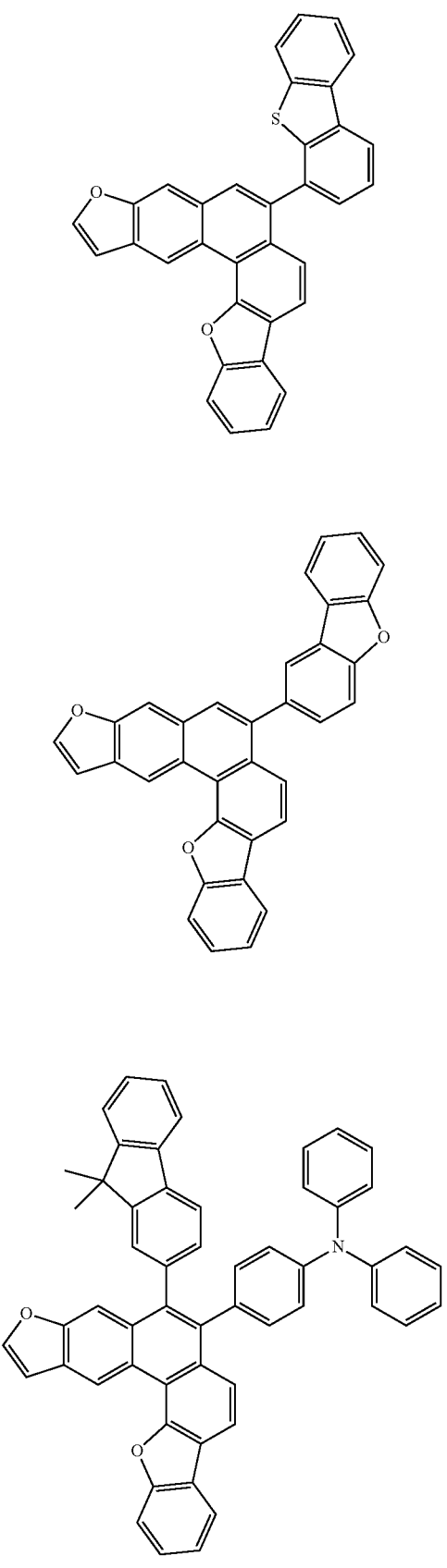
15-F
15-G
15-H
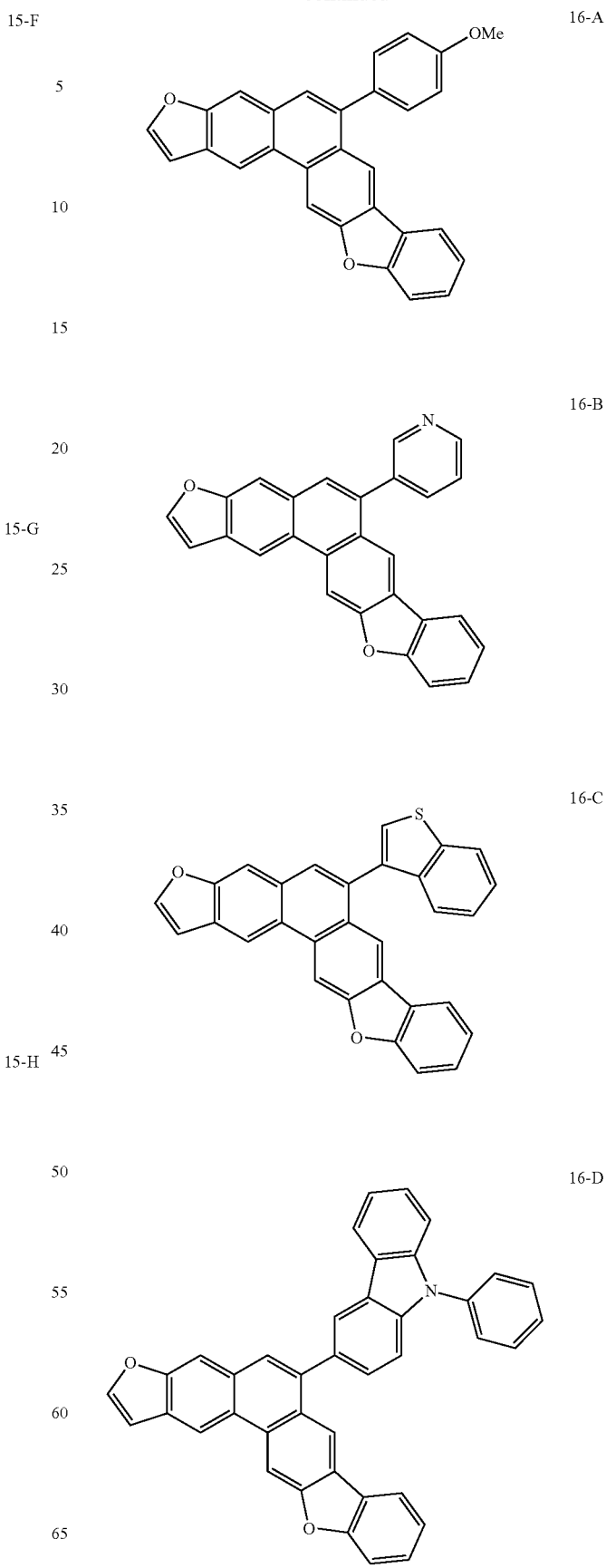
16-A
16-B
16-C
16-D

-continued
16-E
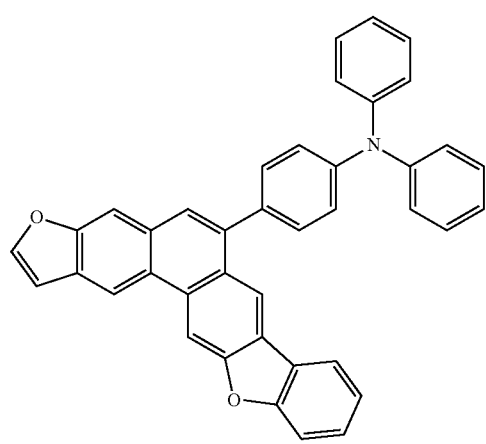
16-F
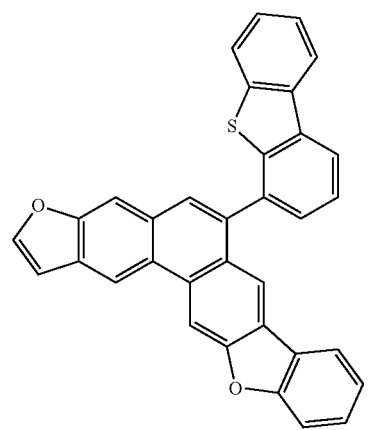
16-G
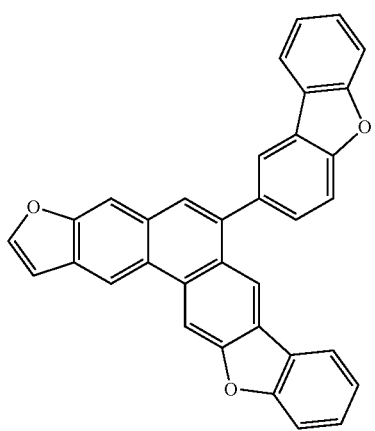
16-H
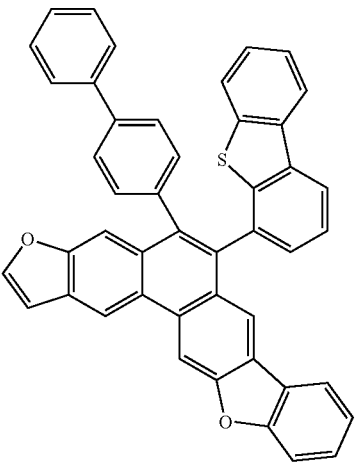
21-A
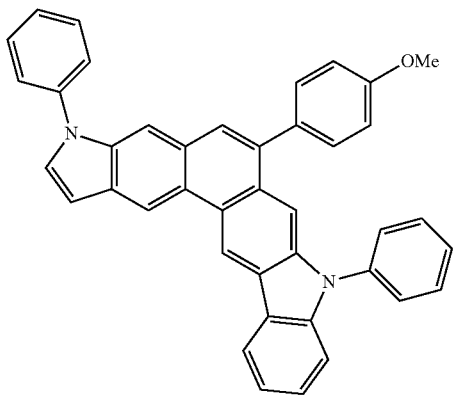
21-B
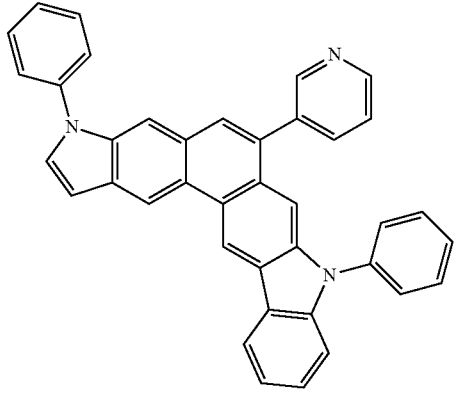
21-C
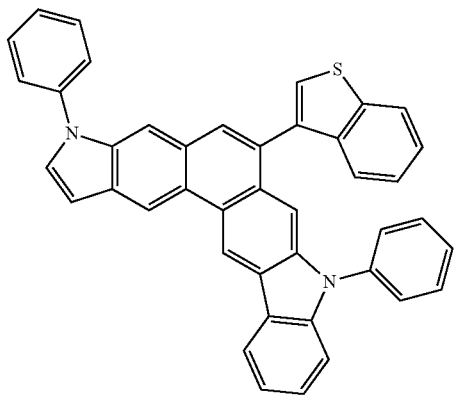

21-D
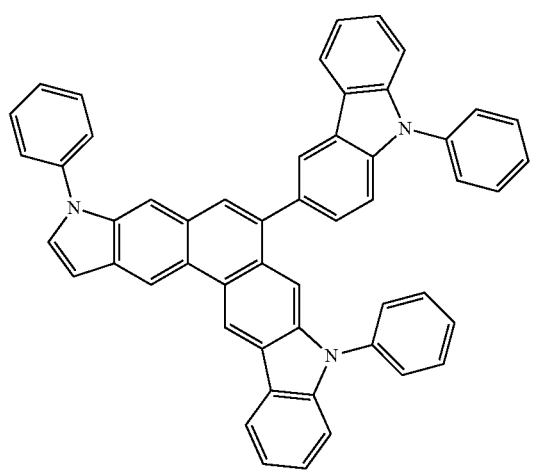
21-G
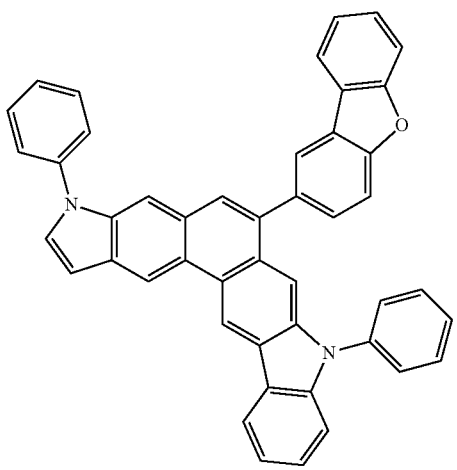
21-E
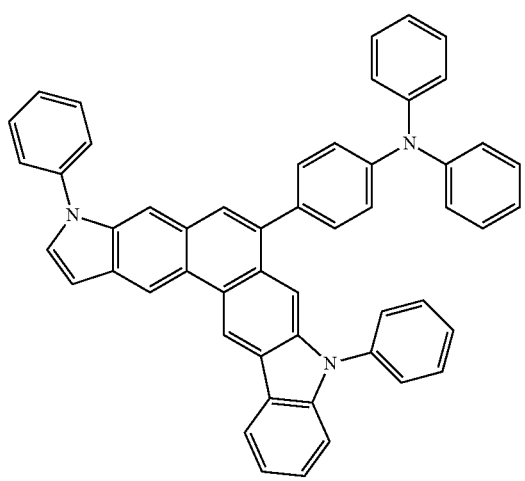
21-H
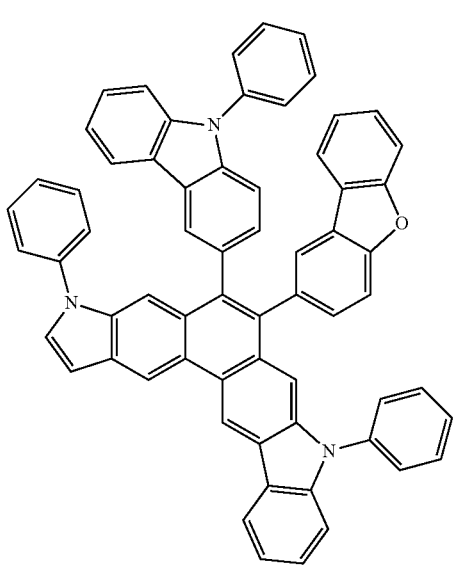
21-F
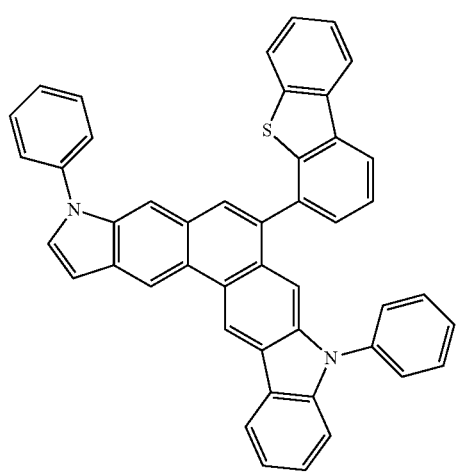
22-A
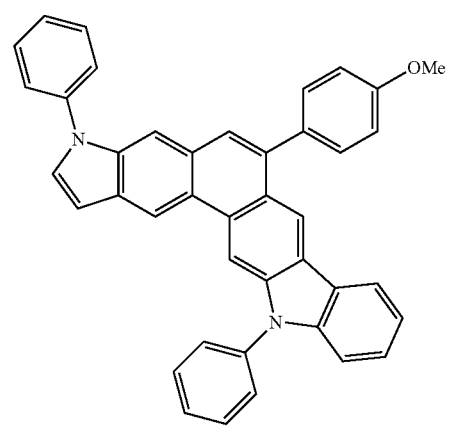

-continued
22-B
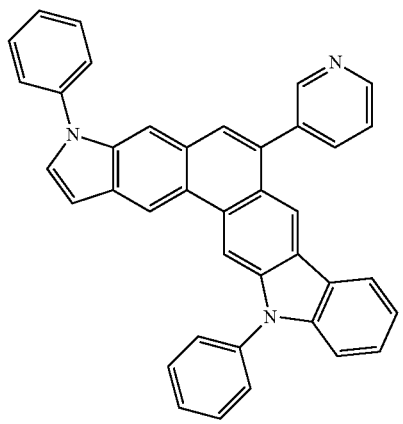
22-C
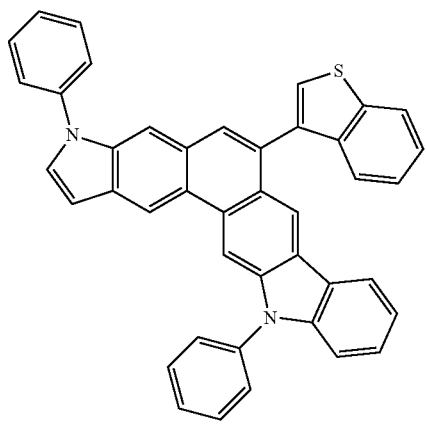
22-D
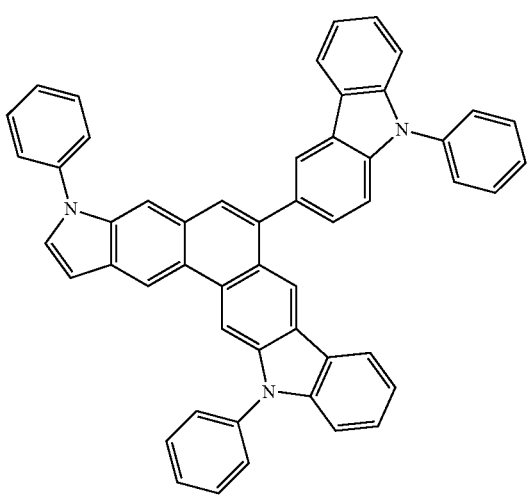
-continued
22-E
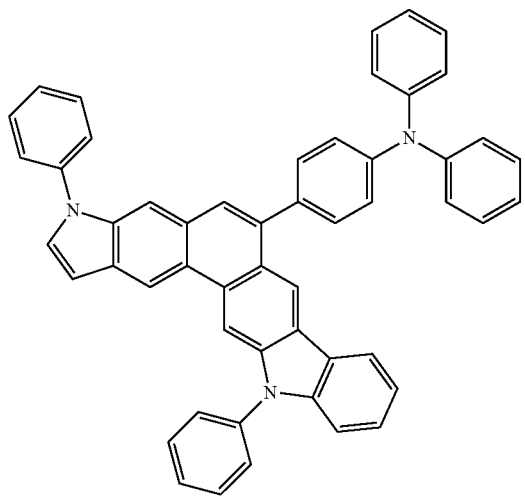
22-F
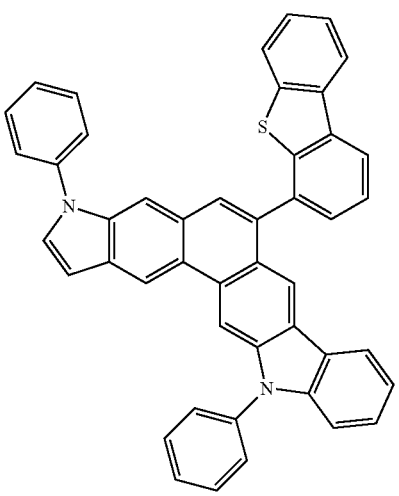
22-G
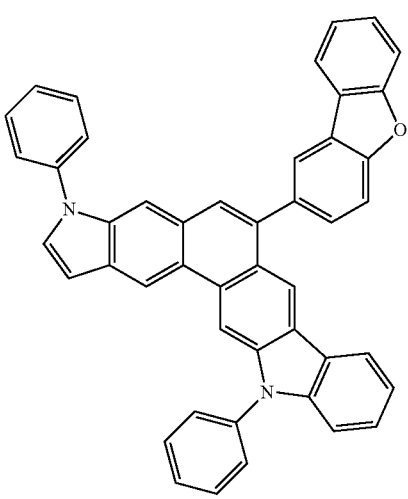

22-H
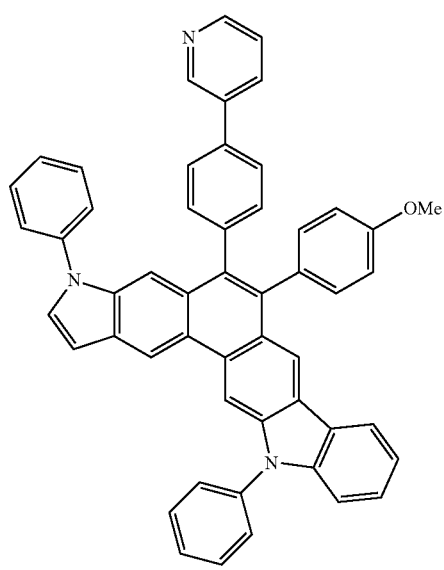
23-A
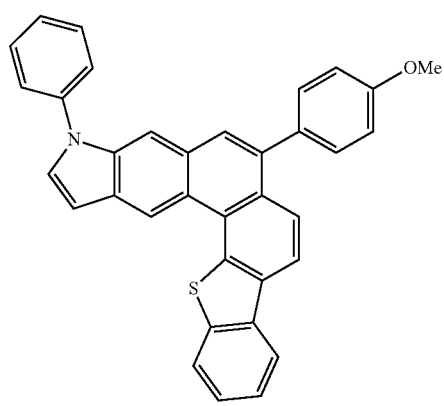
23-B
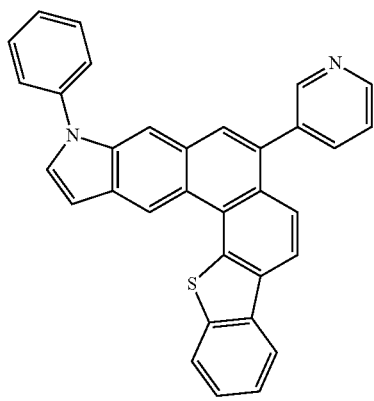
23-C
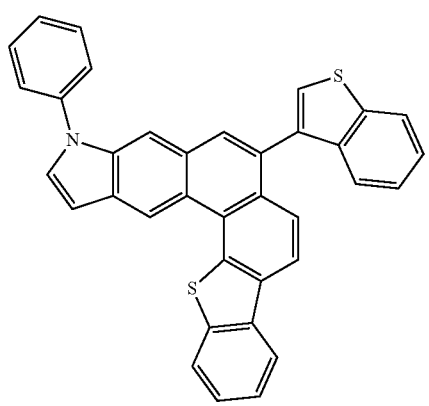
23-D
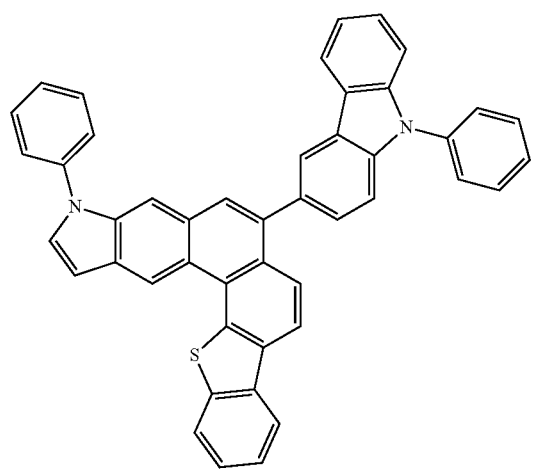
23-E
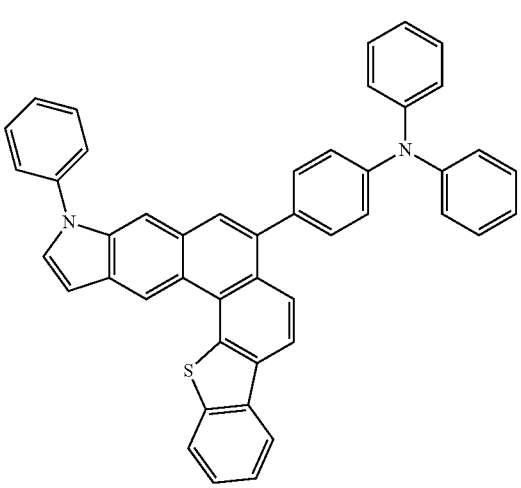

-continued
23-F
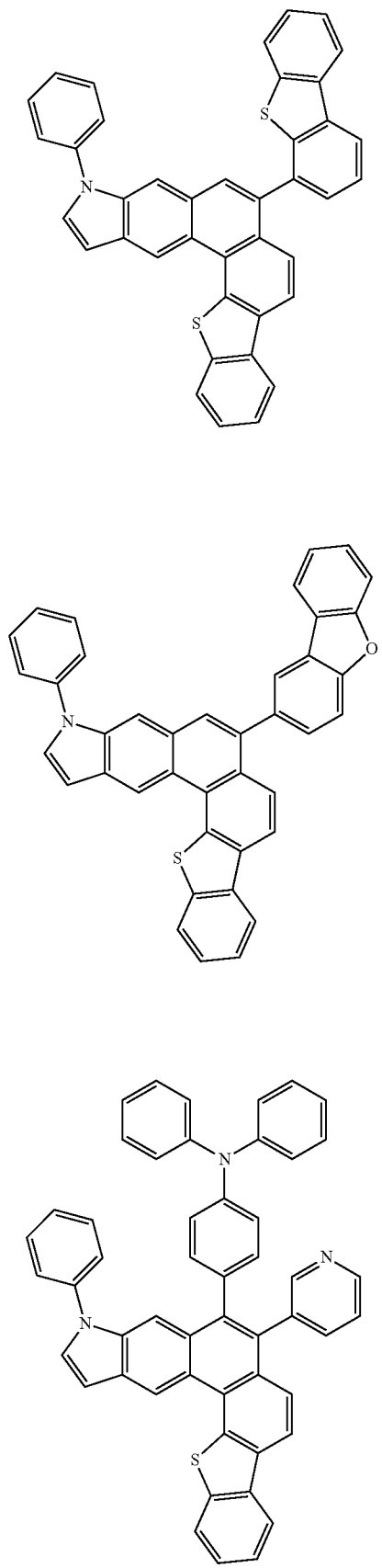
23-G
23-H
-continued
24-A
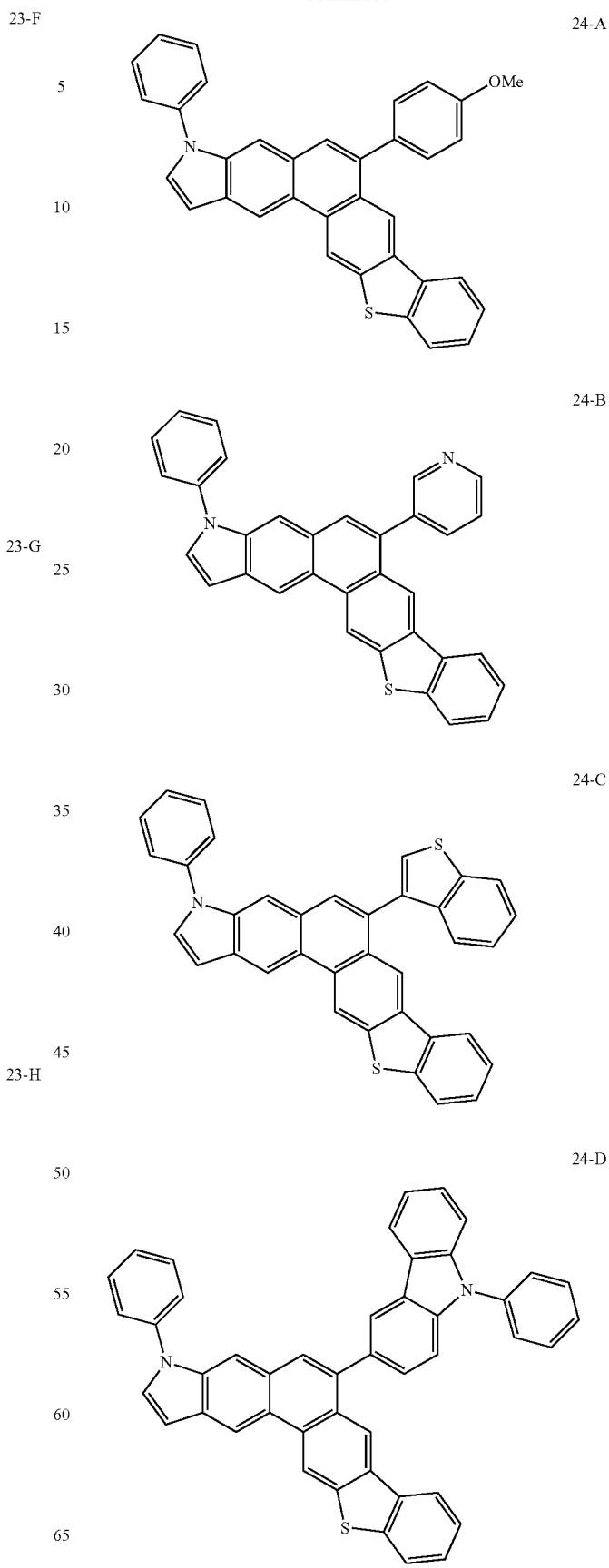
24-B
24-C
24-D 24-E
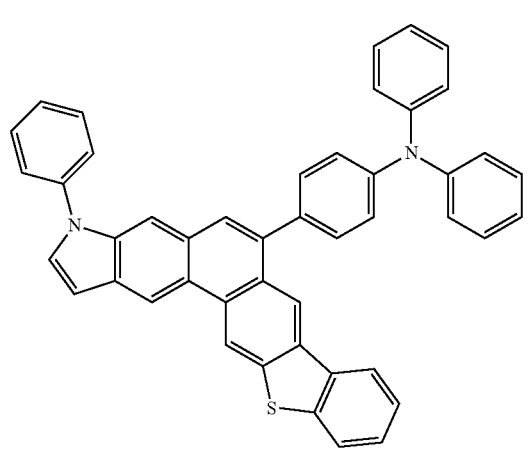
24-F
24-G
24-H
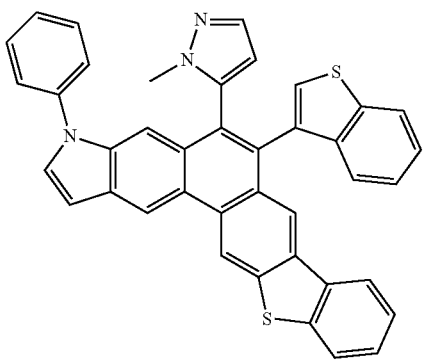
25-A
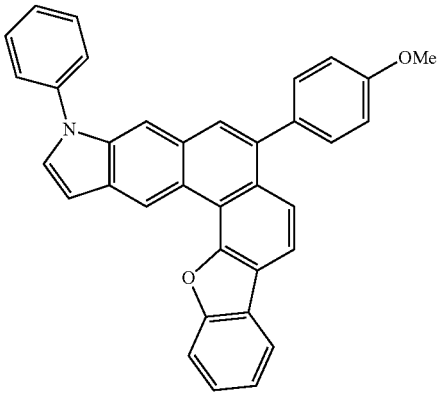
25-B
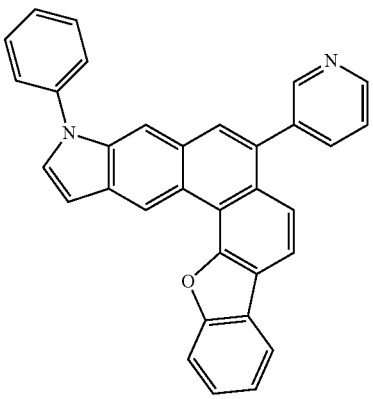
25-C
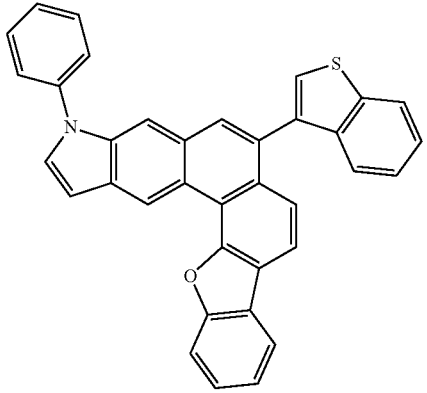

25-D
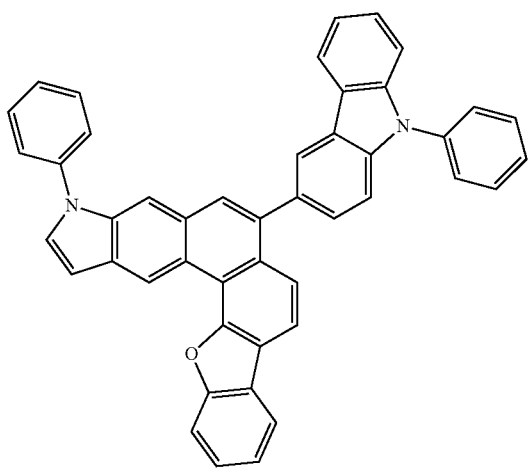
25-G
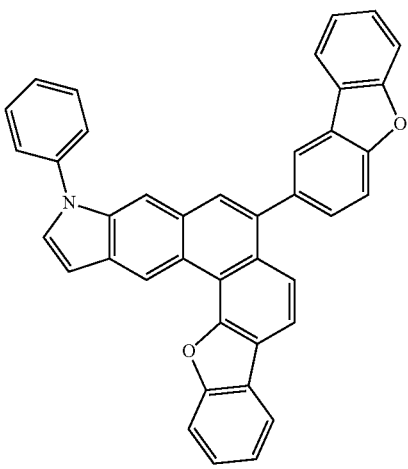
25-E
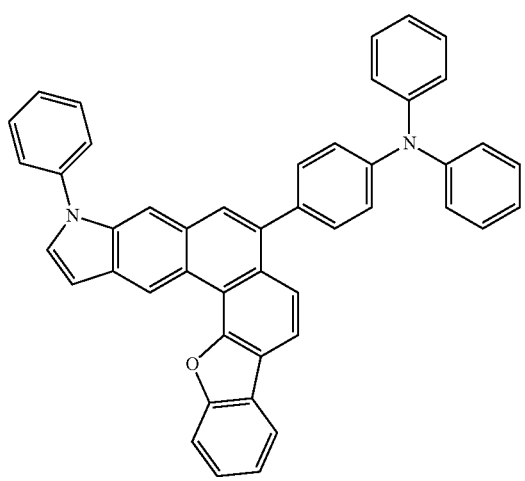
25-H
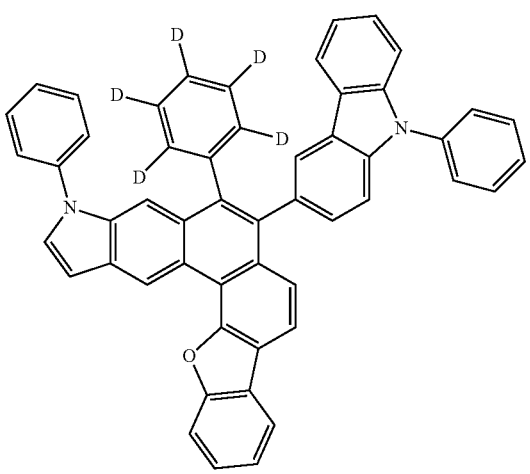
25-F
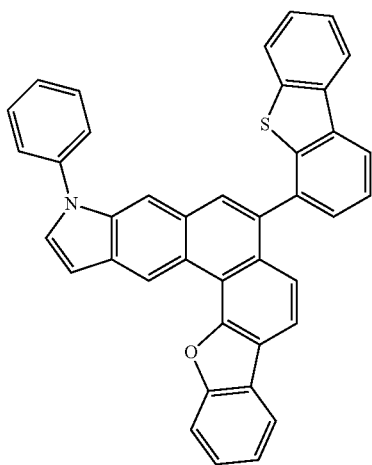
26-A
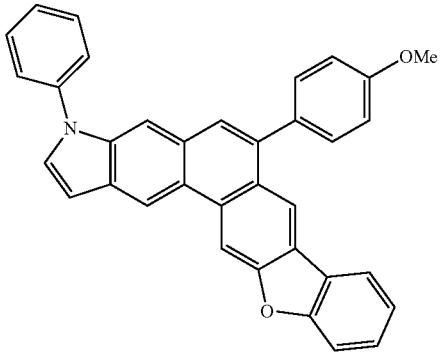

26-B
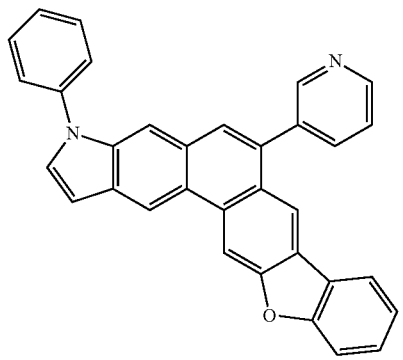
26-C
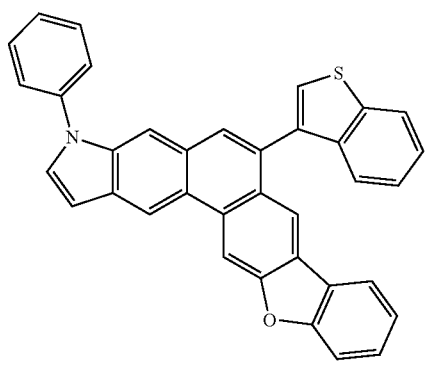
26-D
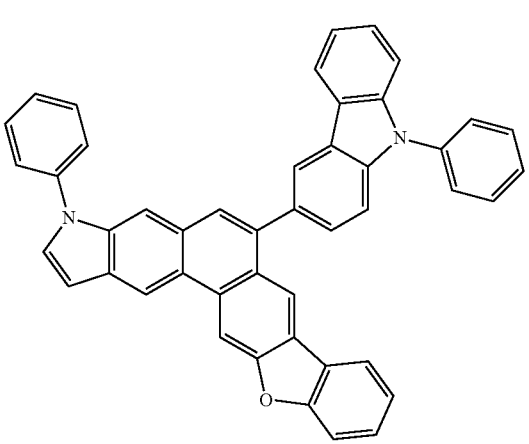
26-E
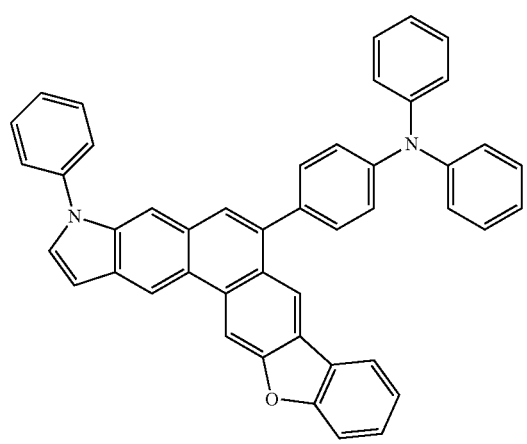
26-F
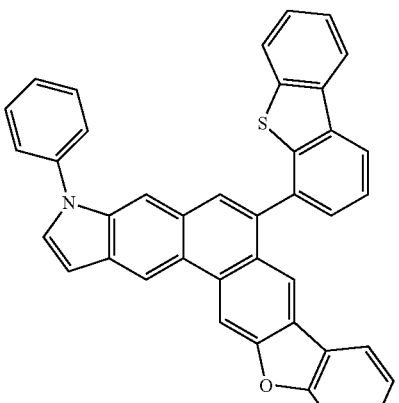
26-G
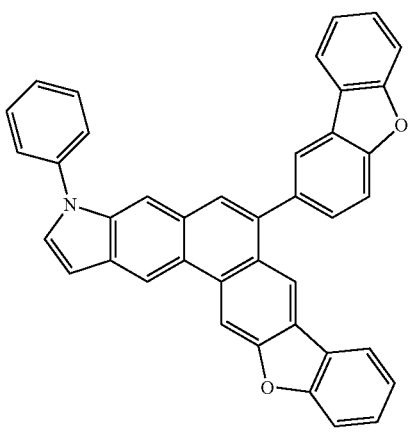
26-H
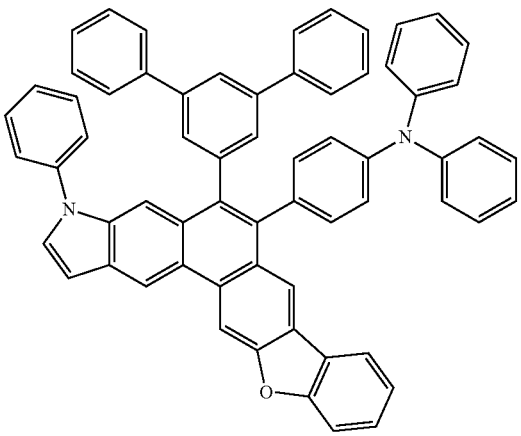
31-A
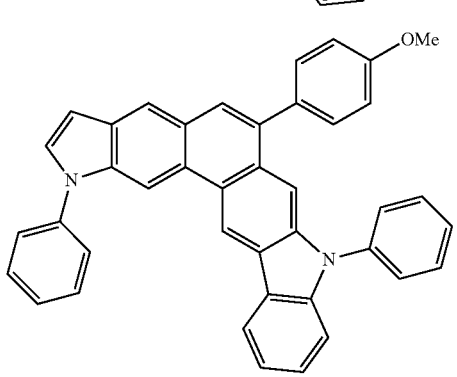

31-B
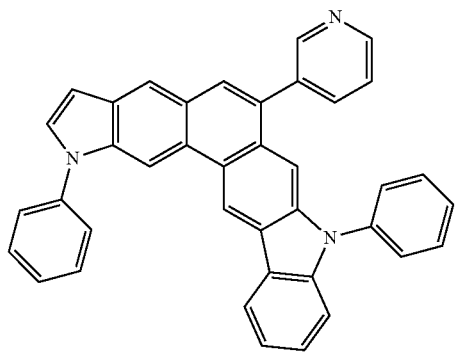
31-C
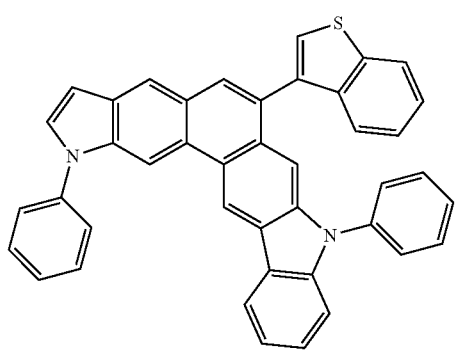
31-D
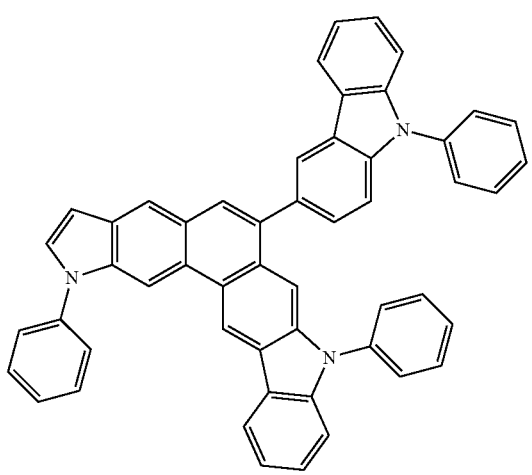
31-E
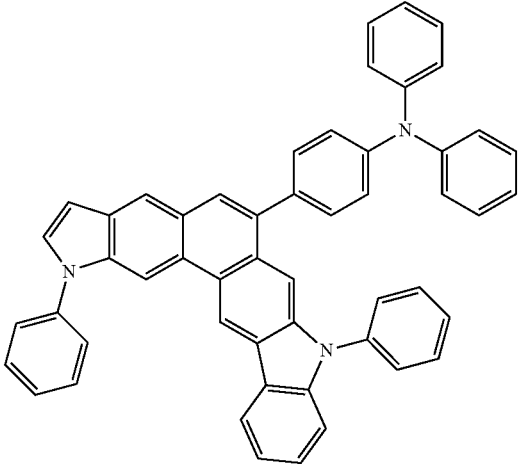
31-F
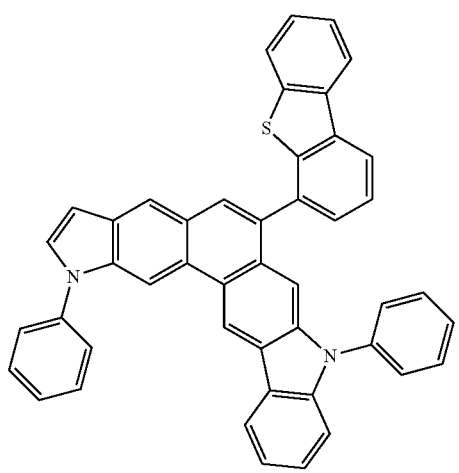
31-G
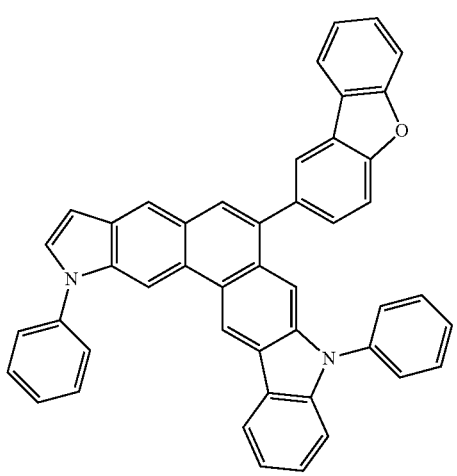

-continued
31-H
32-A
32-B
32-C
32-D
32-E
32-F
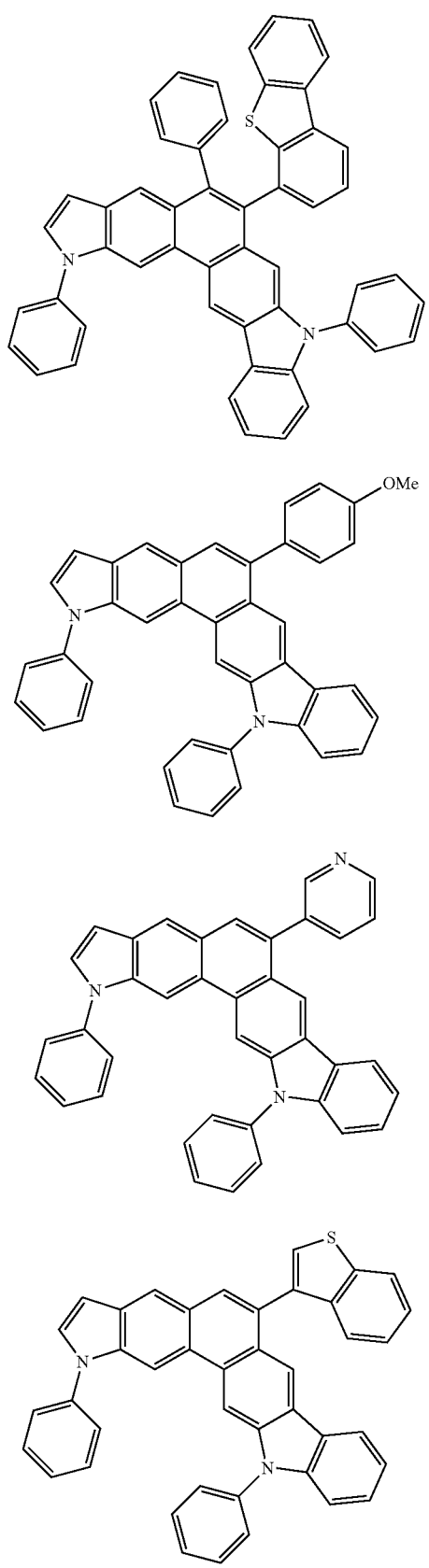

32-G
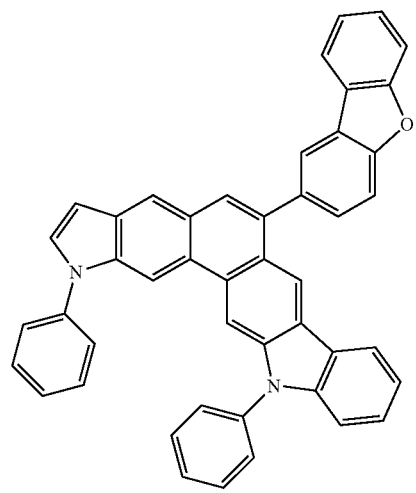
32-H
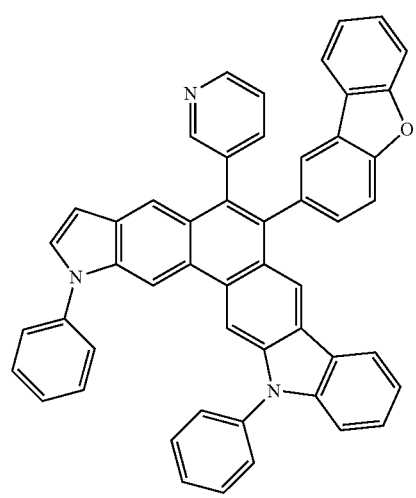
33-A
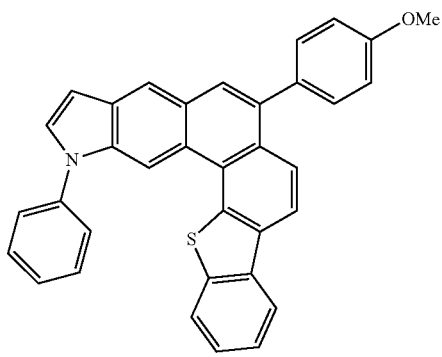
33-B
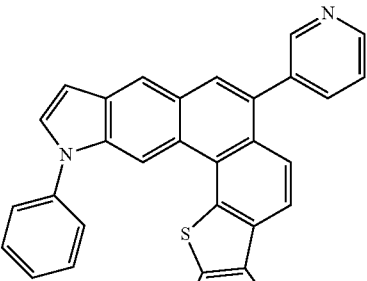
33-C
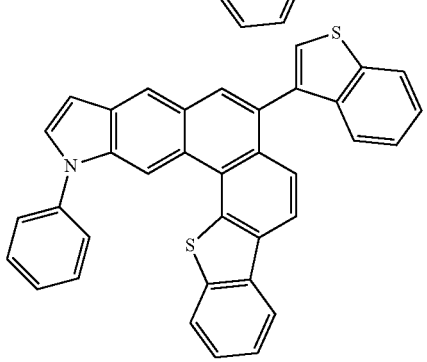
33-D
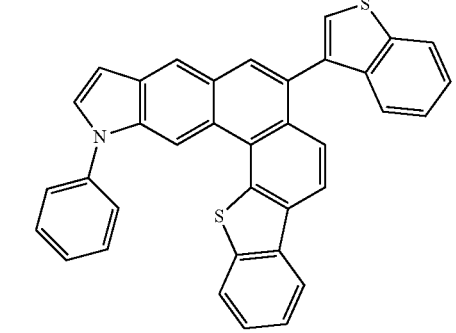
33-E
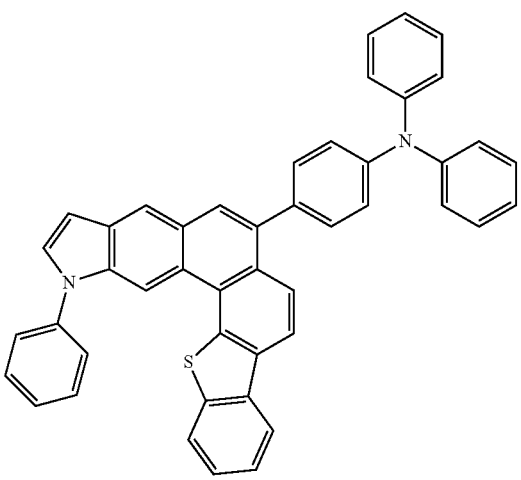

33-F
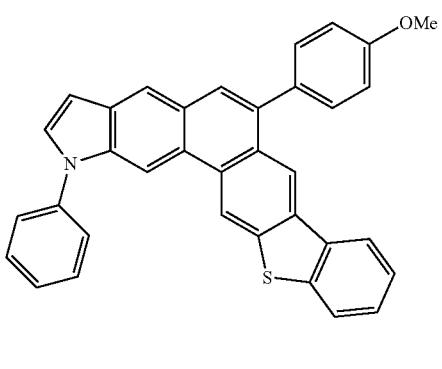
34-A
33-G
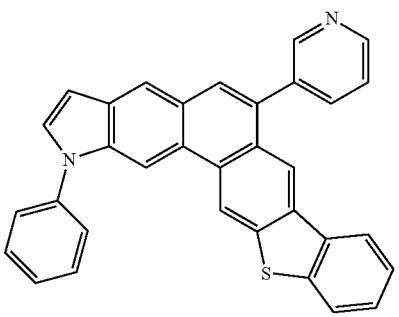
34-B
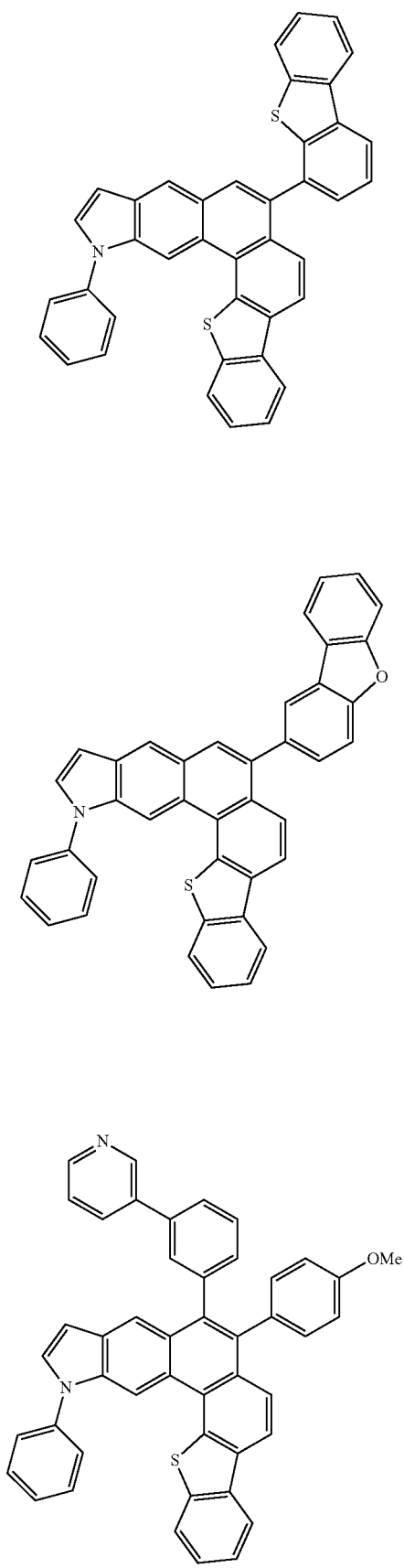
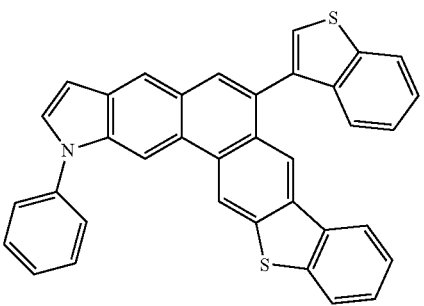
34-C
33-H
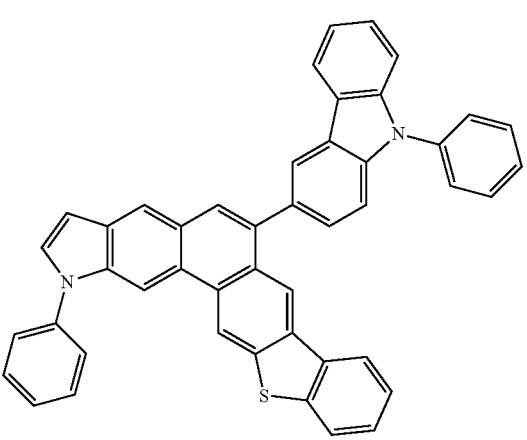
34-D 34-E
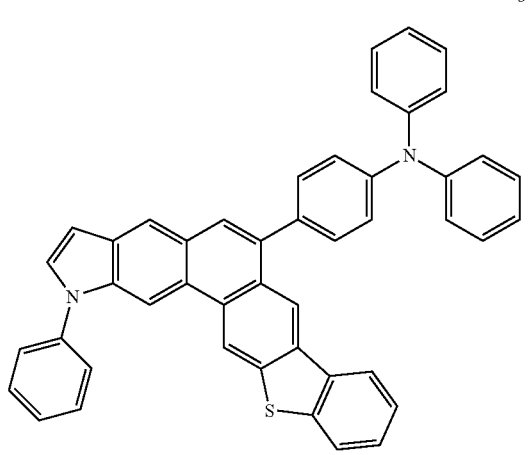
34-F
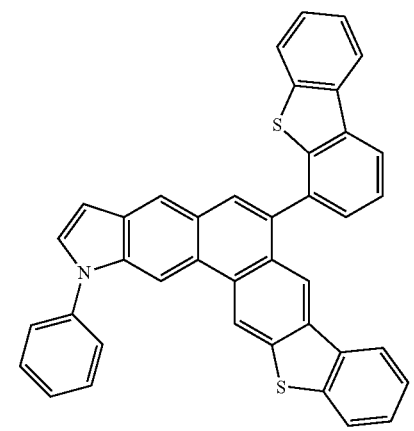
34-G
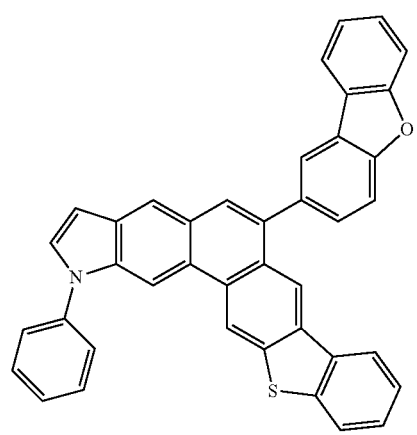
34-H
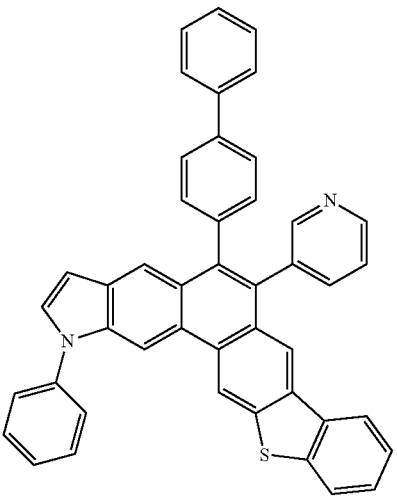
35-A
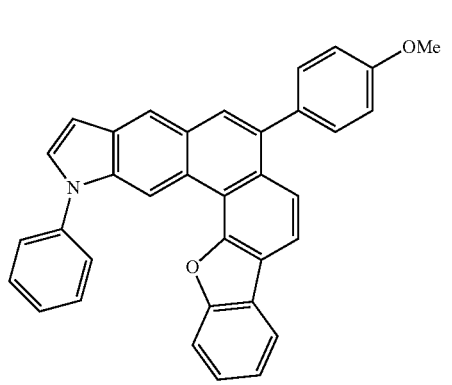
35-B
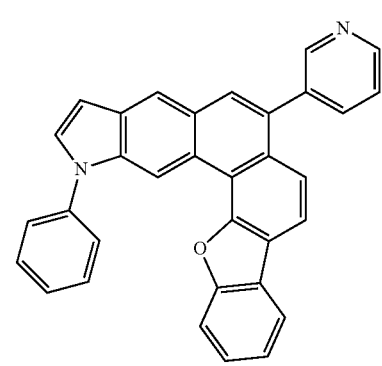
35-C
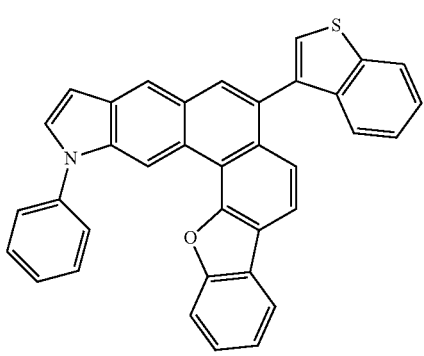

-continued
35-D
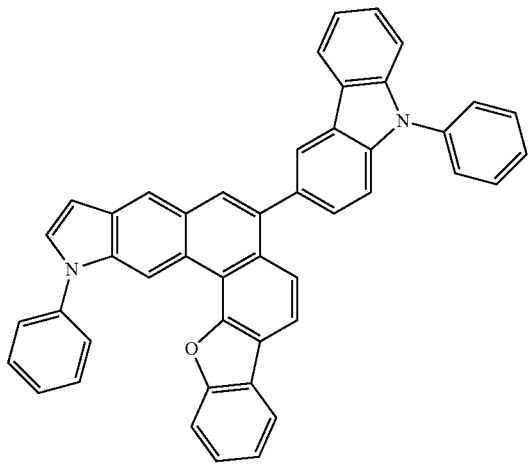
35-E
35-F
35-G
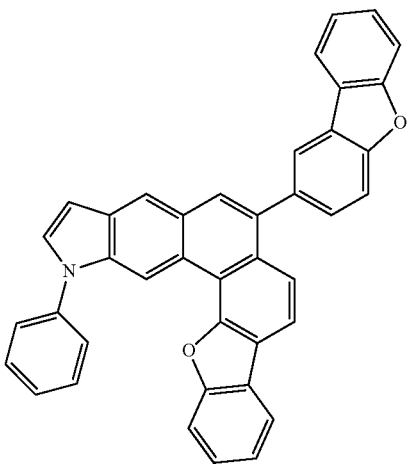
35-H
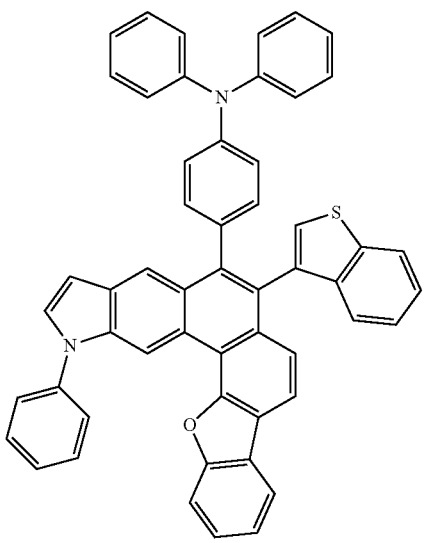
36-A
36-B
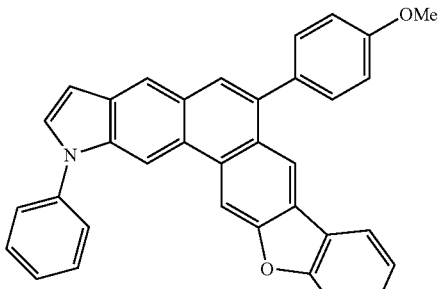

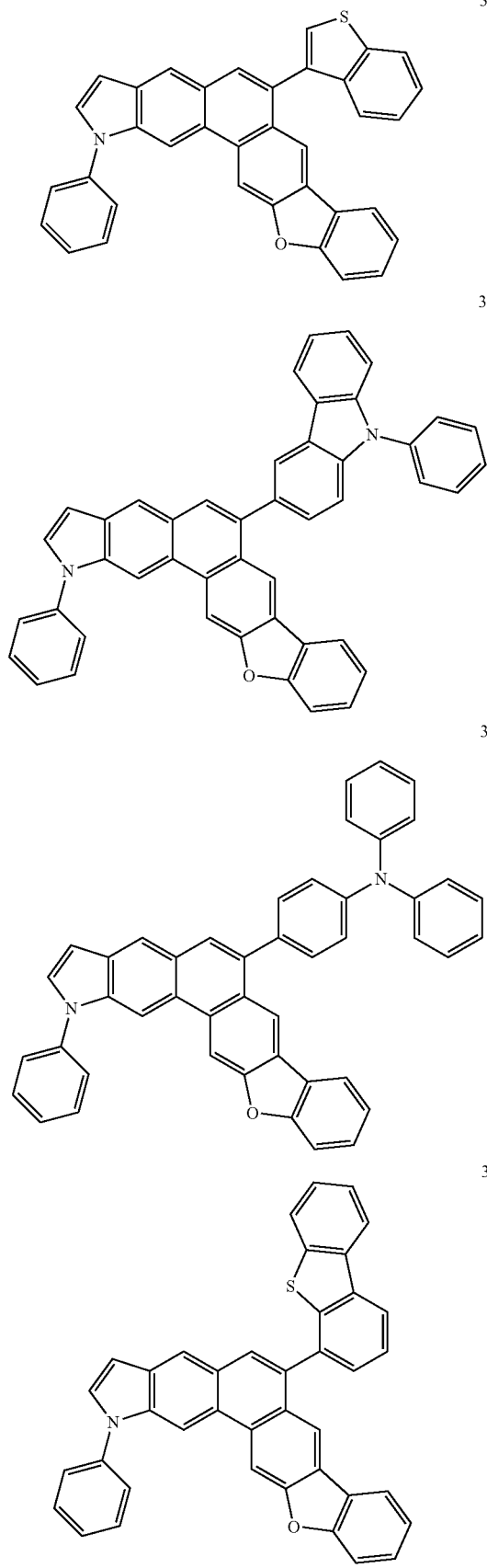
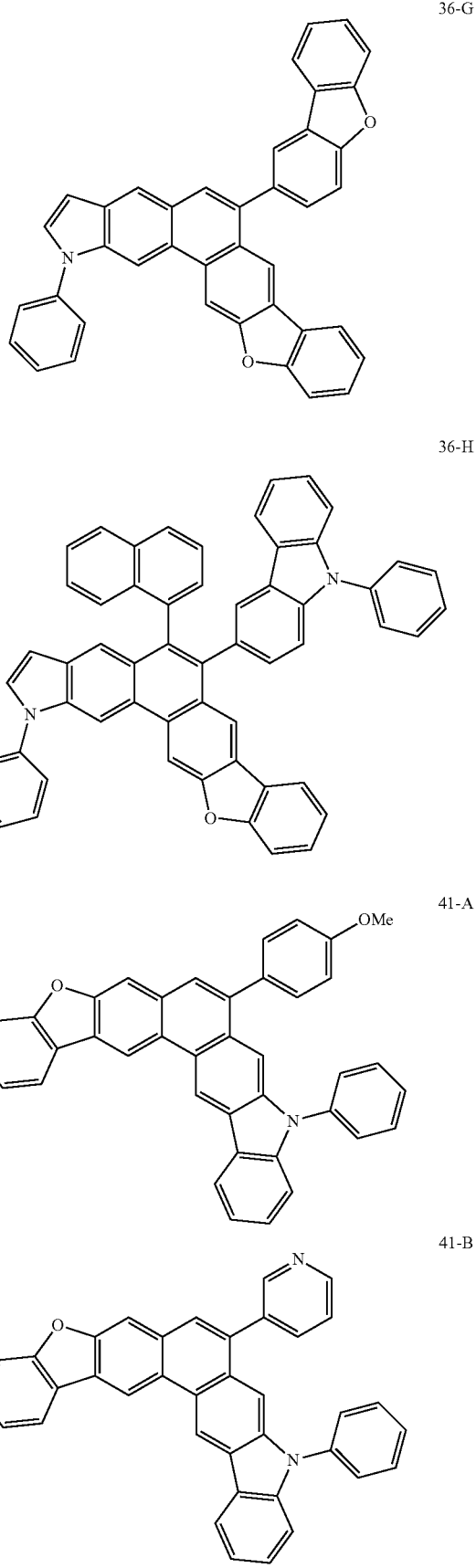

41-C
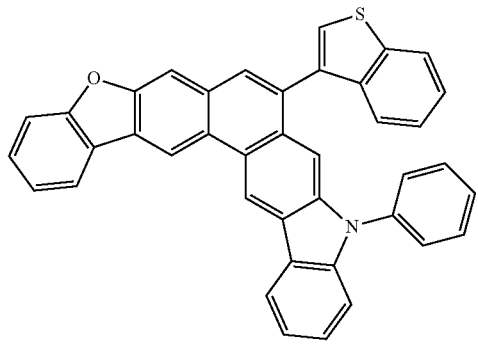
41-D
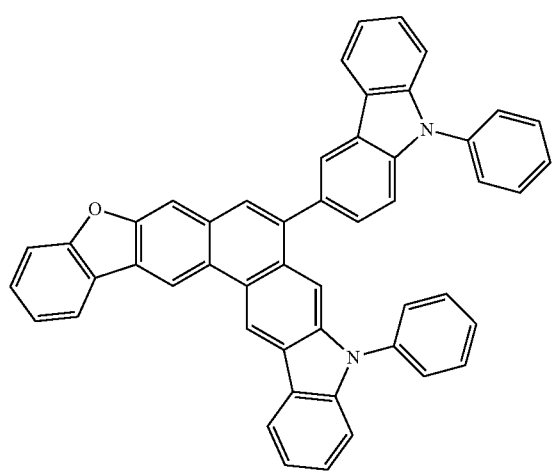
41-E
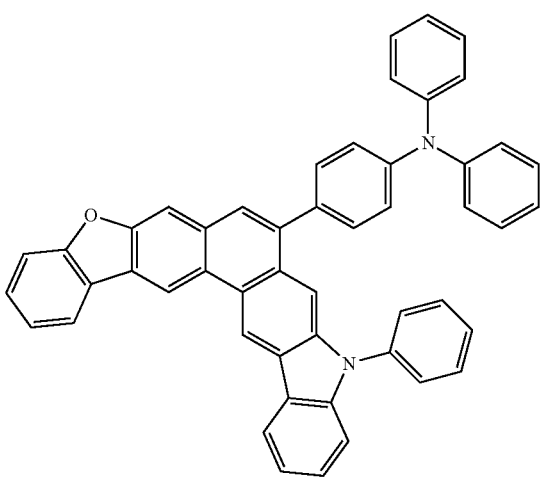
41-F
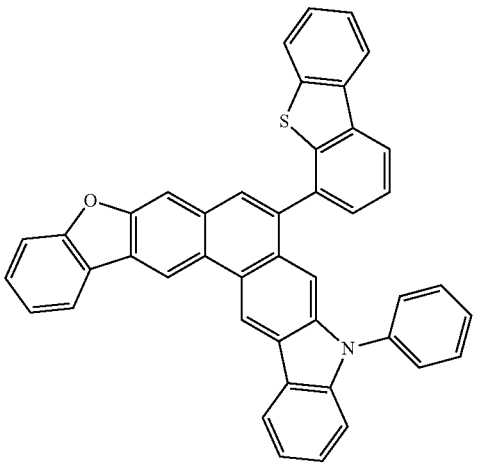
41-G
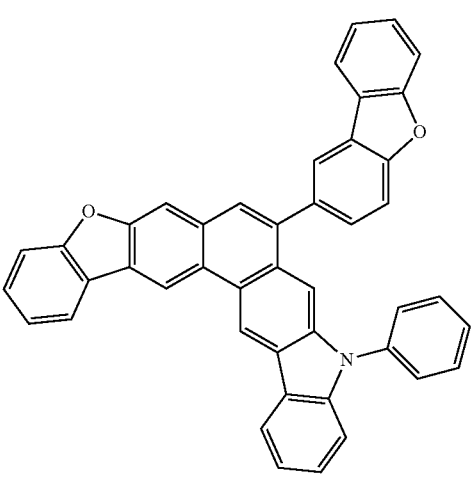
41-H
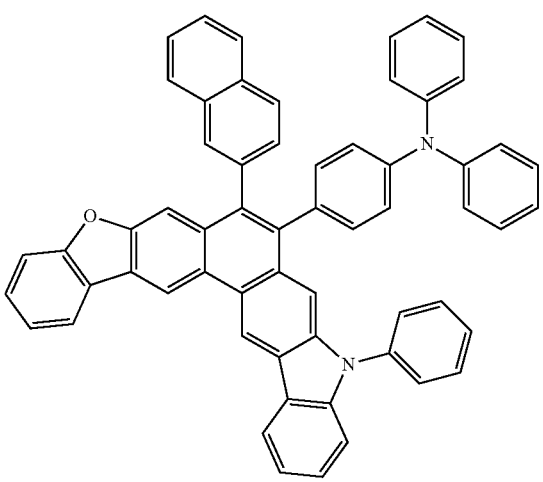

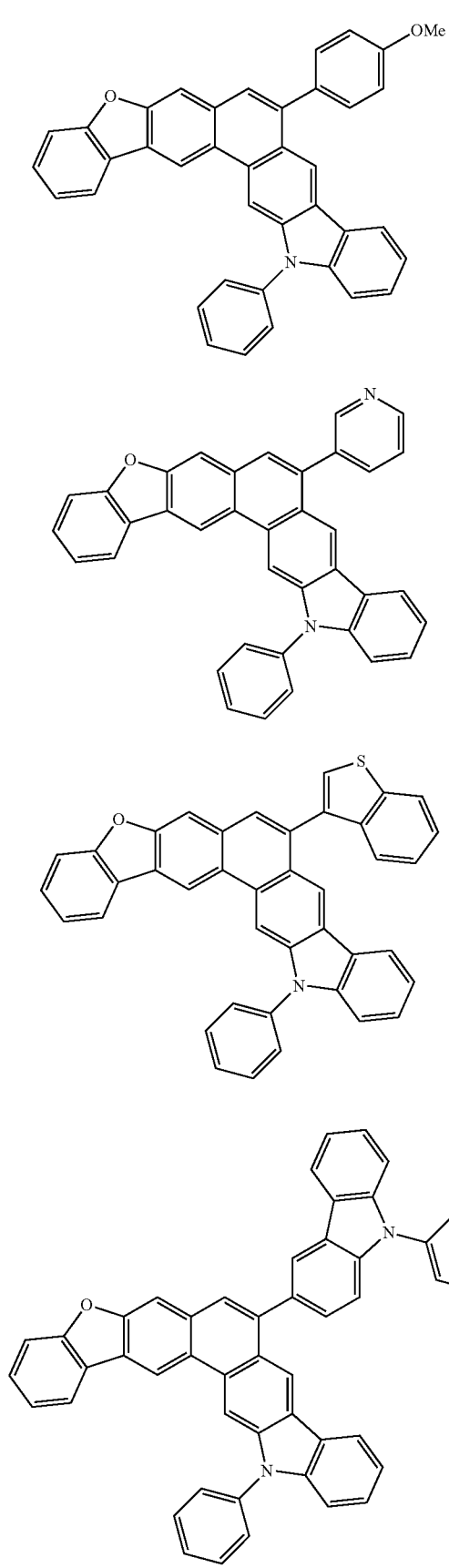

42-H
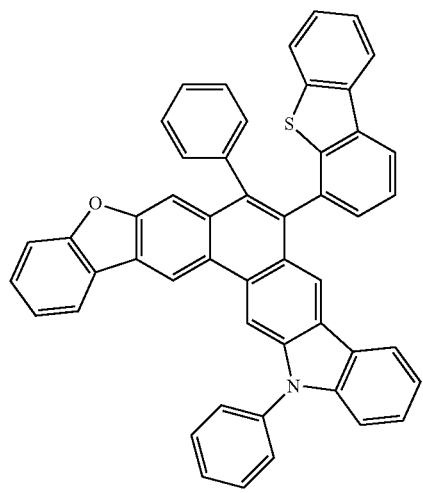
43-A
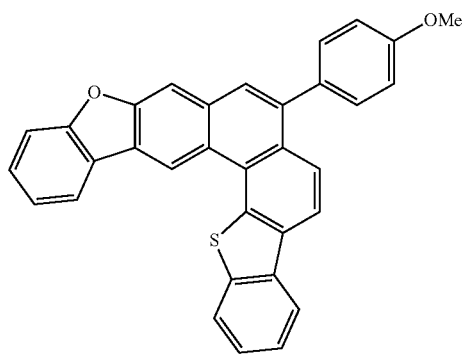
43-B
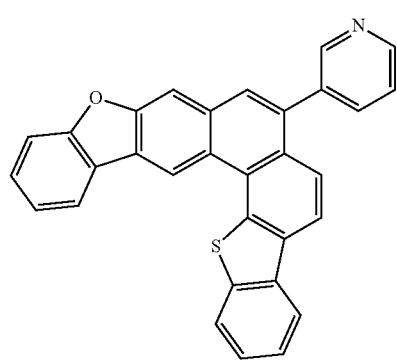
43-C
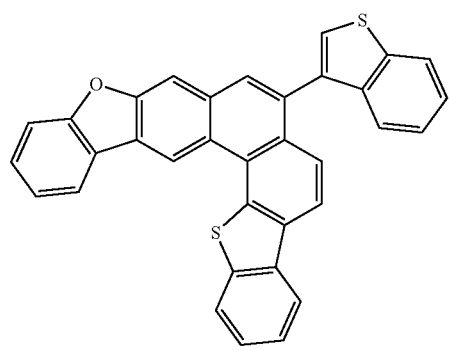
43-D
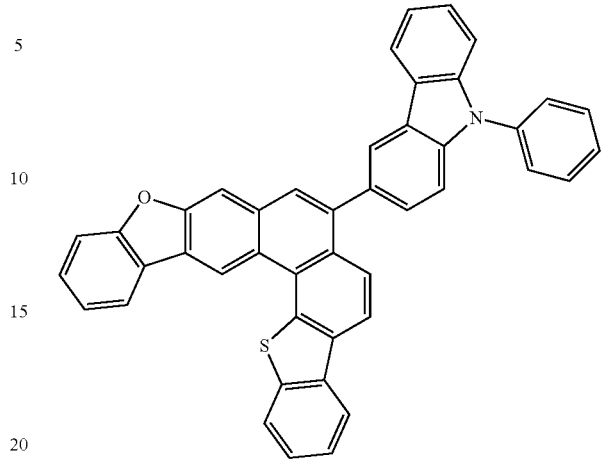
43-E
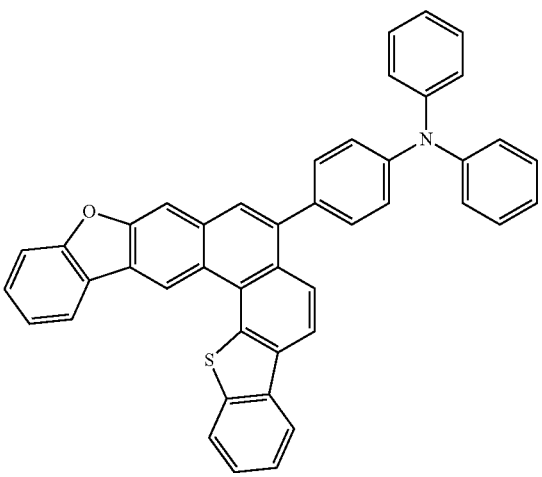
43-F
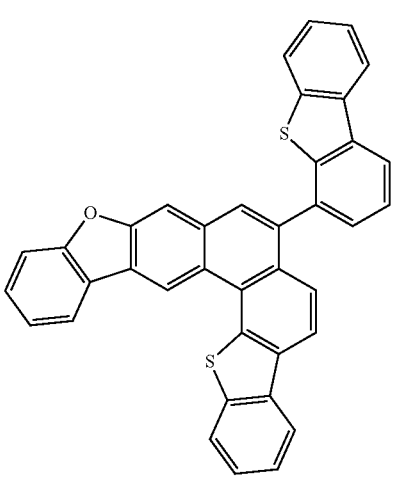

43-G
43-H
44-A
44-B
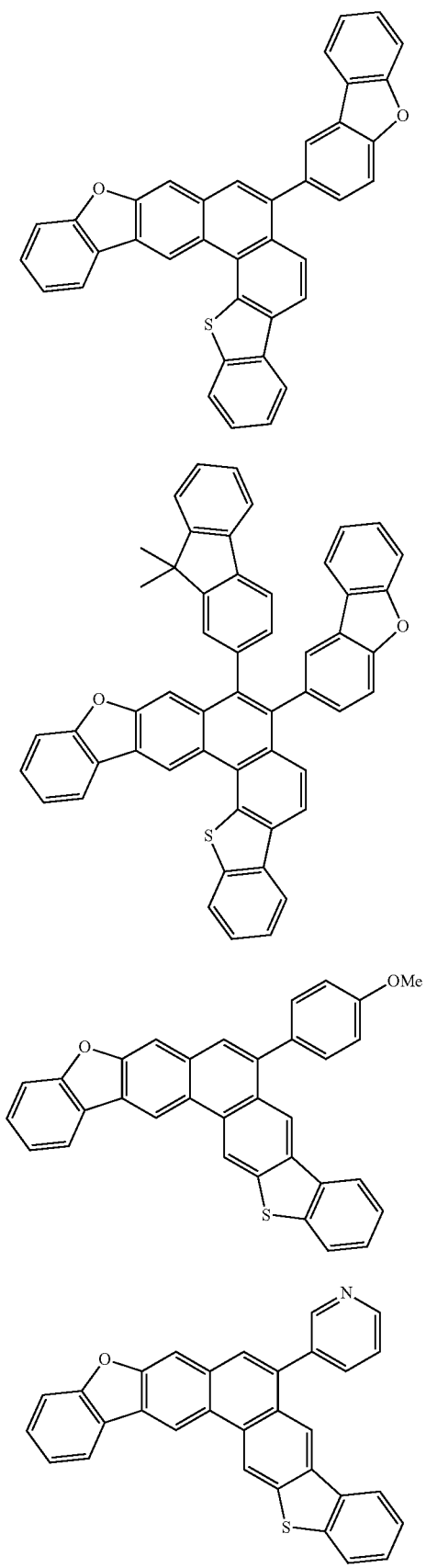
44-C
44-D
44-E
44-F
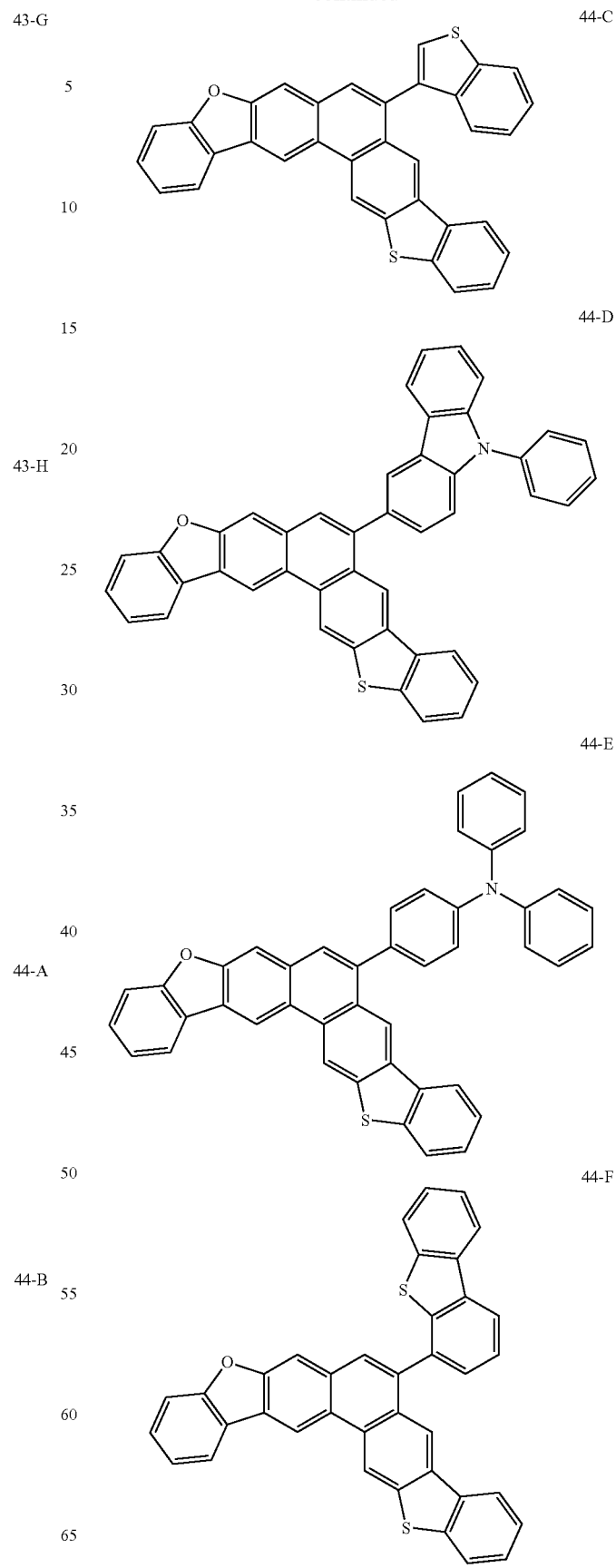

-continued
44-G
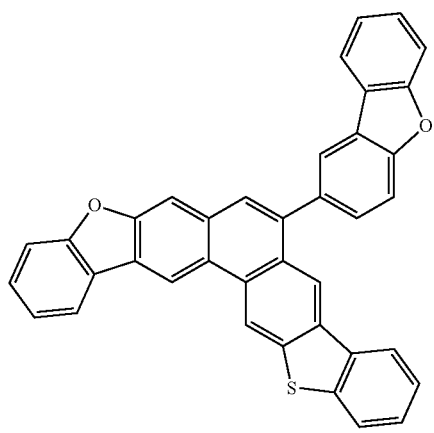
44-H
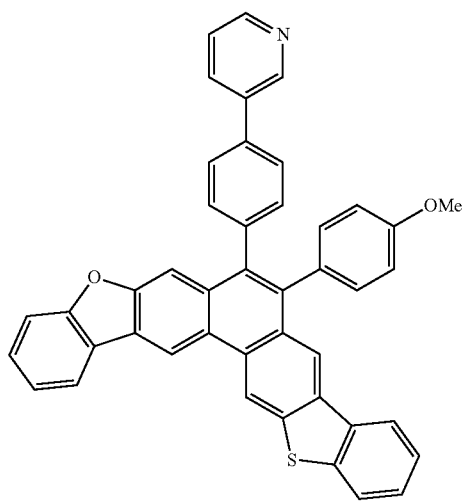
45-A
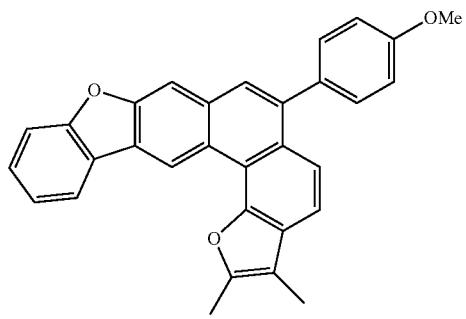
45-B
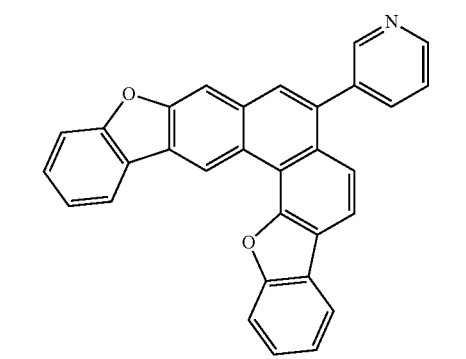
-continued
45-C
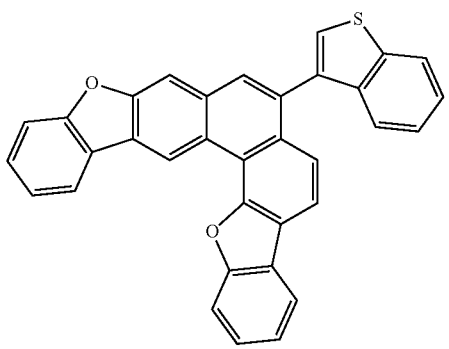
45-D
45-E
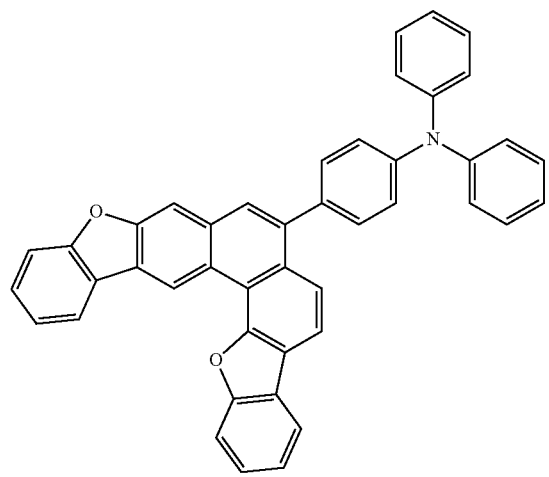

45-F
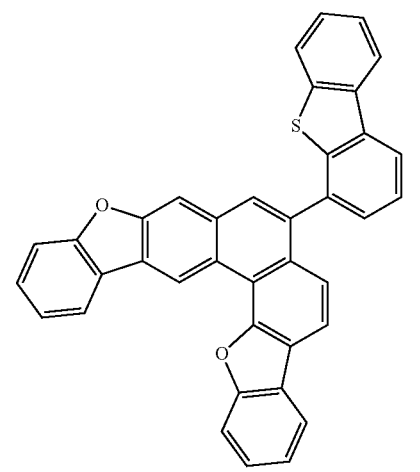
45-G
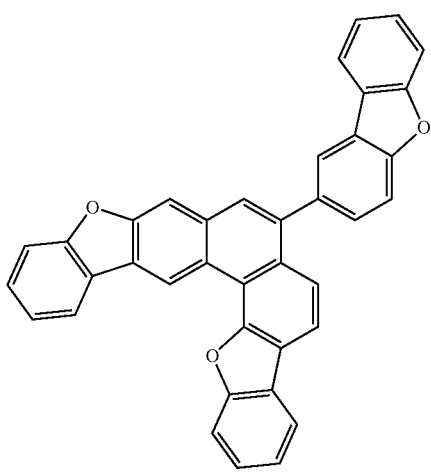
45-H
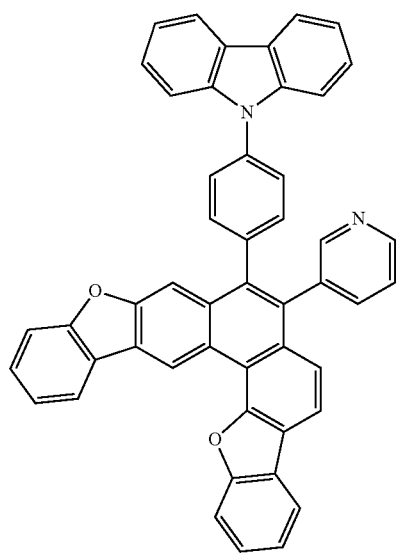
46-A
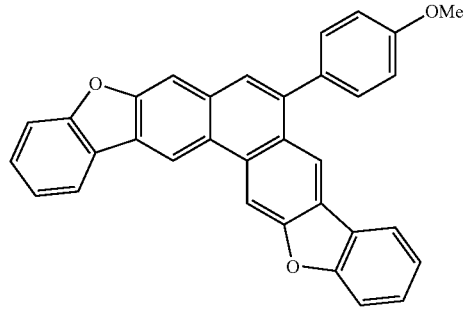
46-B
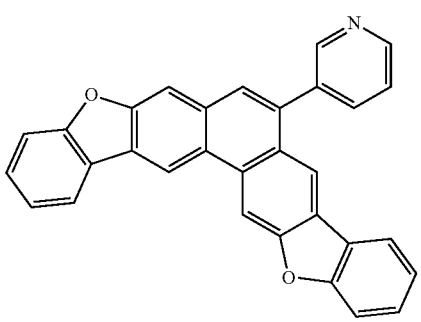
46-C
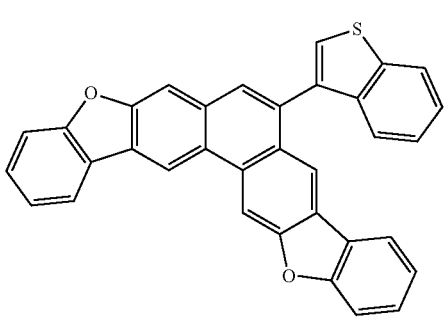
46-D
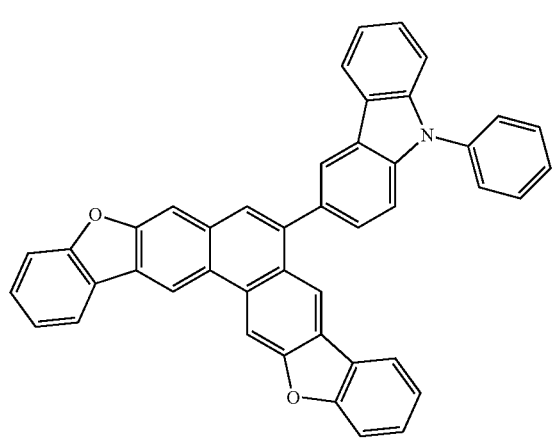

46-E
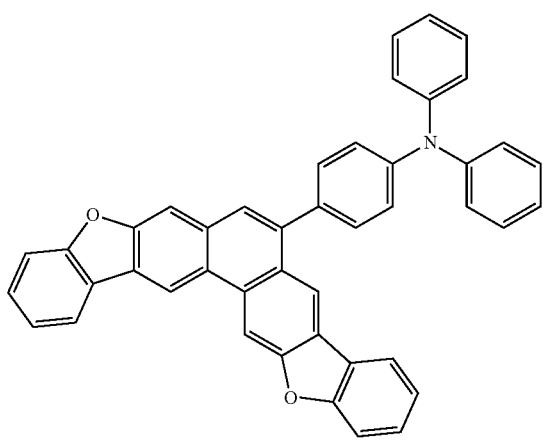
46-F
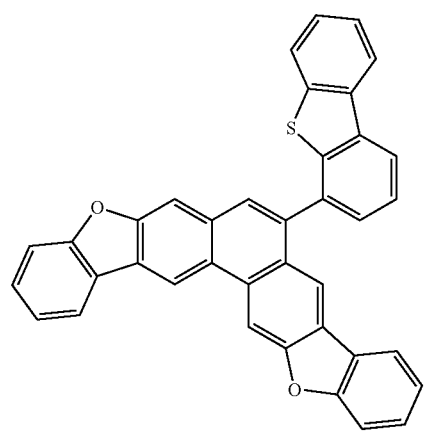
46-G
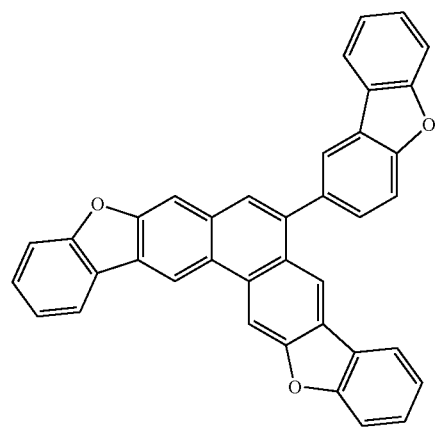
46-H
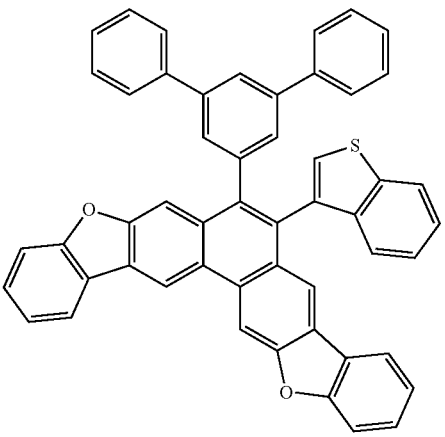
51-A
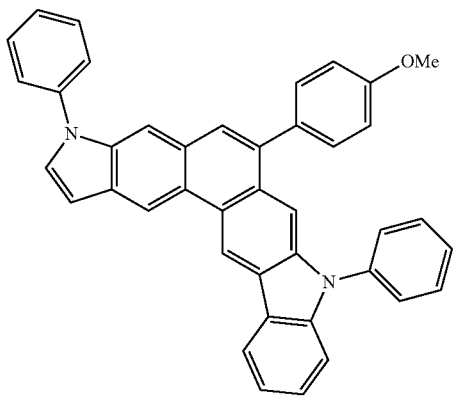
51-B
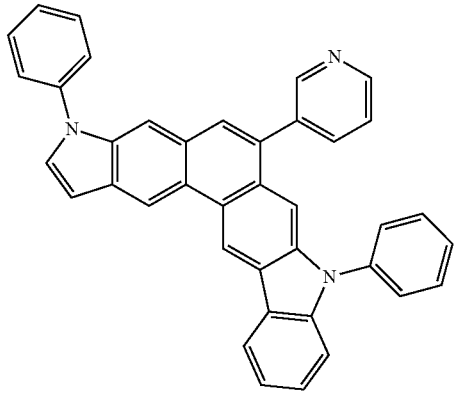
51-C -continued
51-D
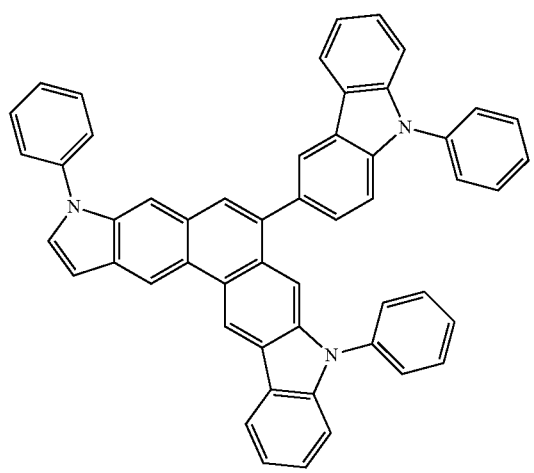
51-E
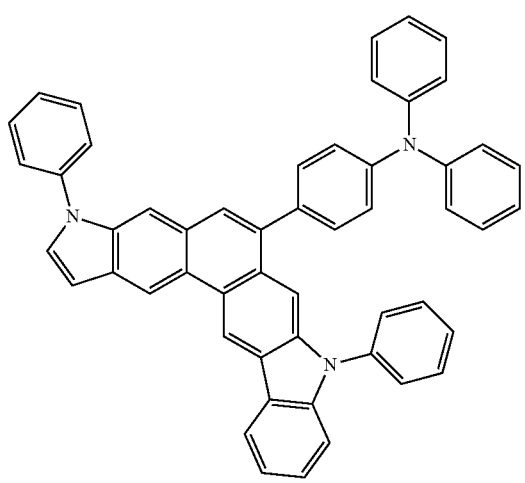
51-F
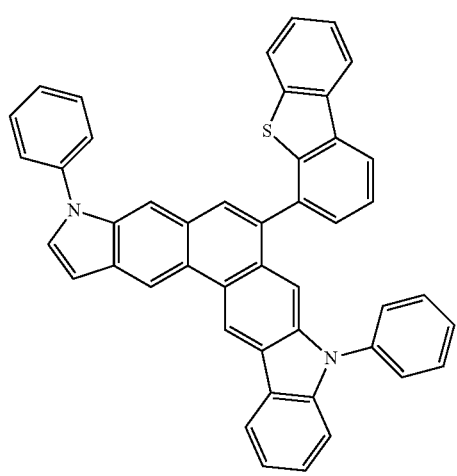
-continued
51-G
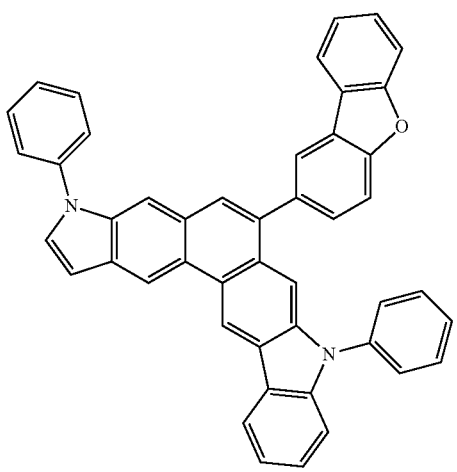
51-H
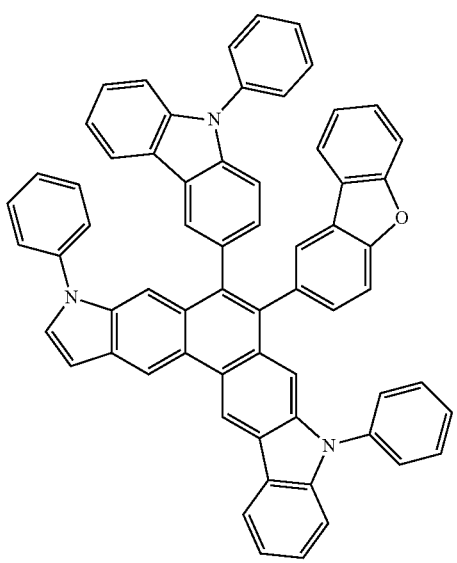
52-A
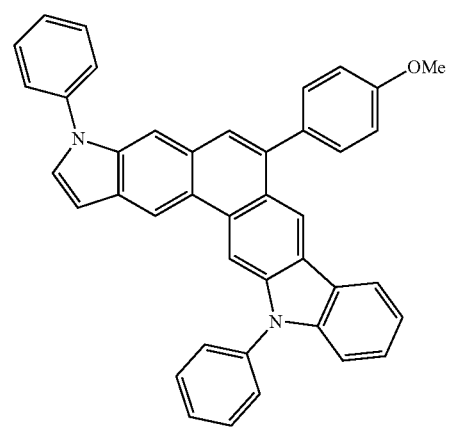

52-B
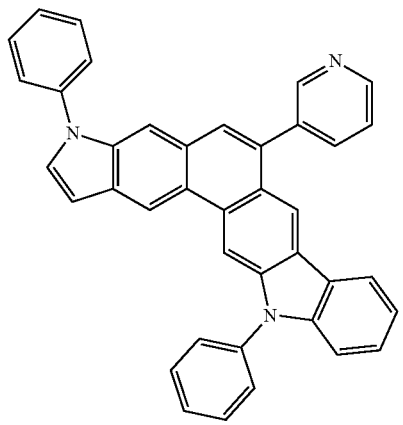
52-C
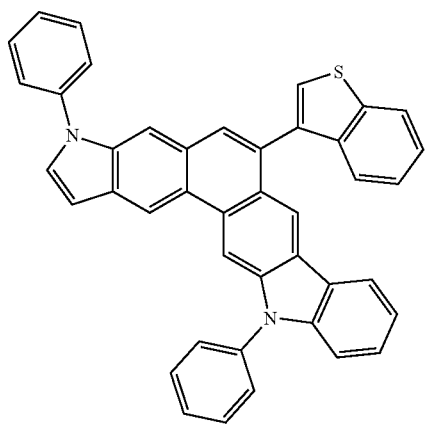
52-D
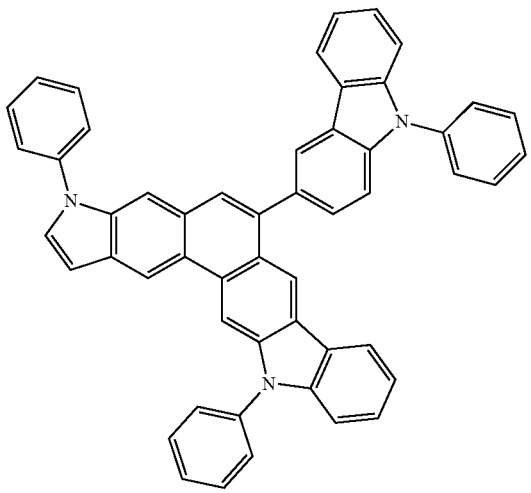
52-E
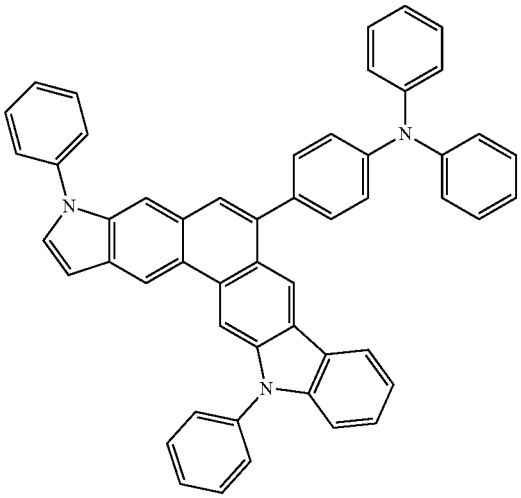
52-F
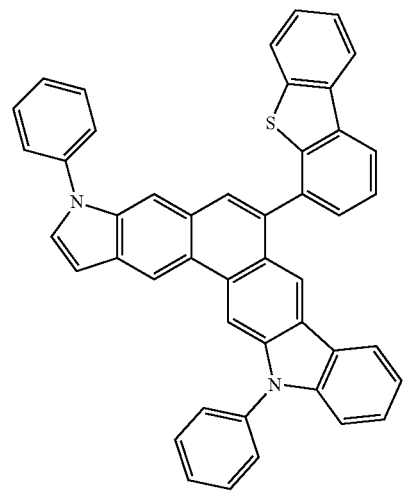
52-G
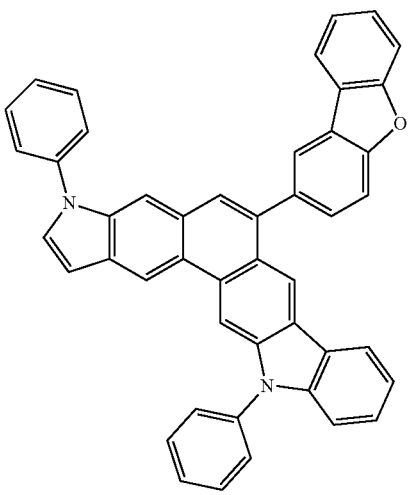

-continued
52-H
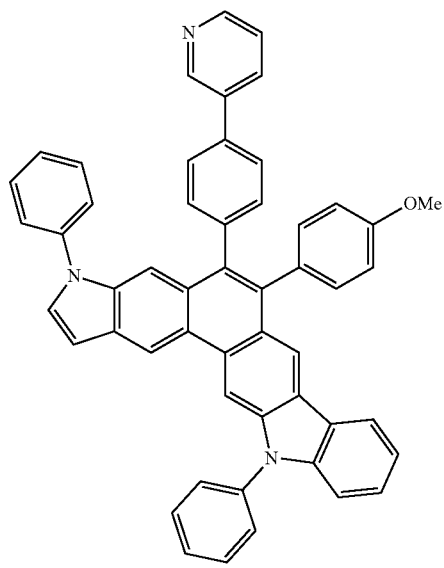
53-A
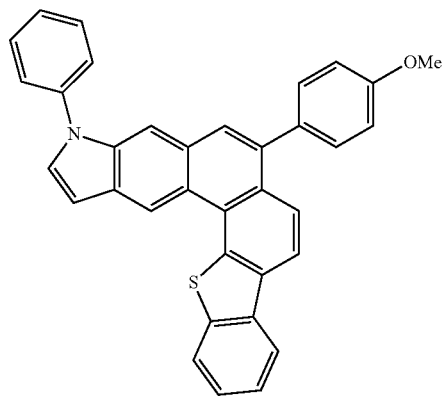
53-B
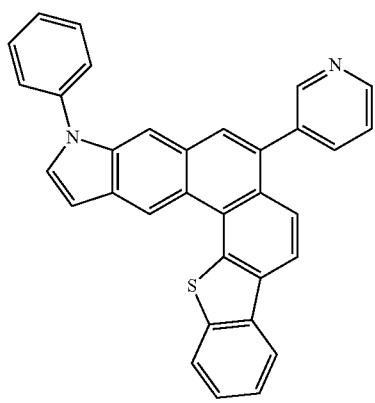
-continued
53-C
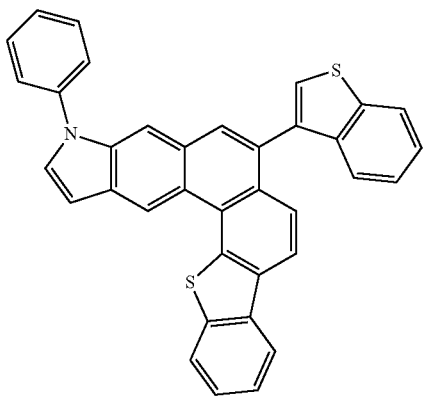
53-D
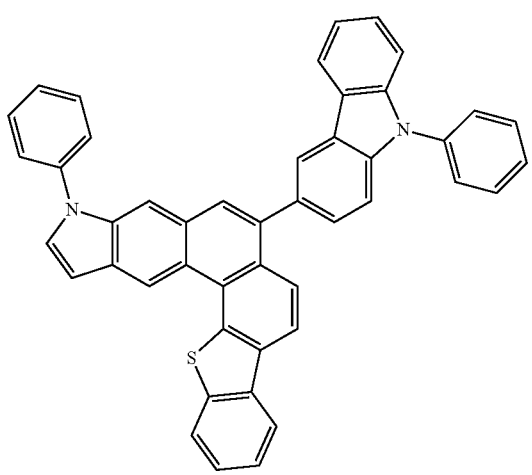
53-E
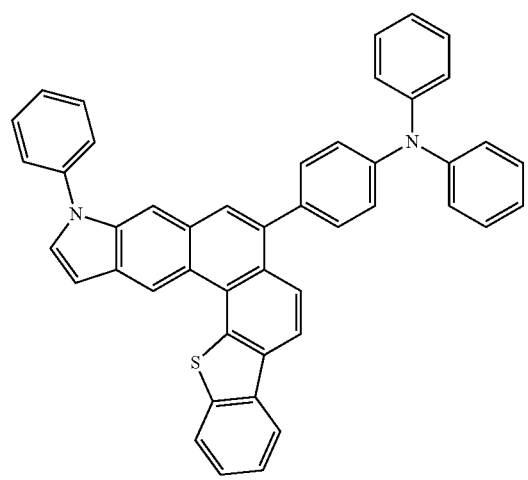

53-F
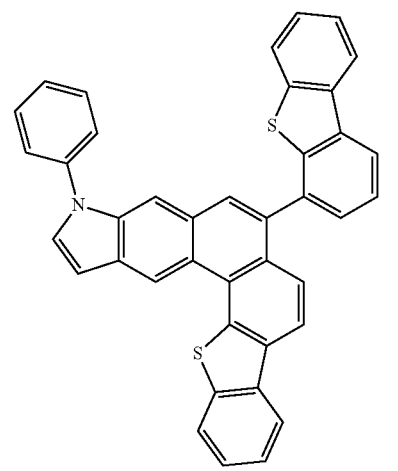
53-G
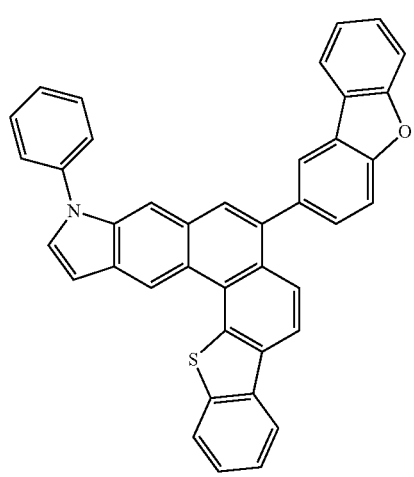
53-H
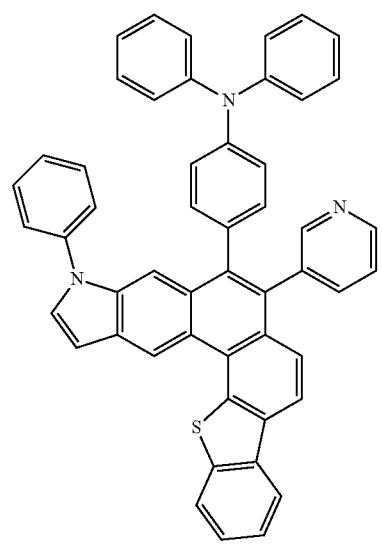
54-A
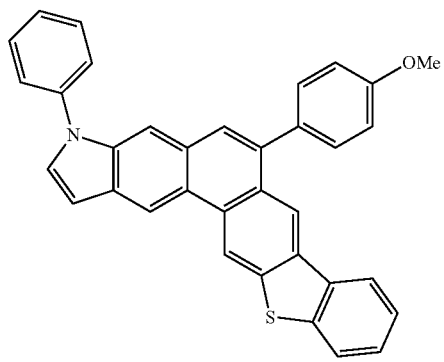
54-B
54-C
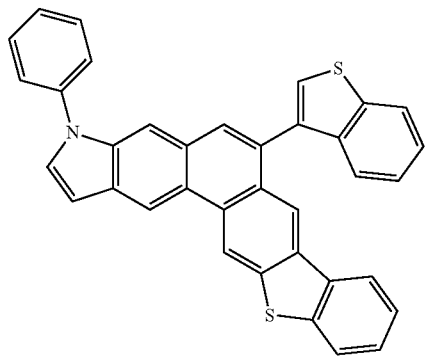
54-D 54-E
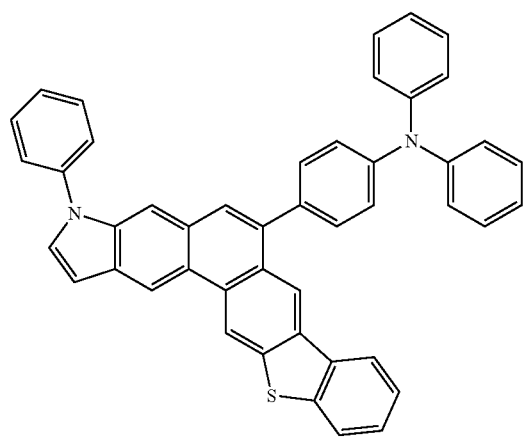
54-F
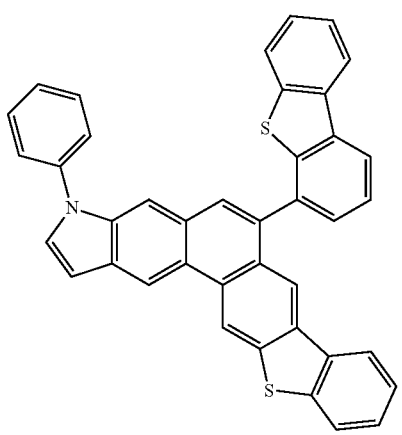
54-G
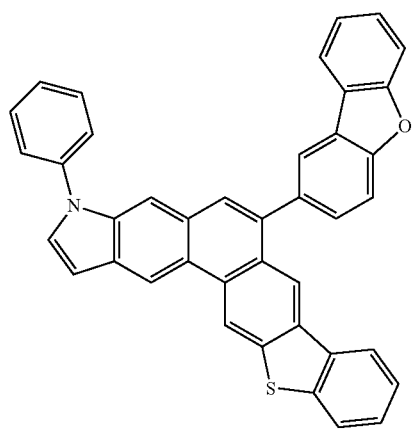
54-H
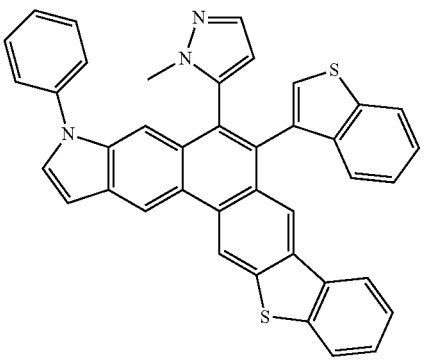
55-A
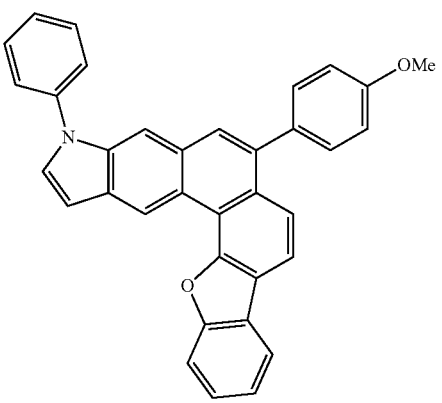
55-B
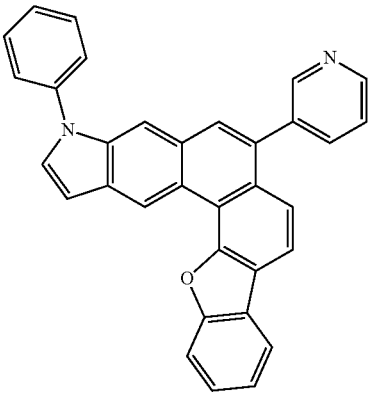
55-C
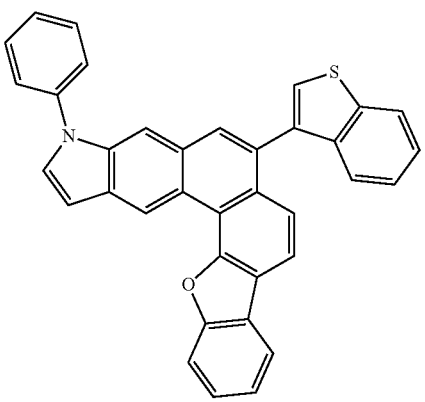

55-D
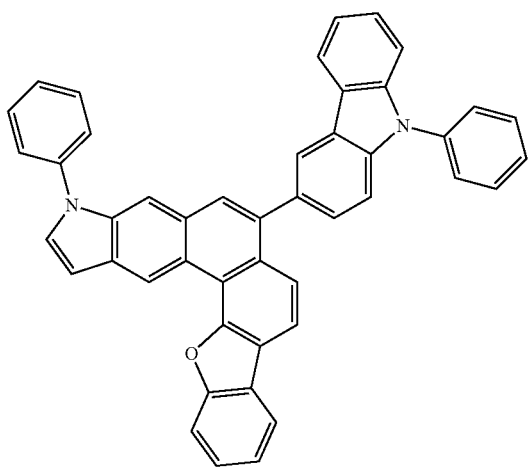
55-E
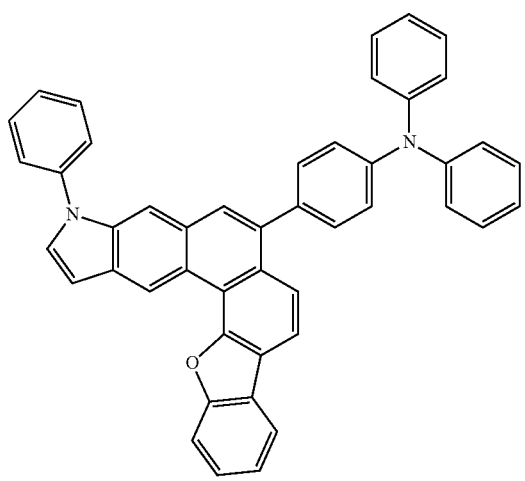
55-F
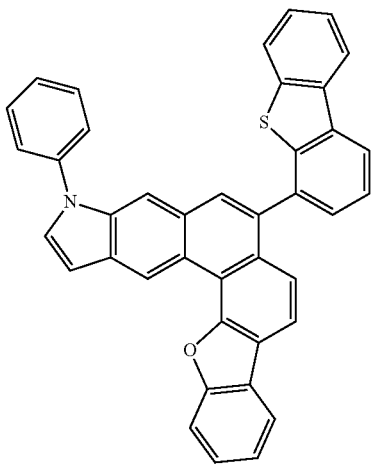
55-G
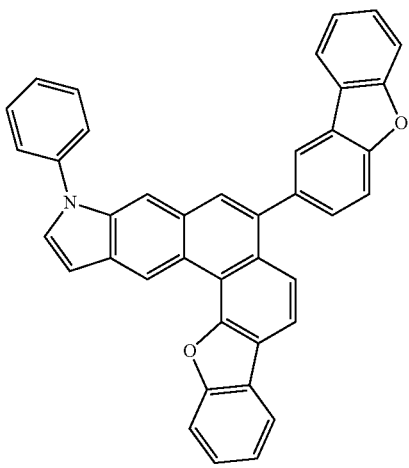
55-H
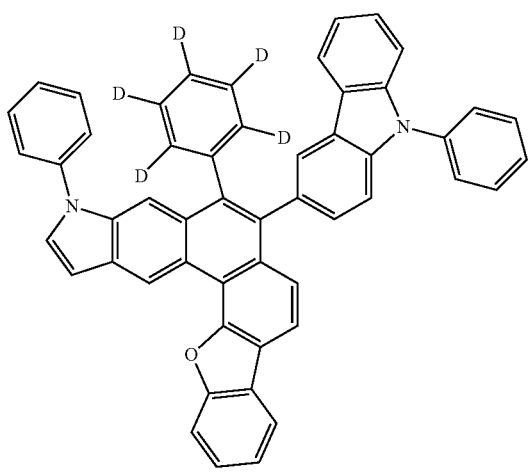
56-A
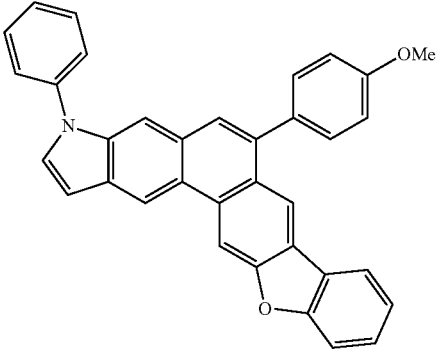

56-B
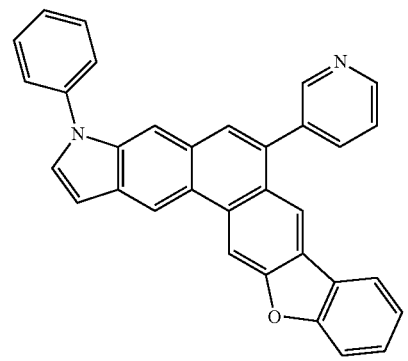
56-C
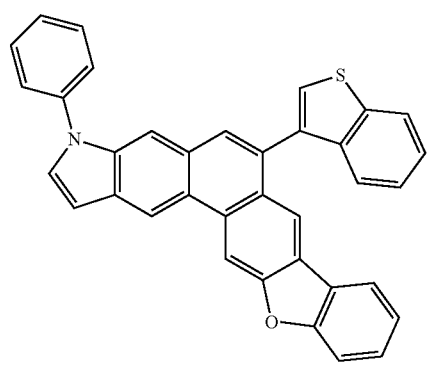
56-D
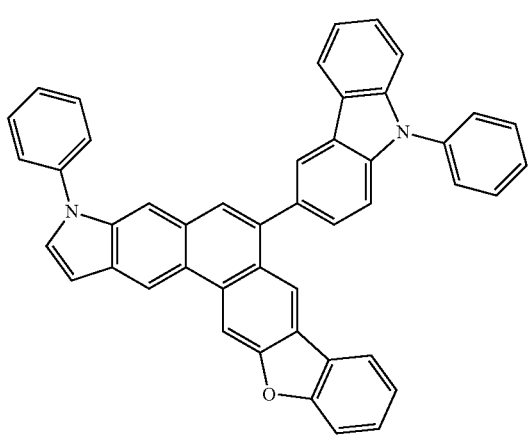
56-E
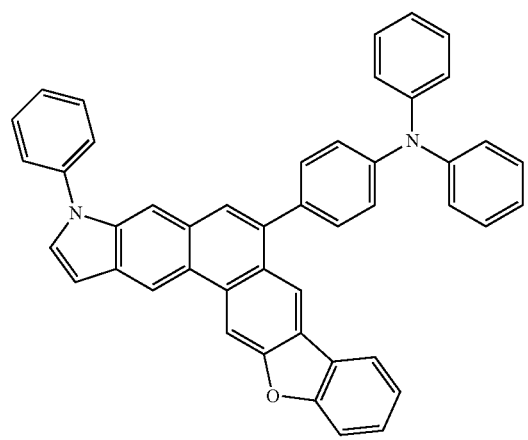
56-F
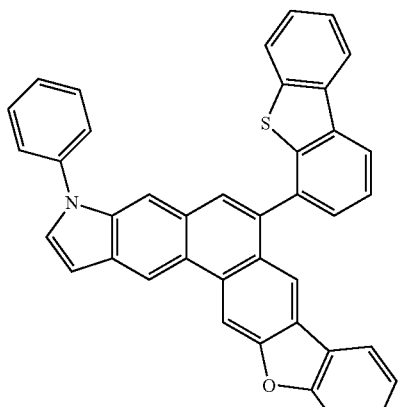
56-G
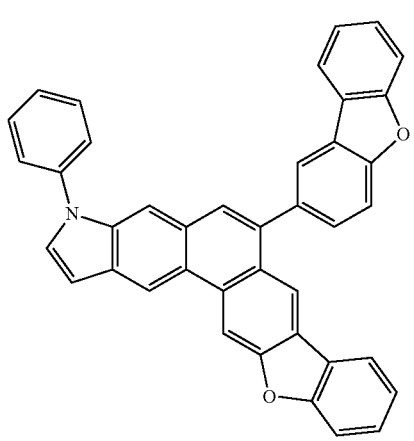
56-H
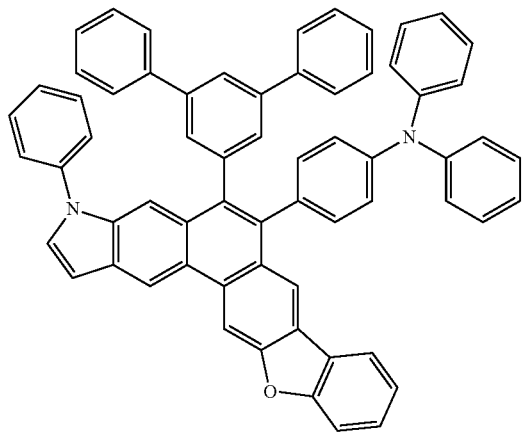
61-A
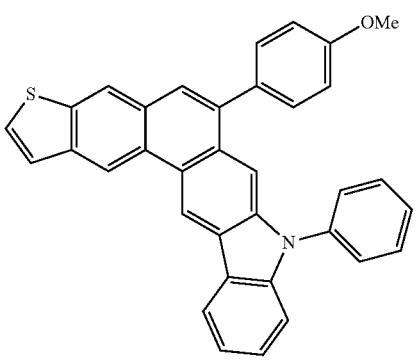

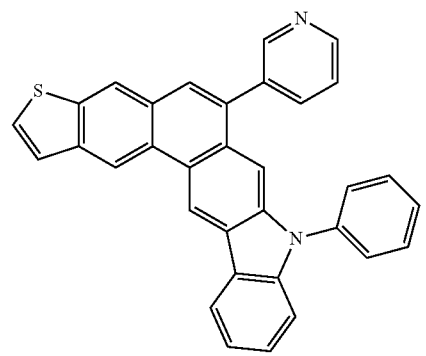
61-B
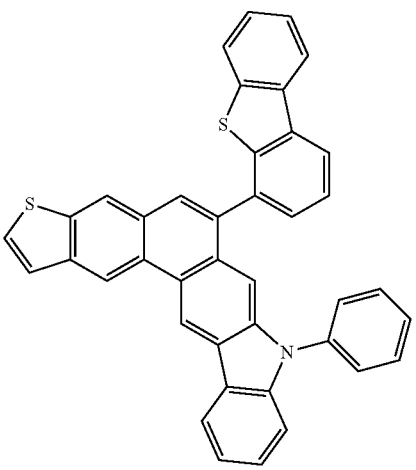
61-F
61-C
61-G
61-D
61-E
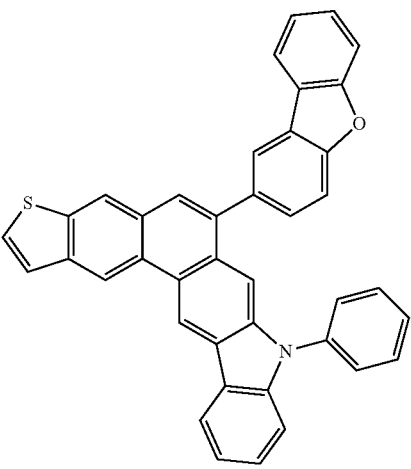
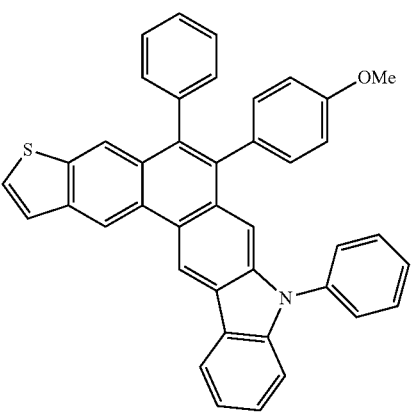
61-H 62-A
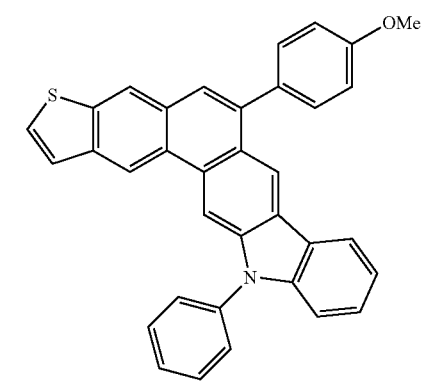
62-B
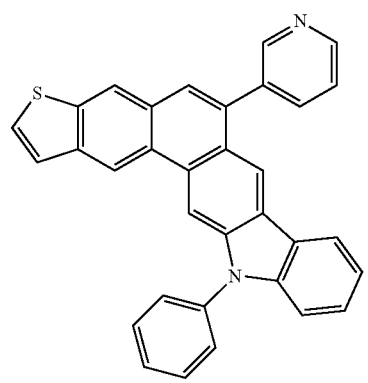
62-C
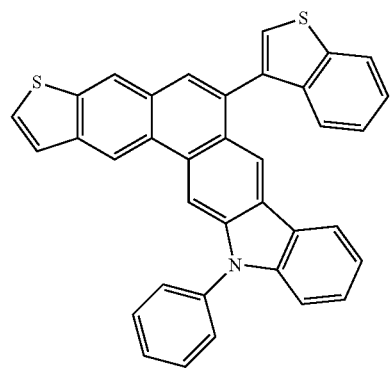
62-D
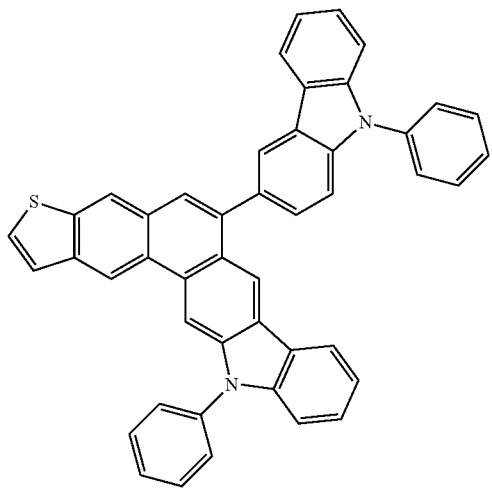
62-E
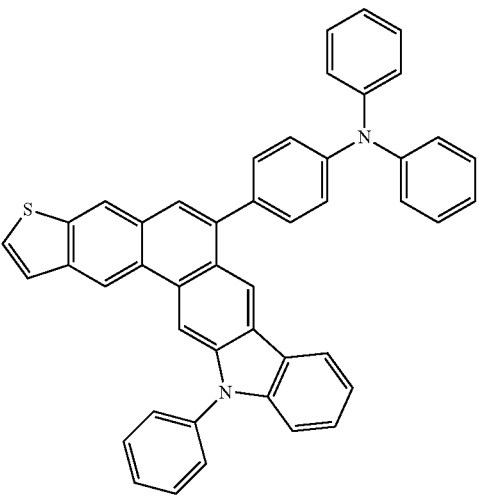
62-F
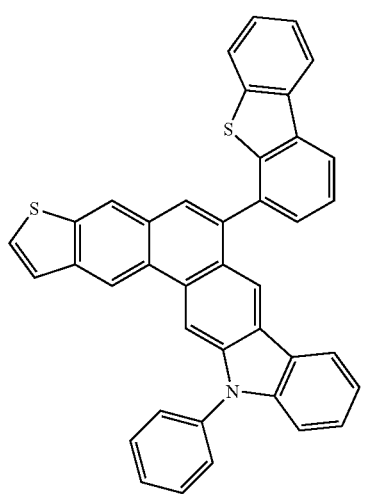
62-G
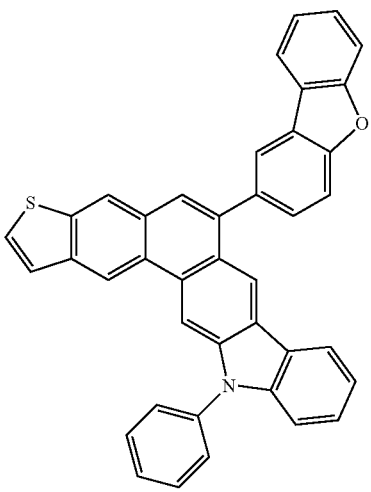

93
-continued
62-H
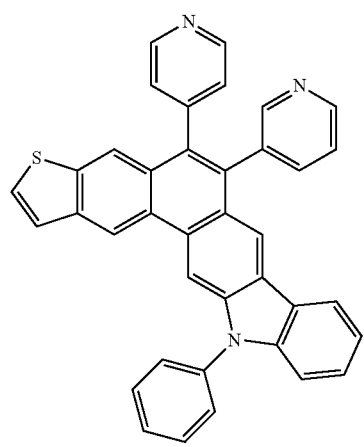
63-A
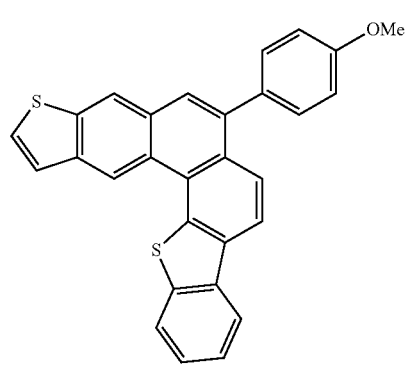
63-B
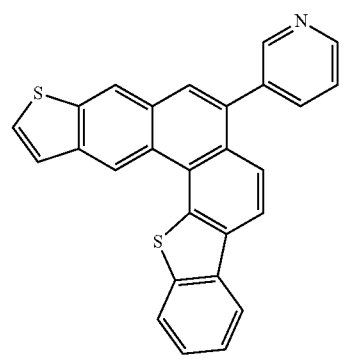
63-C
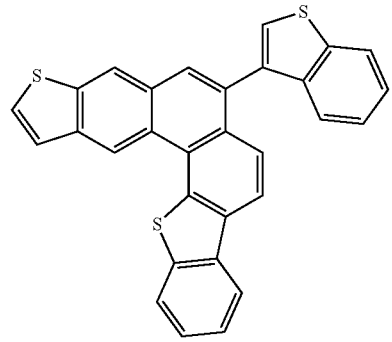
94
-continued
63-D
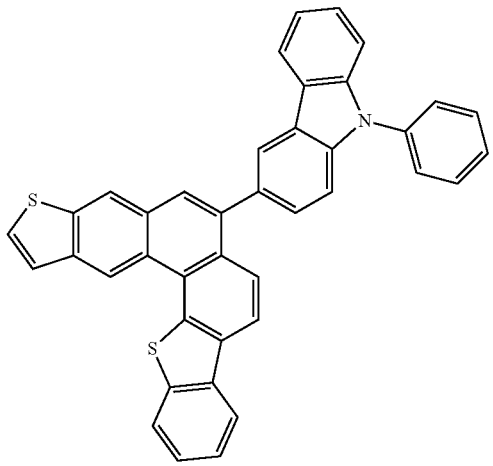
63-E
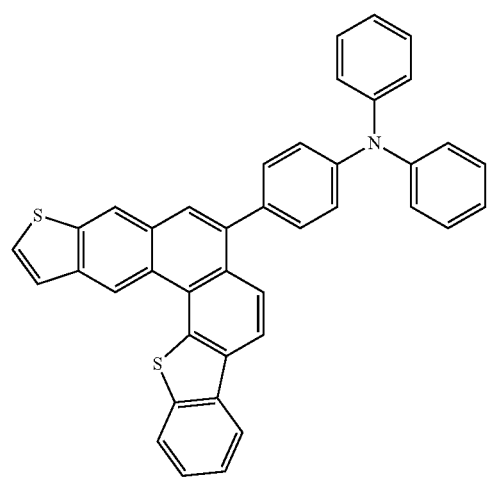
63-F
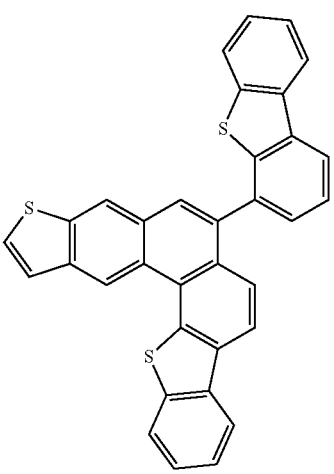

95
63-G
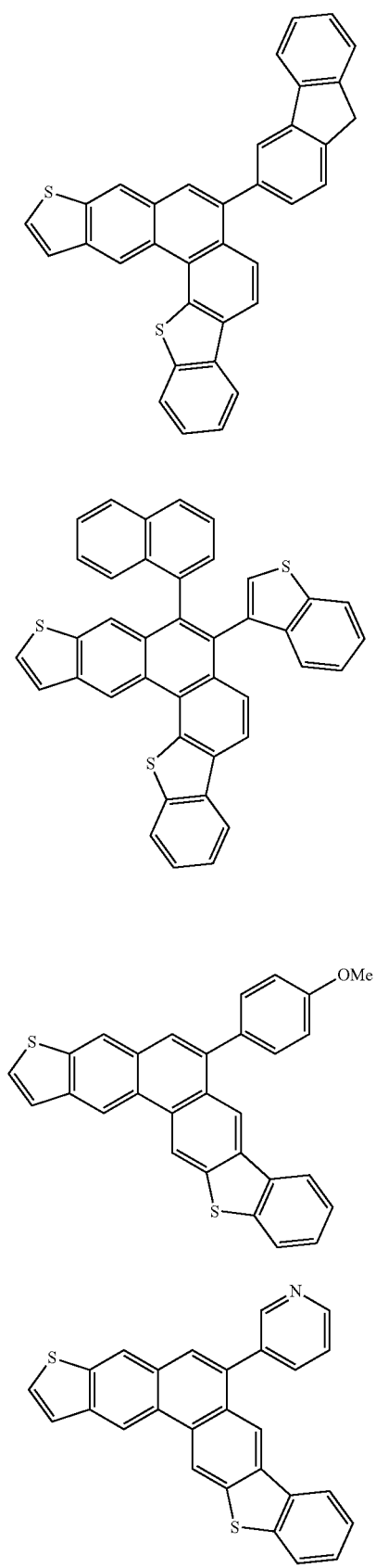
63-H
64-A
64-B
96
64-C
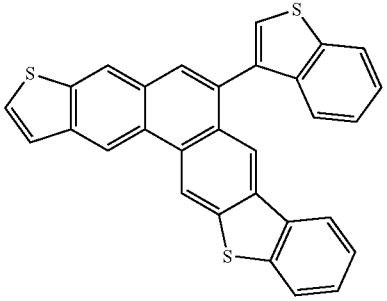
64-D
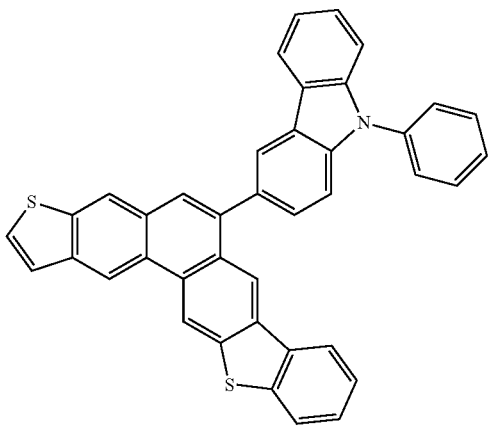
64-E
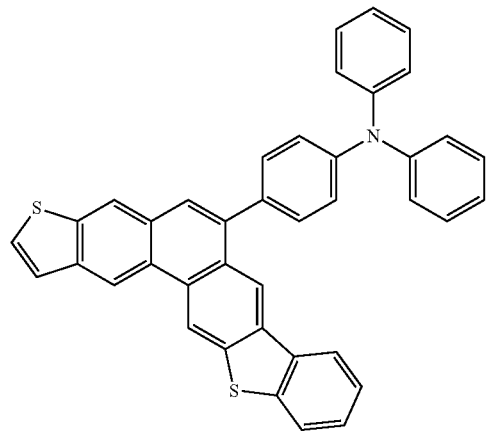
64-F
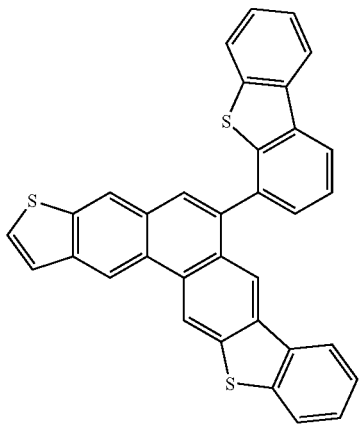

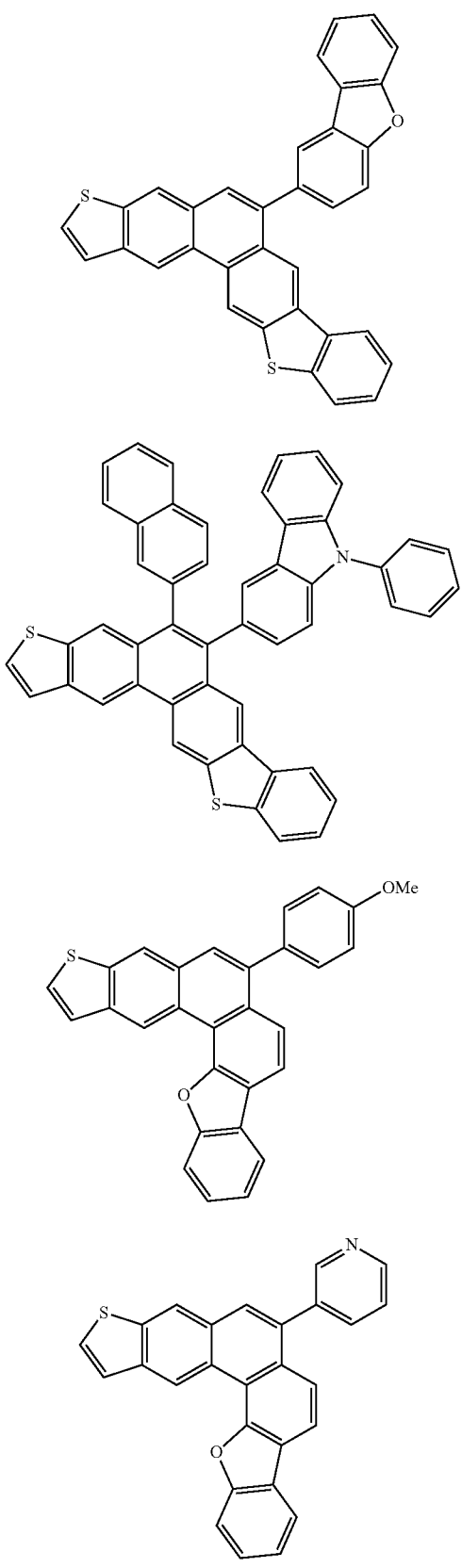
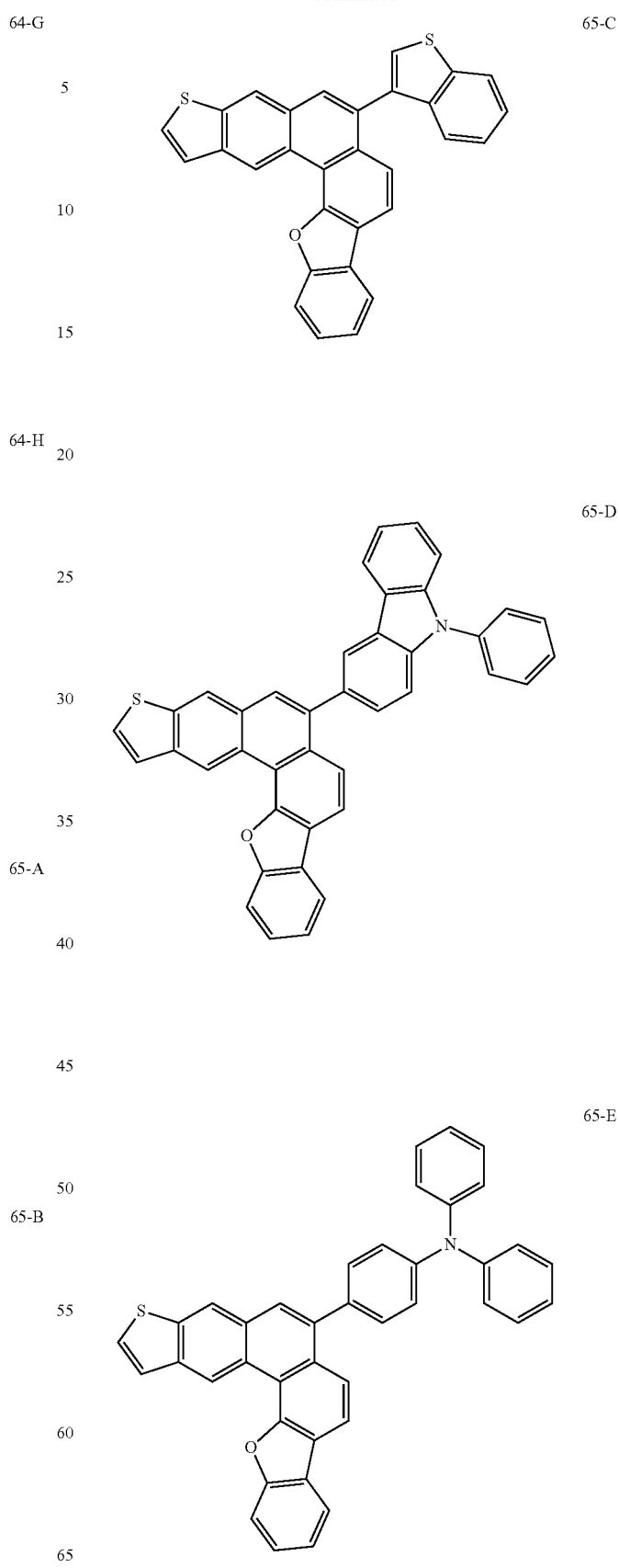

-continued
65-F
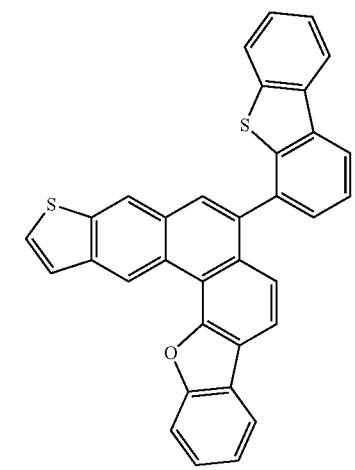
65-G
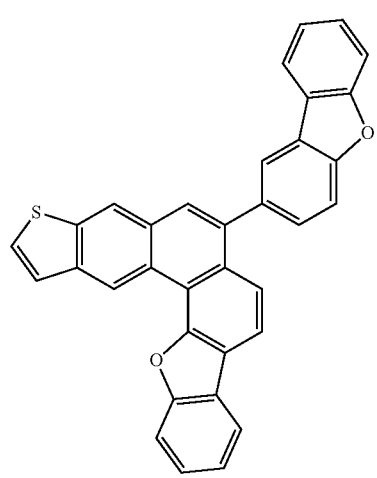
65-H
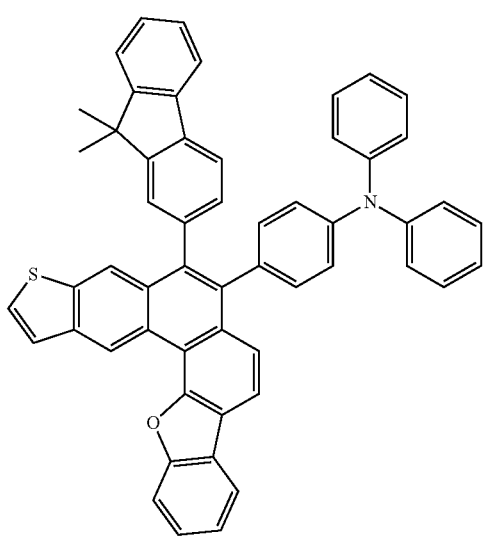
-continued
66-A
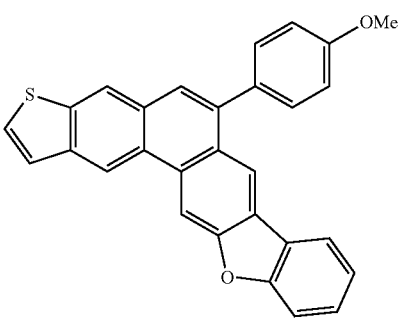
66-B
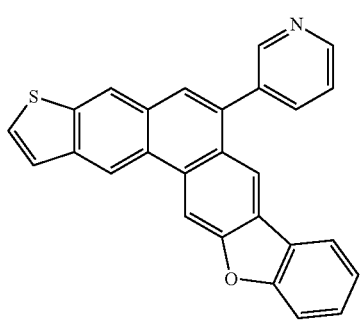
66-C
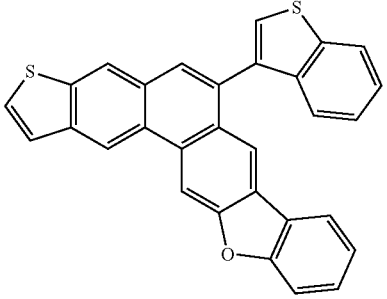
66-D
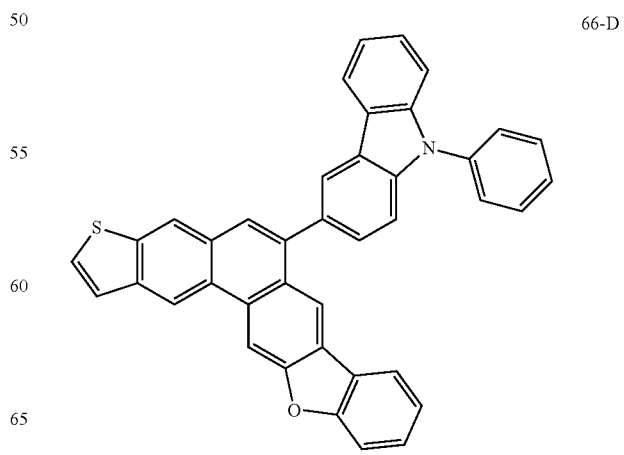

| 101 | 102 |
|---|---|
| -continued | -continued |
66-E
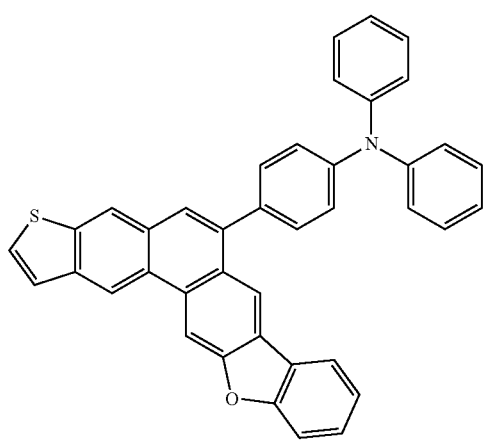
66-H
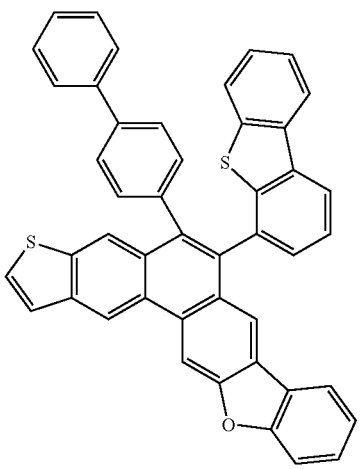
66-F
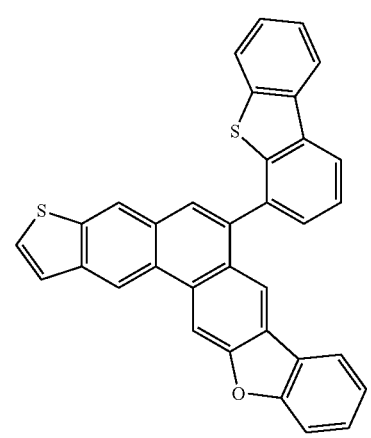
71-A
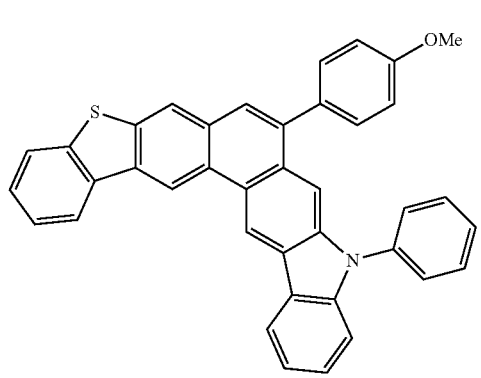
71-B
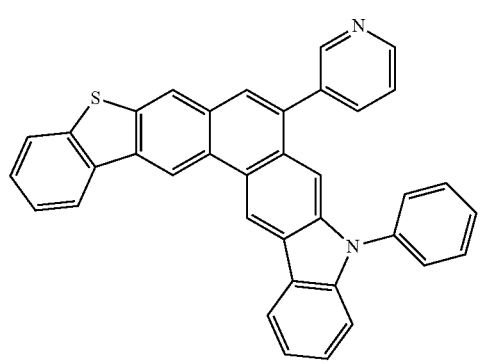
66-G
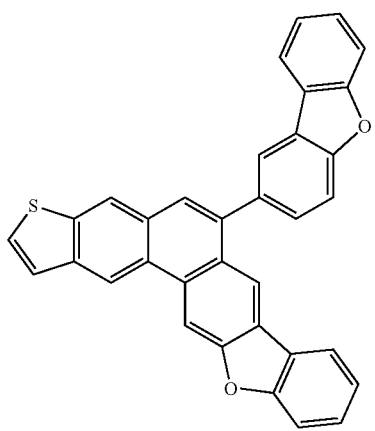
71-C
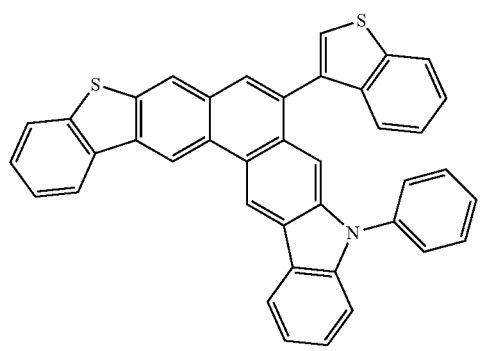

-continued
71-D
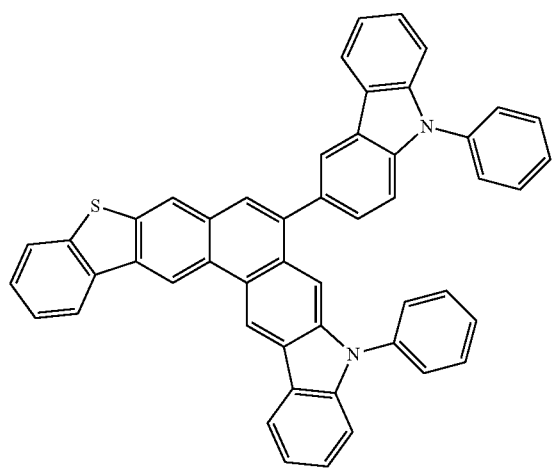
71-E
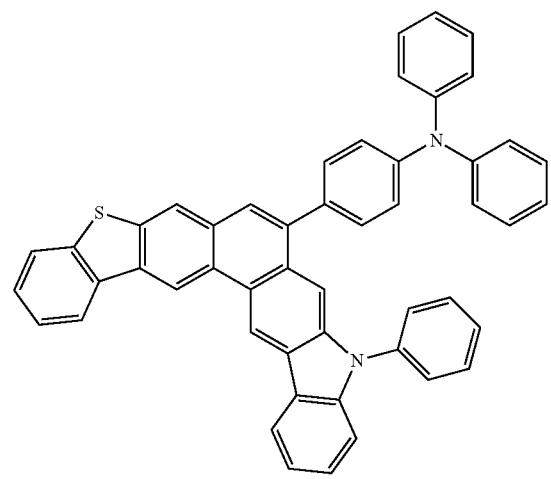
71-F
71-G
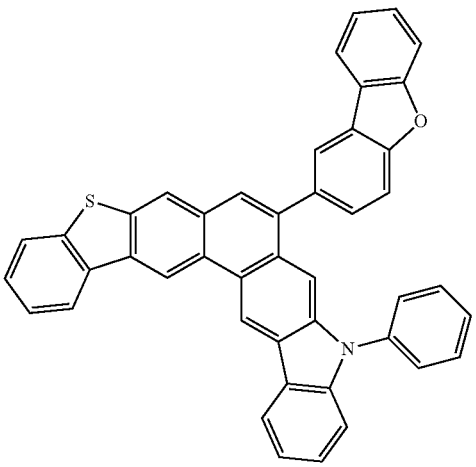
71-H
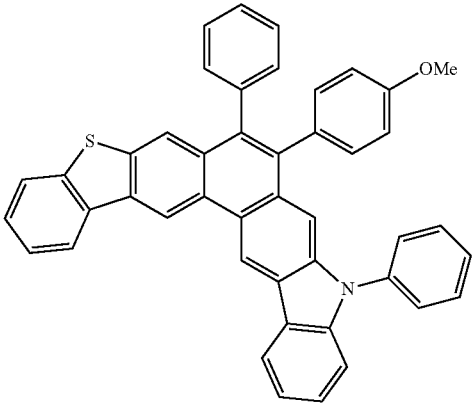
72-A
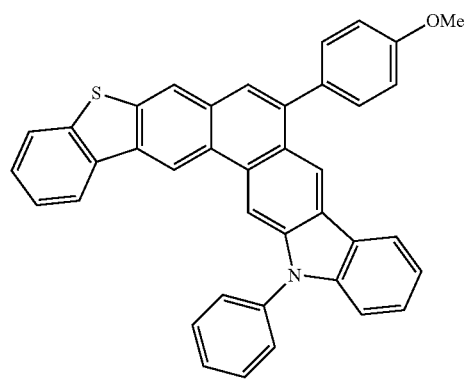
72-B
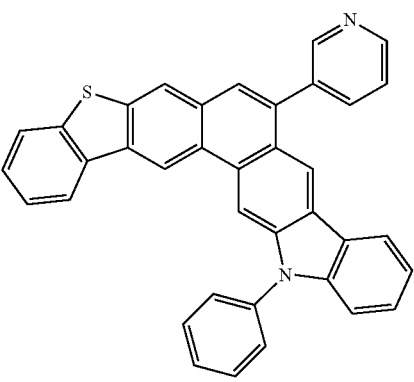

72-C
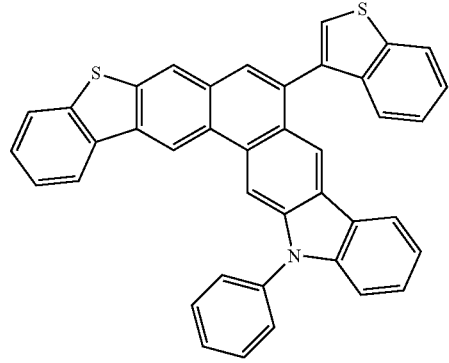
72-D
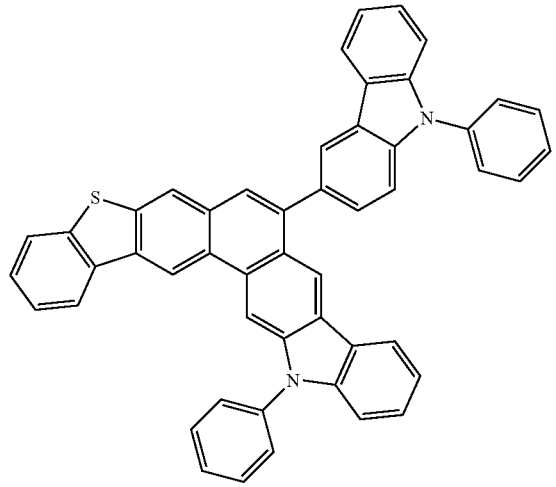
72-E
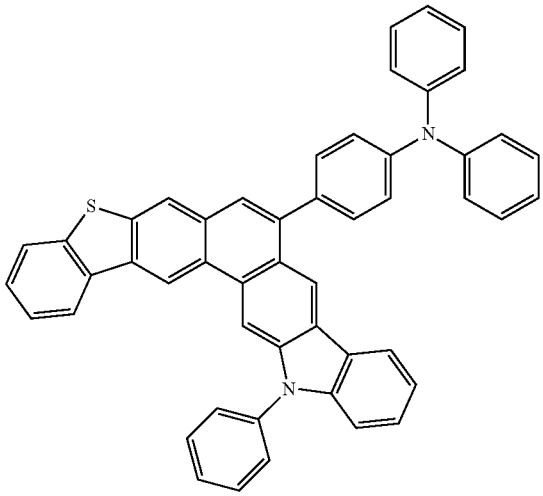
72-F
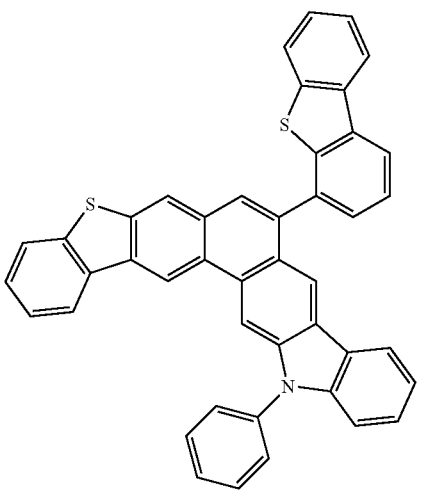
72-G
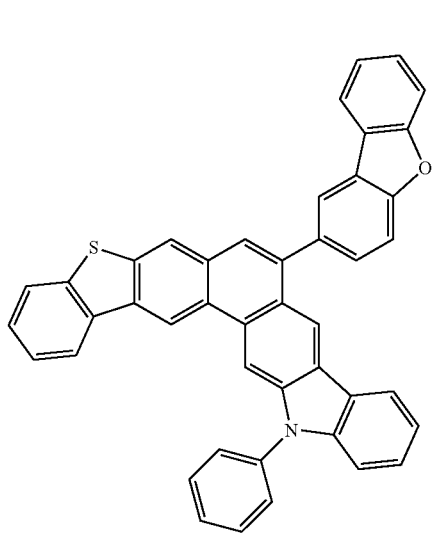
72-H
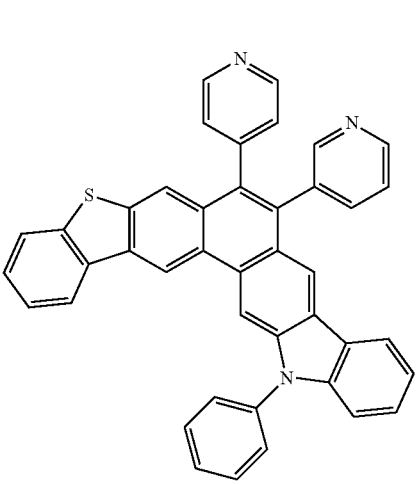

-continued
73-A
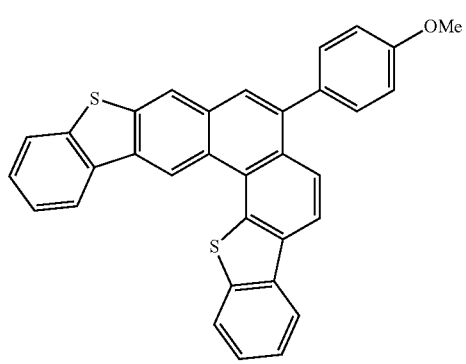
73-B
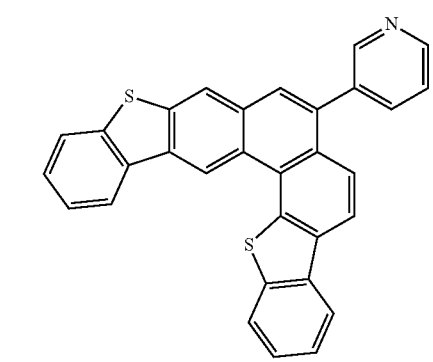
73-C
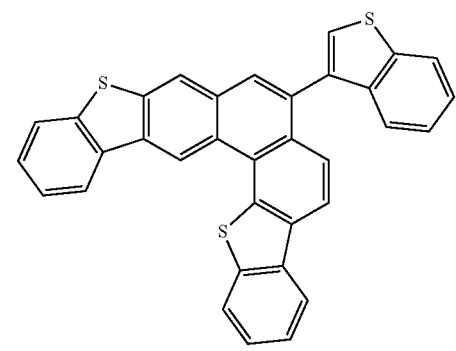
-continued
73-E
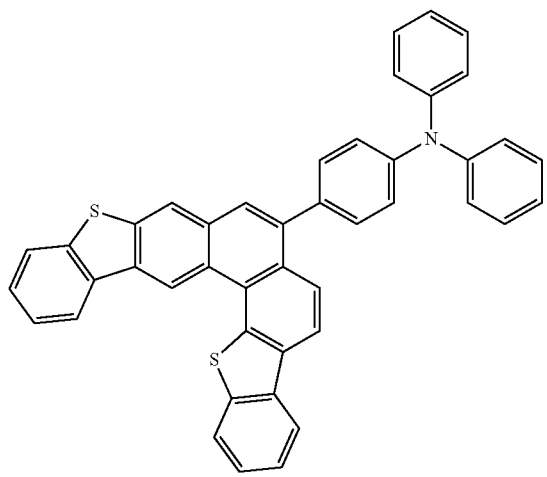
73-F
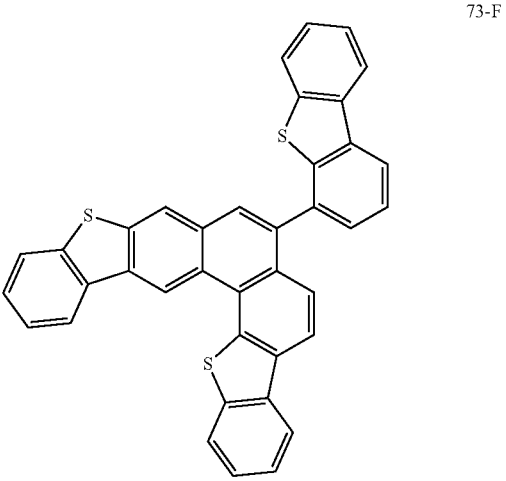
73-G
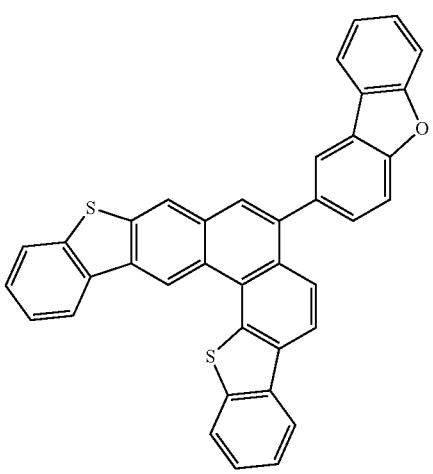
73-D 73-H
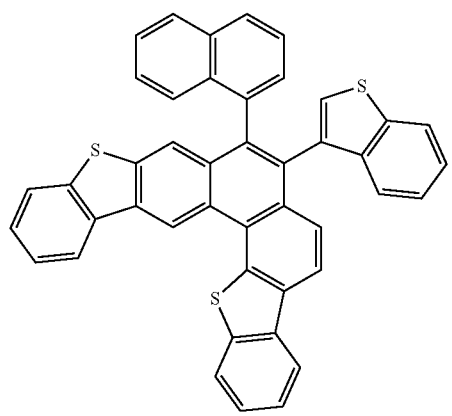
74-A
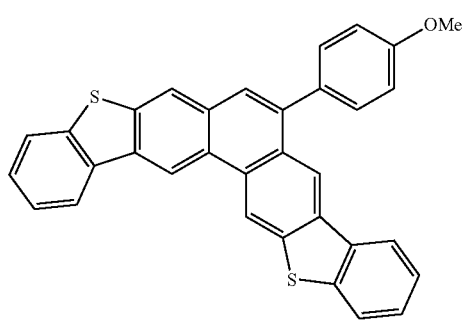
74-B
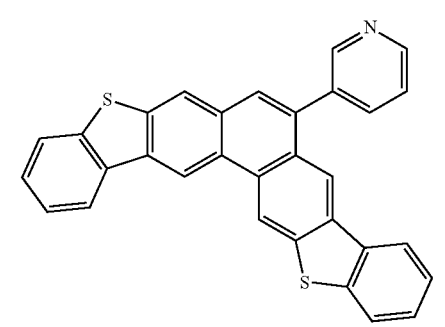
74-C
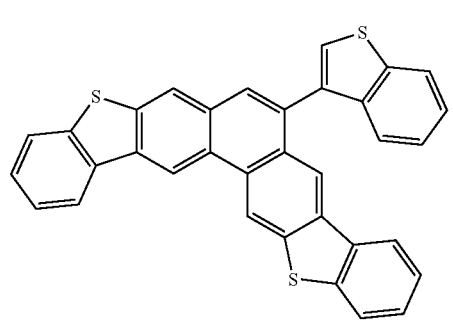
74-D
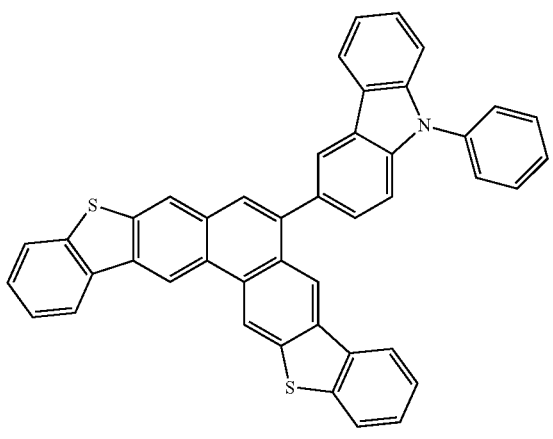
74-E
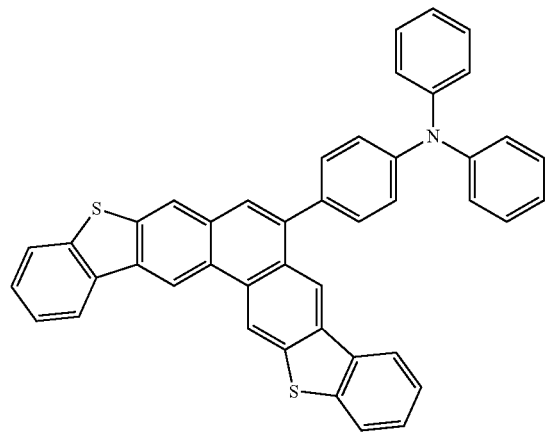
74-F
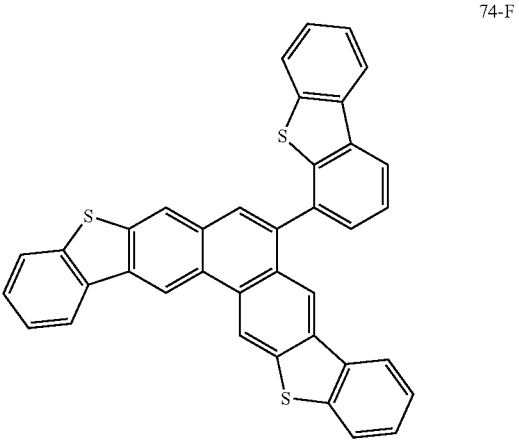

74-G
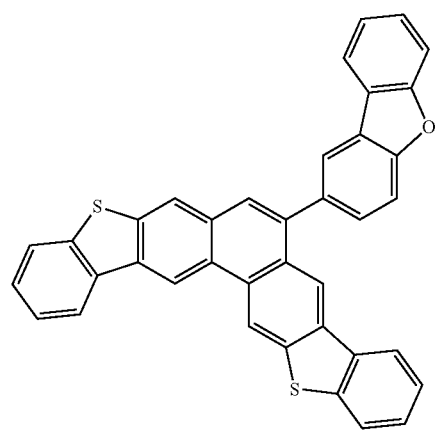
74-H
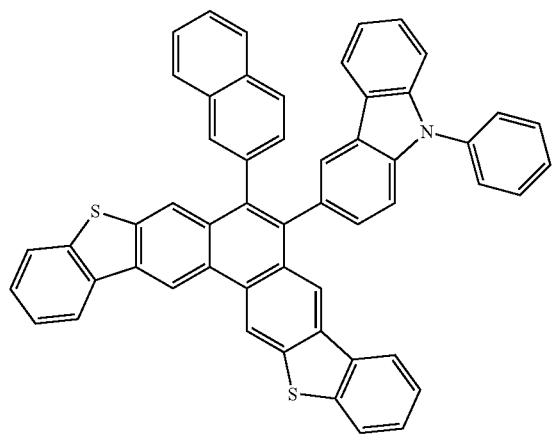
75-A
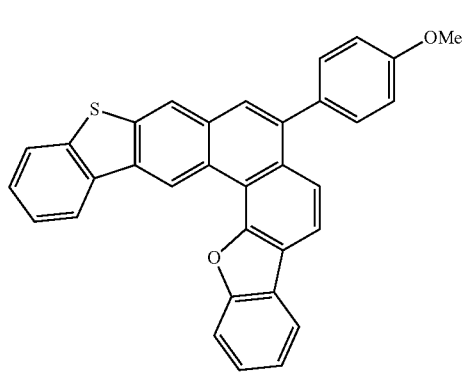
75-B
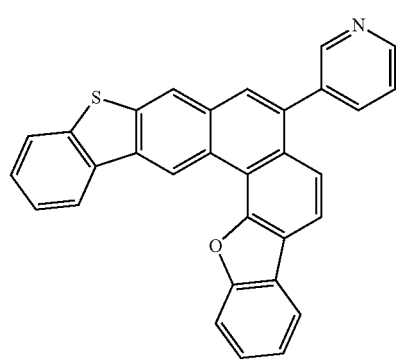
75-C
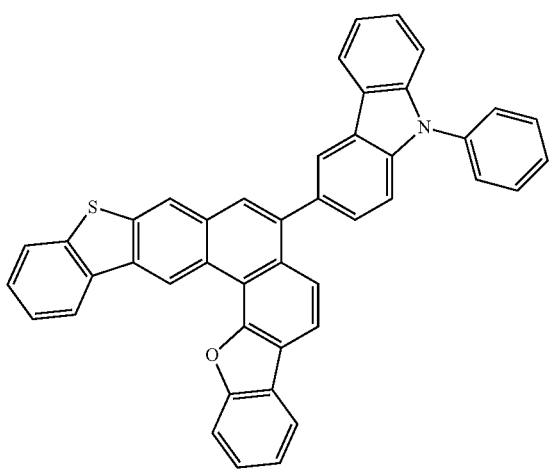
75-D
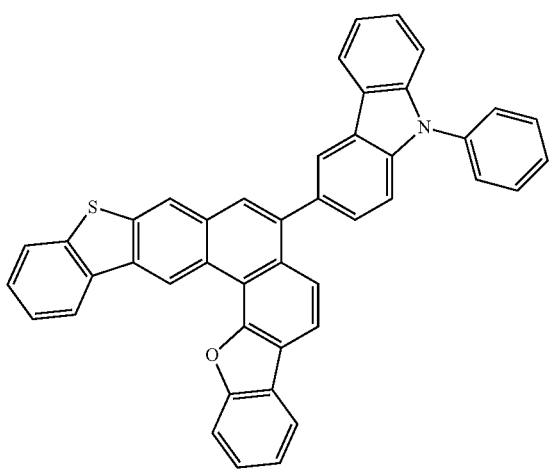
75-E
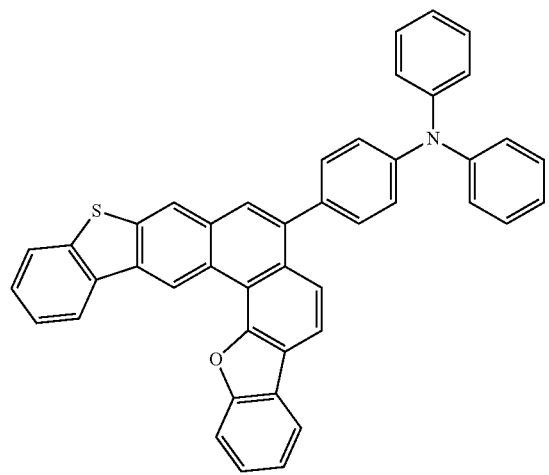

75-F
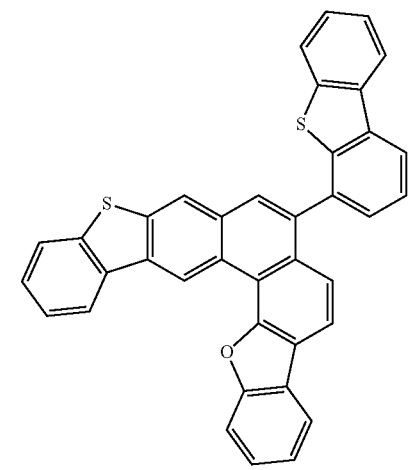
75-G
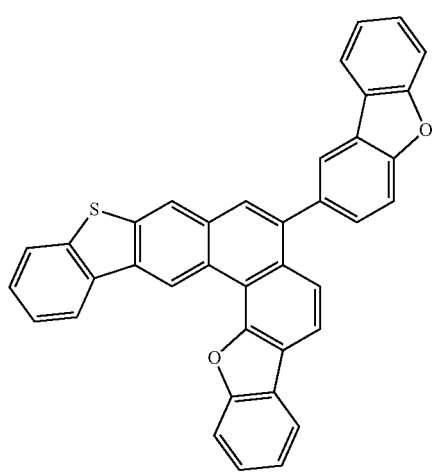
75-H
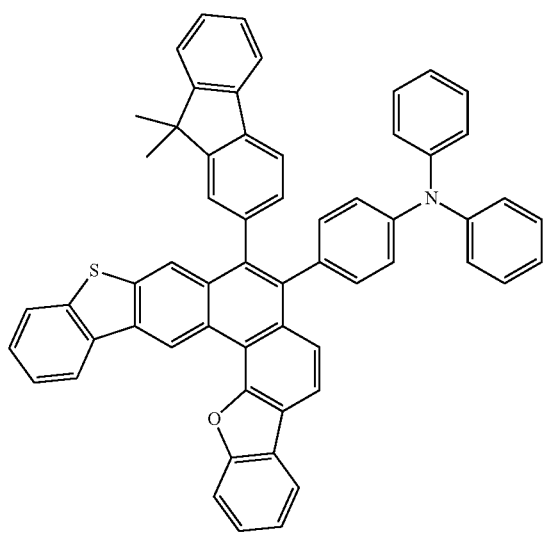
76-A
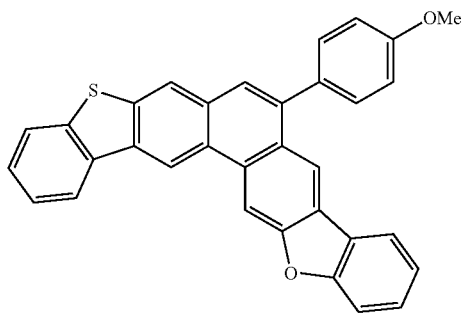
76-B
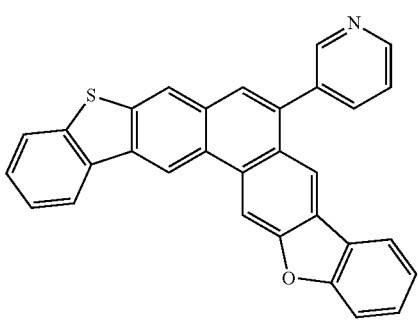
76-C
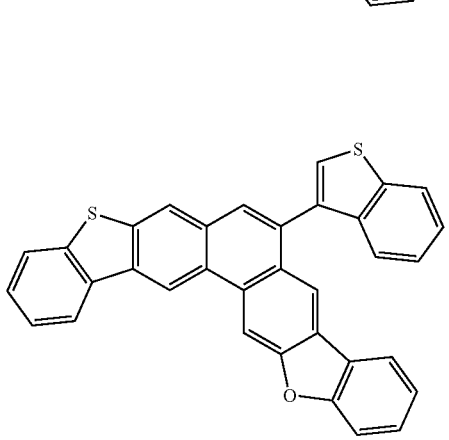
76-D
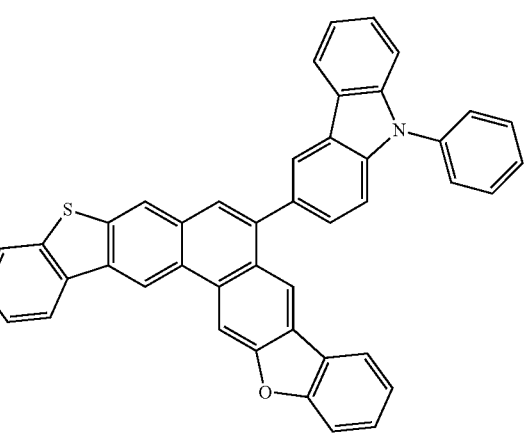

76-E

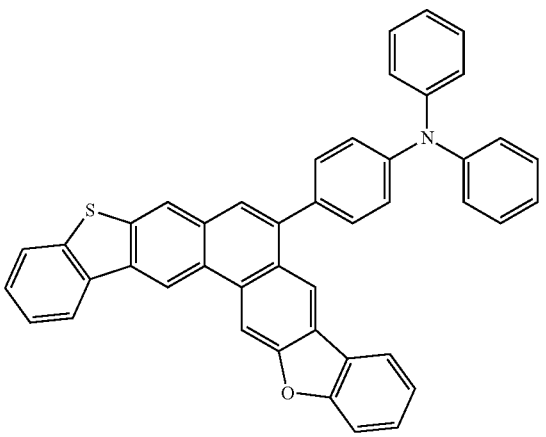

76-F

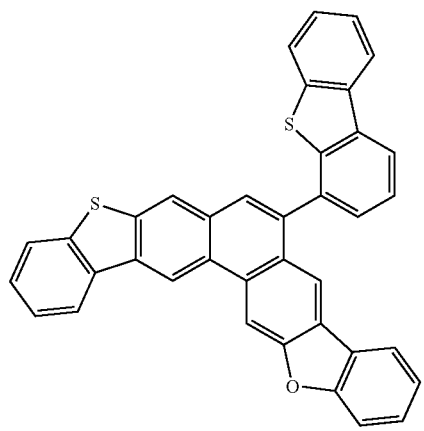

76-G

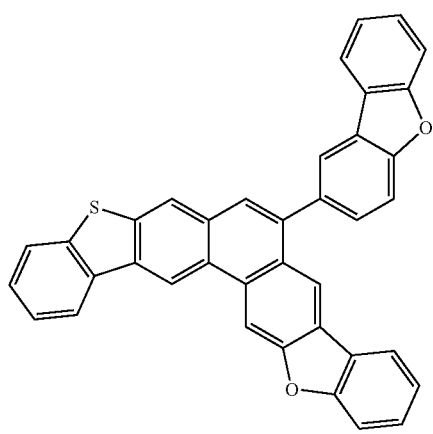

76-H

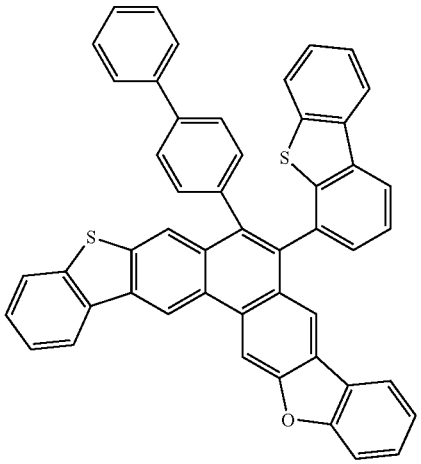

In another embodiment of the present invention, there is provided an organic light-emitting device including a first electrode, a second electrode, and an organic film disposed between the first electrode and the second electrode, the organic film comprising at least one of the compounds according to Formulae 1 to 4 described above.

The organic layer can include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

In some embodiments, the organic layer can be an emission layer, for example, a blue emission layer, a green emission layer, or a hole transport layer. The compound can be used as a fluorescent host, a phosphorescent host, or a fluorescent dopant.

In some embodiments, the organic light-emitting device can include an emission layer, a hole injection layer, a hole transport layer, or a functional layer having both hole injection and hole transport capabilities. The emission layer, the hole injection layer, the hole transport layer, or the functional layer having both hole injection and hole transport capabilities can comprise at least one of the heterocyclic compounds according to Formulae 1 to 4 above. The emission layer can further include an anthracene-based compound, an arylamine-based compound, or a styryl-based compound.

In some other embodiments, the organic light-emitting device can include an emission layer, a hole injection layer, a hole transport layer, or a functional layer having both hole injection and hole transport capabilities. The emission layer, the hole injection layer, the hole transport layer, or the functional layer having both hole injection and hole transport capabilities can comprise at least one of the heterocyclic compounds according to Formulae 1 to 4 above. At least one of a red emission layer, a green emission layer, a blue emission layer, and a white emission layer of the emission layer can include a phosphorescent compound, and at least one of the hole injection layer, the hole transport layer, and the functional layer having both hole injection and hole transport capabilities can include a charge-generating material. In some embodiments, the charge-generating material can be a p-type dopant, and the p-type dopant can be a quinine derivative, a metal oxide or a cyano group-containing compound.

In some embodiments, the organic film can include an electron transport layer, and the electron transport layer can include an electron-transporting organic compound and a metal complex. The metal complex can be a lithium (Li) complex.

The term "organic layer" as used herein refers to a single layer and/or a plurality of layers disposed between the first and second electrodes of the organic light-emitting device.

The organic film can include an emission layer, and the emission layer can include at least one of the compounds of Formulae 1 described above. The organic film can include at least one of a hole injection layer, a hole transport layer, and a functional layer having both hole injection and hole transport capabilities (hereinafter, "H-functional layer"); and at least one of the hole injection layer, the hole transport layer, and the functional layer having both hole injection and hole transport capabilities may include at least one of the compounds of Formula 1.

The heterocyclic compounds of Formulae 1 to 4 in the emission layer may serve as a fluorescent dopant or a phosphorescent host. For example, the heterocyclic compounds of Formulae 1 to 4 may serve as a blue fluorescent dopant emitting blue light. The heterocyclic compounds of Formulae 1 to 4 in the emission layer may serve as a fluorescent or phosphorescent host emitting red light, green light, or blue light.

FIG. 1 is a schematic sectional view of an organic light-emitting device according to an embodiment of the present invention. Hereinafter, a structure of an organic light-emitting device according to an embodiment of the present invention and a method of manufacturing the same will now be described with reference to FIG. 1.

A substrate (not shown) can be any substrate that is used in existing organic light-emitting devices. In some embodiments, the substrate 11 can be a glass substrate or a transparent plastic substrate with strong mechanical strength, thermal stability, transparency, surface smoothness, ease of handling and water resistance.

The first electrode can be formed by depositing or sputtering a first electrode-forming material on the substrate. When the first electrode constitutes an anode, a material having a high work function can be used as the first electrode-forming material to facilitate hole injection. The first electrode can be a reflective electrode or a transparent electrode. Suitable first electrode-forming materials include transparent and conductive materials such as indium tin oxide (ITO), indium zinc oxide (IZO), $SnO_2$, and ZnO. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode can have a single-layer structure or a multi-layer structure including at least two layers. For example, the first electrode can have a three-layered structure of ITO/Ag/ITO, but is not limited thereto.

An organic layer(s) is formed on the first electrode.

The organic layer can include a hole injection layer (HIL), a hole transport layer (HTL), a buffer layer (not shown), an emission layer (EML), an electron transport layer (ETL), or an electron injection layer (EIL).

The HIL may be formed on the first electrode by vacuum deposition, spin coating, casting, Langmuir-Blodgett (LB) deposition, or the like.

When the HIL is formed using vacuum deposition, vacuum deposition conditions can vary according to the compound that is used to form the HIL and the desired structure and thermal properties of the HIL to be formed. For example, vacuum deposition can be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions can vary according to the compound that is used to form the HIL and the desired structure and thermal properties of the HIL to be formed. For example, the coating rate can be in the range of about 2000 rpm to about 5000 rpm, and a temperature at which heat treatment is performed to remove a solvent after coating can be in the range of about 80° C. to about 200° C. However, the coating conditions are not limited thereto.

The HIL can be formed of any material that is commonly used to form a HIL. Non-limiting examples of the material that can be used to form the HIL are N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 4,4',4"-tris(N-(2-naphthyl)-N-phenylamino)triphenylamine (2-TNATA), polyaniline/dodecylbenzenesulfonic acid (Pani/DESA), poly(3,4-ethylenedioxythiophene)/poly(4-styrenesulfonate)(PEDOT/PSS), and polyaniline/camphor sulfonic acid (Pani/CSA) and polyaniline)/poly(4-styrenesulfonate (PANI/PSS).

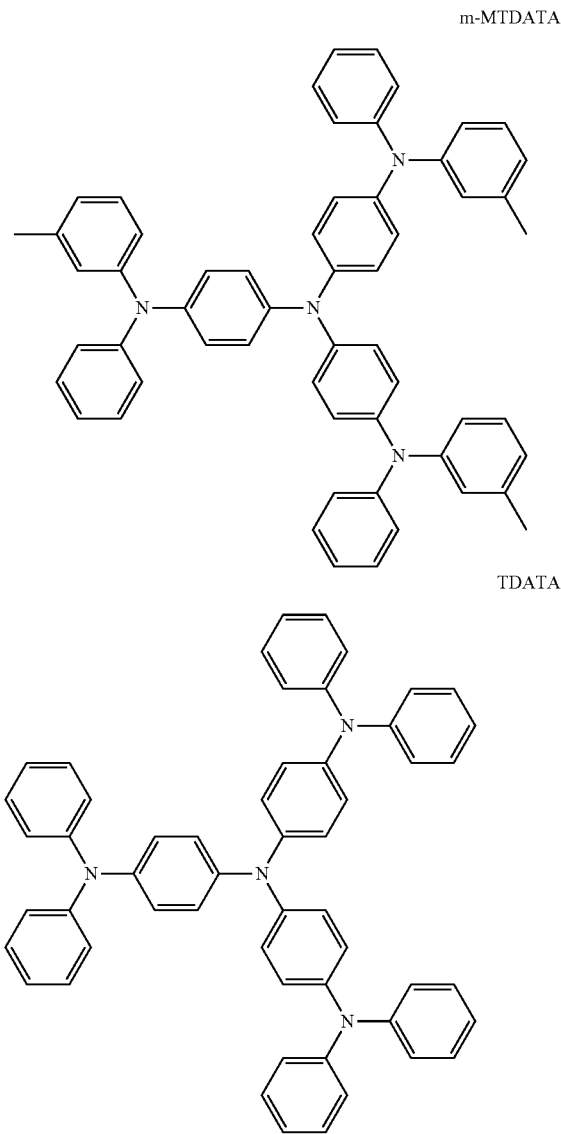

2-TNATA

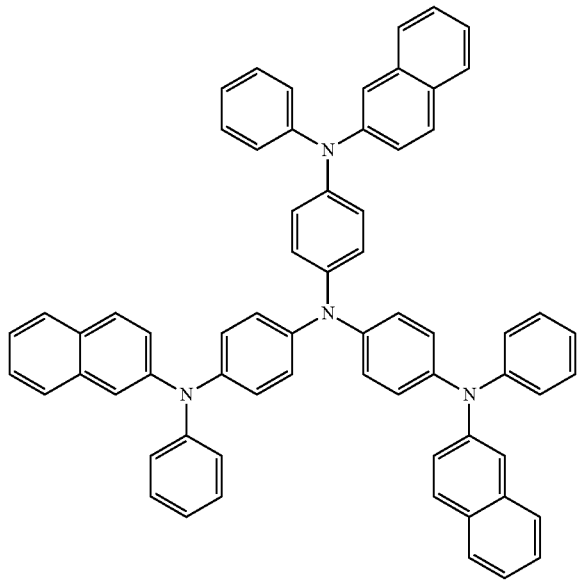

The thickness of the HIL may be about 100 Å to about 10000 Å, and in some embodiments, can be from about 100 Å to about 1000 Å. When the thickness of the HIL is within these ranges, the HIL can have good hole injecting ability without a driving voltage that is too high to be of economical use.

Then, a HTL can be formed on the HIL by using vacuum deposition, spin coating, casting, Langmuir-Blodgett (LB) deposition, or the like. When the HTL is formed using vacuum deposition or spin coating, the conditions for deposition and coating can be similar to those for the formation of the HIL, though the conditions for the deposition and coating can vary according to the material that is used to form the HTL.

The HTL can be formed of any of the heterocyclic compounds of Formulae 1 to 4 or any known hole transporting materials. Non-limiting examples of suitable known HTL forming materials are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4', 4"-tris(N-carbazolyl)triphenylamine (TCTA), and N,N'-di(1-naphthyl)-N,N'-diphenylbenzidine) (NPB).

TPD

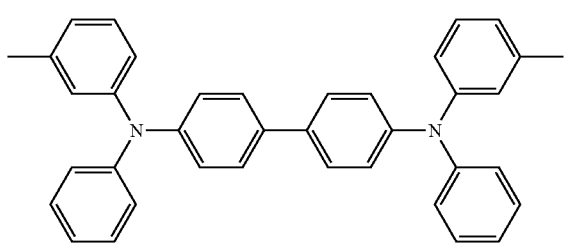

NPB

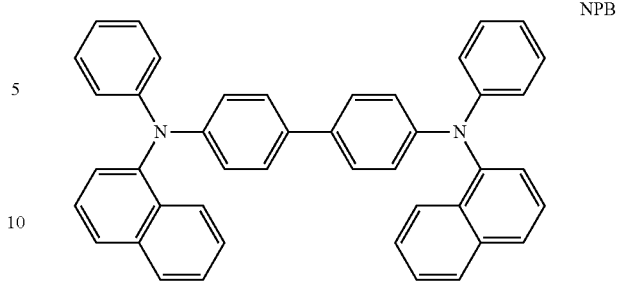

The thickness of the HTL can be from about 50 Å to about 2000 Å, and in some embodiments, can be from about 100 Å to about 1500 Å. When the thickness of the HTL is within these ranges, the HTL can have good hole transporting ability without a driving voltage that is too high to be of economical use.

The H-functional layer (having both hole injection and hole transport capabilities) can contain at least one material from each group of the hole injection layer materials and hole transport layer materials. The thickness of the H-functional layer can be from about 500 Å to about 10,000 Å, and in some embodiments, can be from about 100 Å to about 1,000 Å. When the thickness of the H-functional layer is within these ranges, the H-functional layer can have good hole injection and transport capabilities without a driving voltage that is too high to be of economical use.

In some embodiments, at least one of the HIL, HTL, and H-functional layers can include at least one of a compound of Formula 300 below and a compound of Formula 350 below.

Formula 300

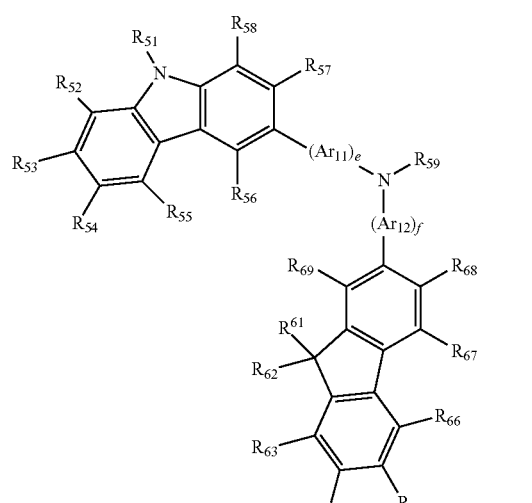

Formula 350

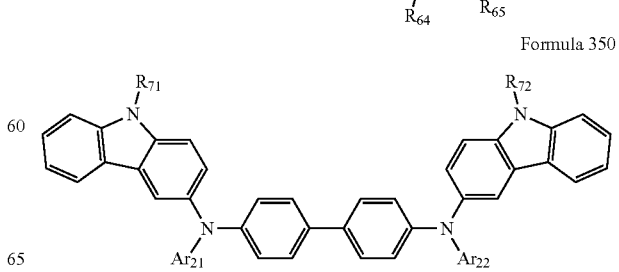

In Formulae 300 and 350, $Ar_{11}$, $Ar_{12}$, $Ar_{21}$ and $Ar_{22}$ can be each independently a substituted or unsubstituted $C_5$-$C_{60}$ arylene group. $Ar_{11}$, $Ar_{12}$, $Ar_{21}$ and $Ar_{22}$ are as defined above for substituted or unsubstituted $C_5$-$C_{60}$ aryl groups in conjunction with Formula 1, and thus a detailed description thereof will not be provided here.

In Formula 300, e and f can be each independently an integer from 0 to 5, for example, e or f can be 0, 1, or 2. In a non-limiting embodiment, e can be 1, and f can be 0.

In Formulae 300 and 350, $R_{51}$ to $R_{58}$, $R_{61}$ to $R_{69}$, and $R_{71}$ to $R_{72}$ can be each independently one of a hydrogen atom, a deuterium atom, a halogen atom, a hydroxyl group, a cyano group, a nitro group, an amino group, an amidino group, hydrazine, hydrazone, a carboxyl group or a salt thereof, sulfonic acid or a salt thereof, phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, and a substituted or unsubstituted $C_5$-$C_{60}$ arylthio group. In some non-limiting embodiments, $R_{51}$ to $R_{58}$, $R_{61}$ to $R_{69}$, $R_{71}$, and $R_{72}$ can be each independently one of a hydrogen atom; a deuterium atom; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, and a $C_1$-$C_{10}$ alkoxy group. In Formula 300, $R_{59}$ can be each independently a phenyl group, a naphthyl group, an anthryl group, a biphenyl group, or a pyridyl group; or a phenyl group, a naphthyl group, an anthryl group, a biphenyl group, or a pyridyl group that are substituted with at least one of a deuterium atom, a halogen atom, a hydroxyl group, a cyano group, a nitro group, an amino group, an amidino group, hydrazine, hydrazone, a carboxyl group or a salt thereof, sulfonic acid or a salt thereof, phosphoric acid or a salt thereof, a substituted or unsubstituted $C_1$-$C_{20}$ alkyl group, and a substituted or unsubstituted $C_1$-$C_{20}$ alkoxy group.

In an embodiment, the compound of Formula 300 can be a compound represented by Formula 300A below.

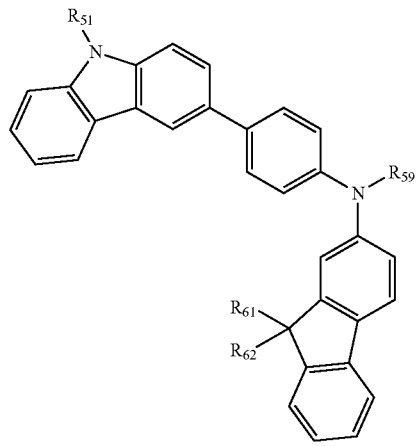

Formula 300A $R_{51}$, $R_{60}$, $R_{61}$ and $R_{59}$ in Formula 300A are as defined for substituents in Formulas 300 and 350 above, and thus a detailed description thereof will not be provided here.

In some non-limiting embodiments, at least one of the HIL, HTL, and H-functional layer can include at least one of compounds represented by Formulae 301 to 320 below.

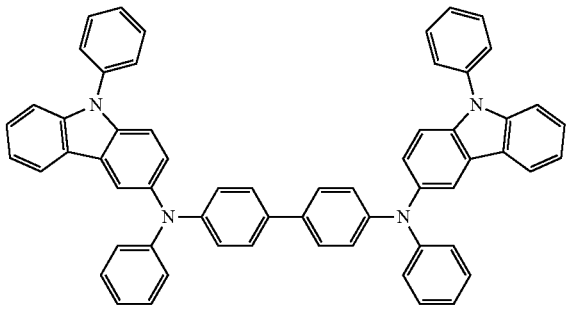

301

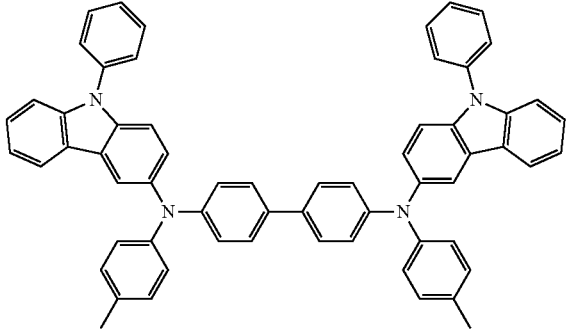

302

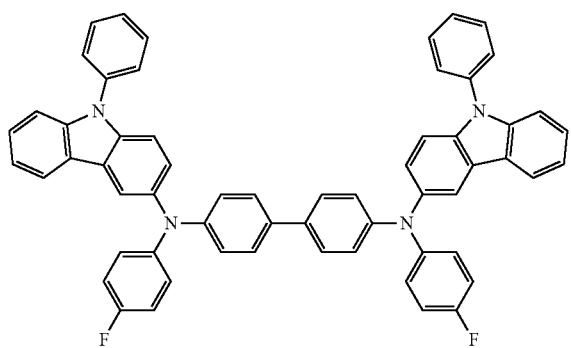
303
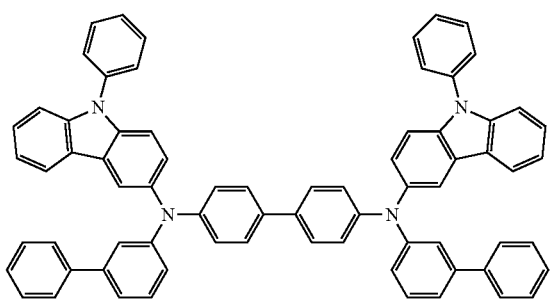
307
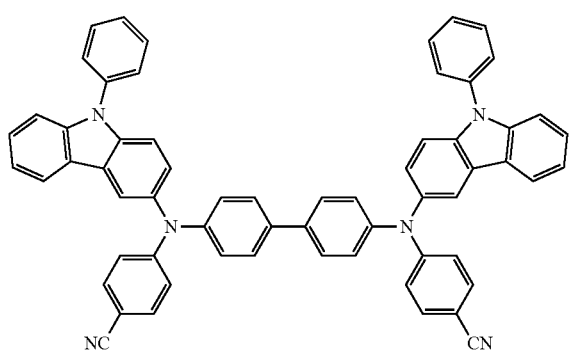
304
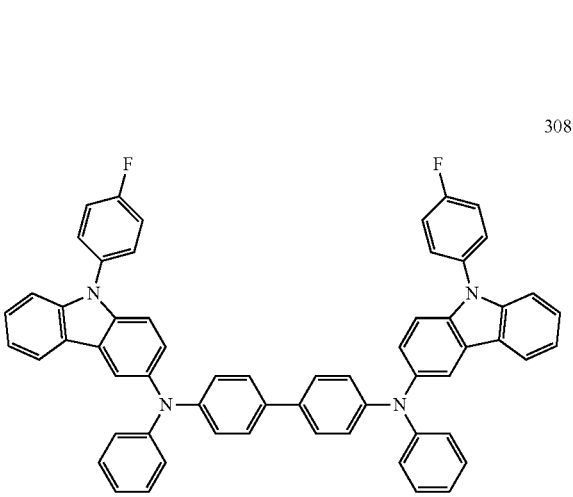
308
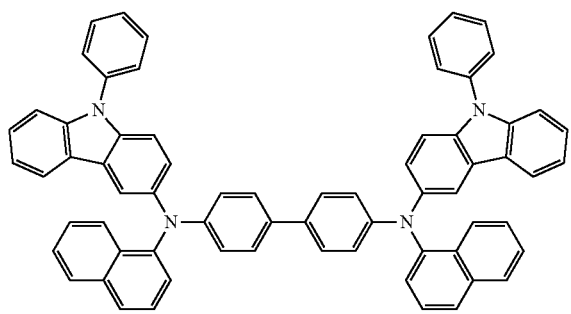
305
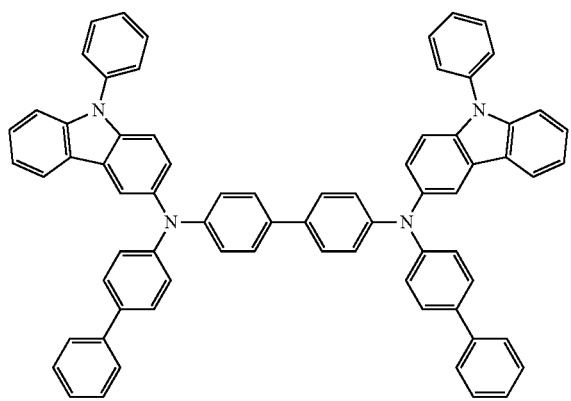
306
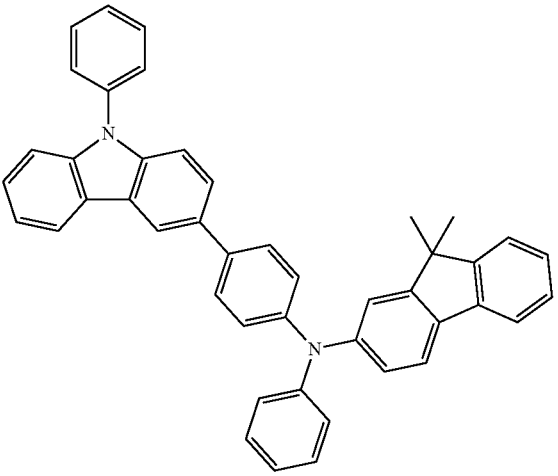
309

125
-continued
126
-continued
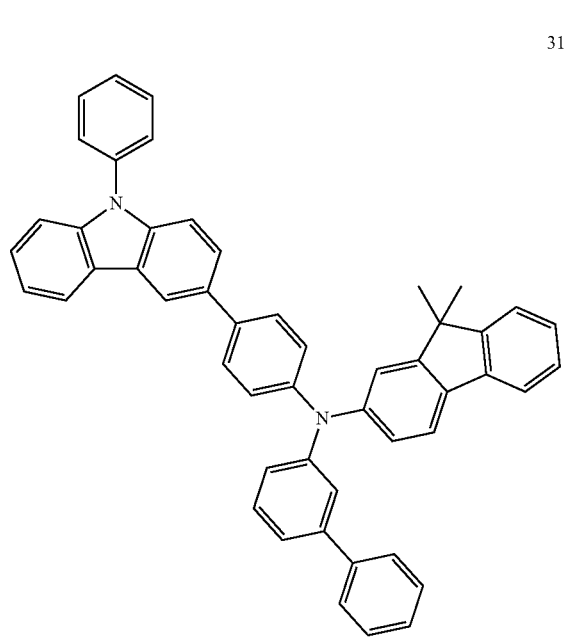
310
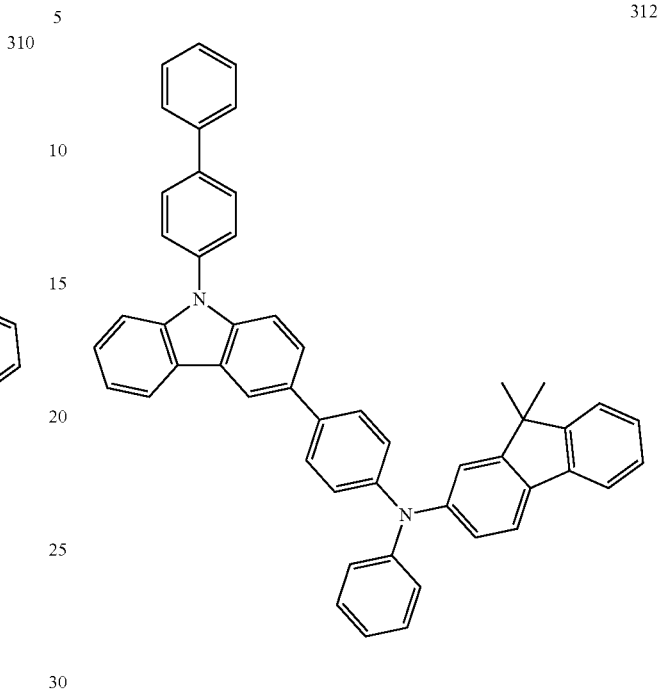
312
311
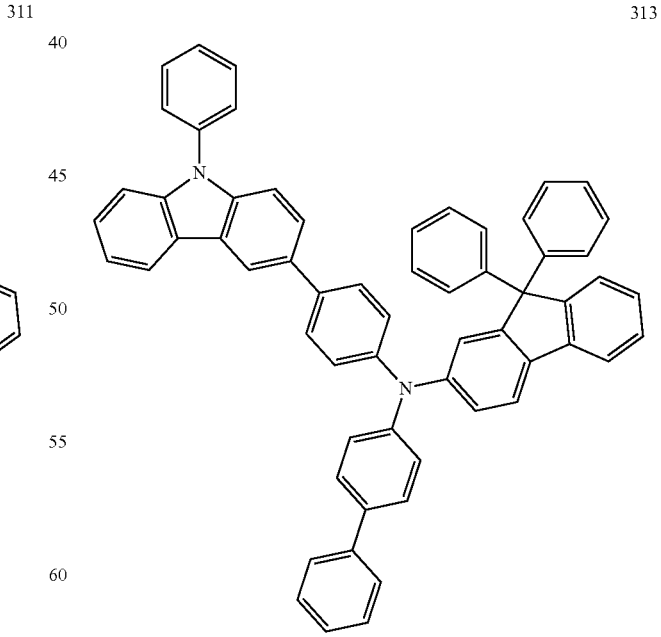
313

-continued
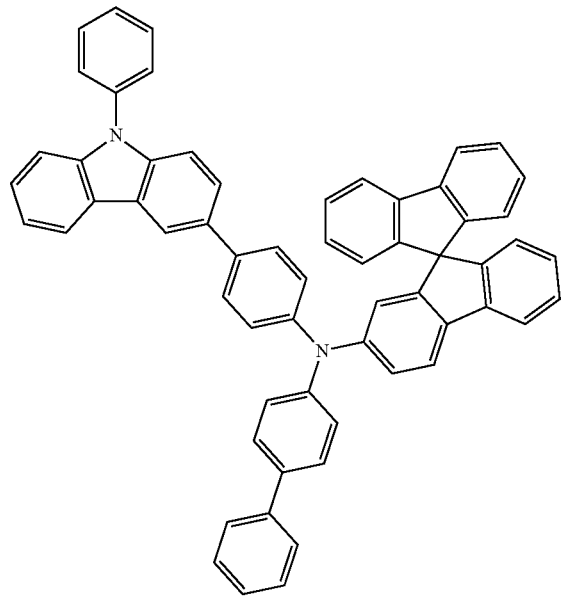
314
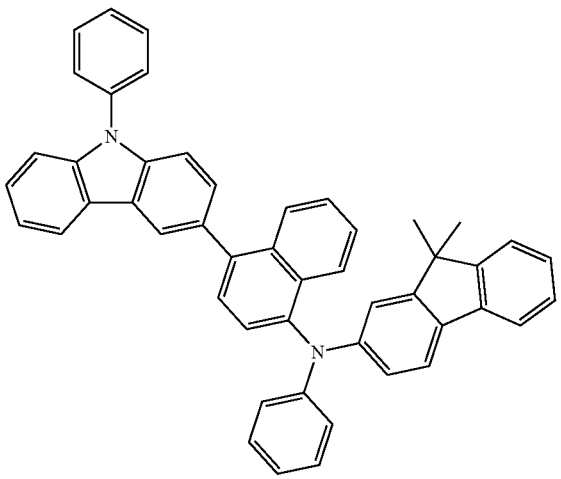
316
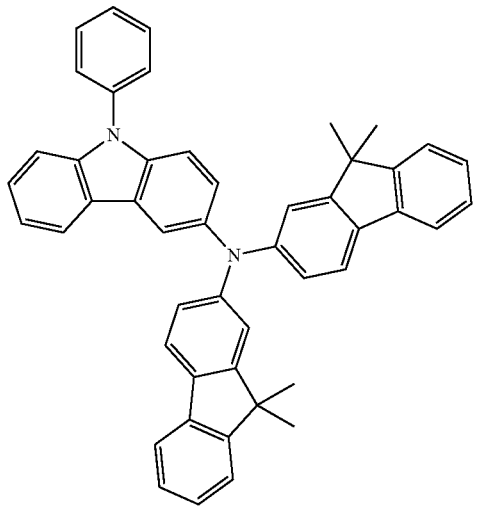
317
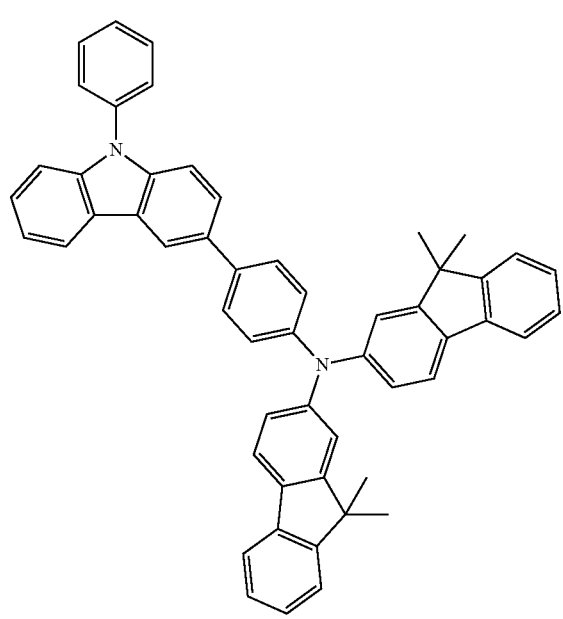
315
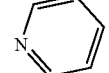
318

-continued

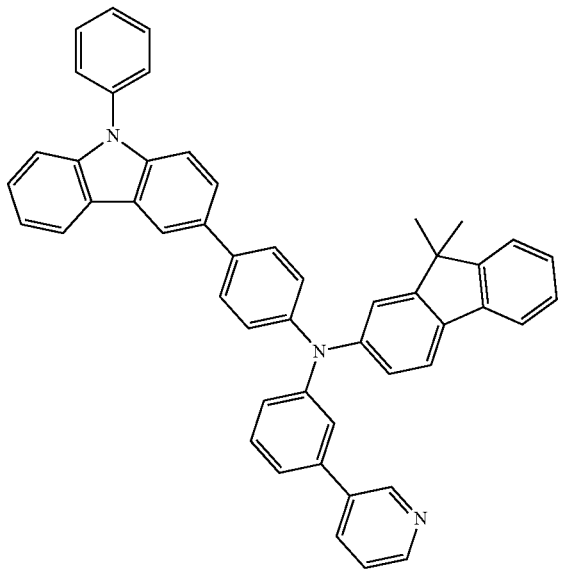

319

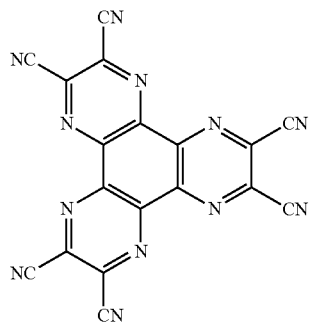

Compound 200

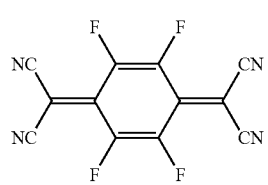

<F4-CTNQ>

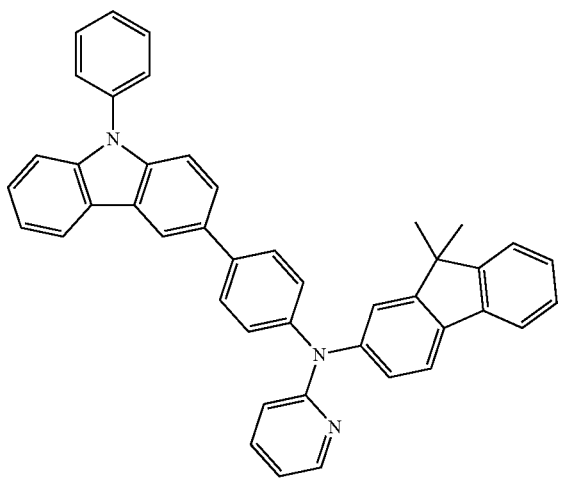

320

At least one of the HIL, HTL, and H-functional layer can further include a charge-generating material for improved layer conductivity, in addition to a known hole injecting material, hole transport material, and/or material having both hole injection and hole transport capabilities as described above.

The charge-generating material can be, for example, a p-dopant. The p-dopant may be one of quinine derivatives, metal oxides, and compounds with a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-CTNQ), and the like; metal oxides such as tungsten oxide, molybdenum oxide, and the like; and cyano-containing compounds such as Compound 200 below.

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The butter layer can include any hole injecting material or hole transporting material; some are widely known. In some other embodiments, the buffer layer can include the same material as one of the materials included in the HIL, HTL, and H-functional layer that underlie the buffer layer.

Then, an EML can be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions can be similar to those for the formation of the HIL, though the conditions for deposition and coating can vary according to the material that is used to form the EML.

The EML can include any of the heterocyclic compounds of Formulae 1 to 4

The EML can further include a host, in addition to the heterocyclic compounds of Formulae 1 to 4.

Non-limiting examples of the host are tris(8-hydroxyquinolinolato)aluminum (III) ($Alq_3$), 4,4'-N,N'-dicarbazole-biphenyl (CBP), poly(n-vinylcarbazole) (PVK), 9,10-di (naphthalene-2-yl)anthracene (ADN), 4,4',4"-tris(N-carbazolyl)triphenylamine (TCTA), 1,3,5-tris(N-phenylbenzimidazole-2-yl)benzene (TPBI), 3-tert-butyl-9,10-di-2-naphthylanthracene (TBADN), 2,7-bis(9,9-diethylfluorene-2-yl)-9,9-diethylfluorene (E3), distyrylarylene (DSA), 2,2'-dimethyl-4,4'-bis(9-azafluorene-9-yl)biphenyl (dmCBP) (see a formula below), and Compounds 501 to 509 below.

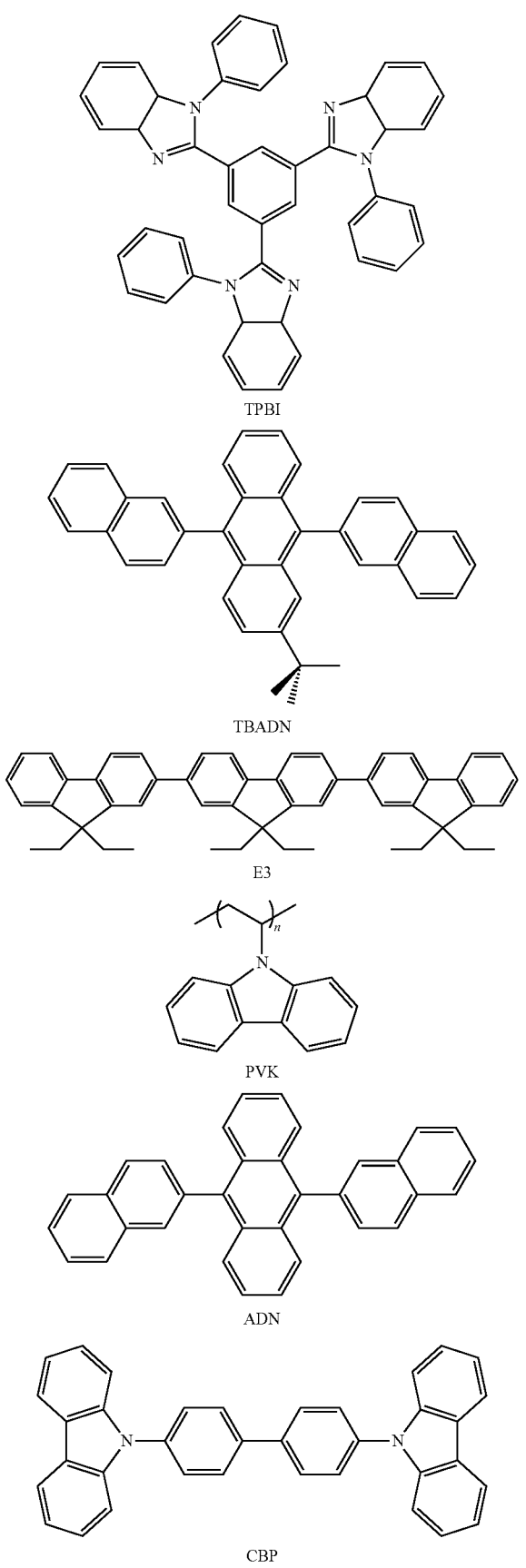
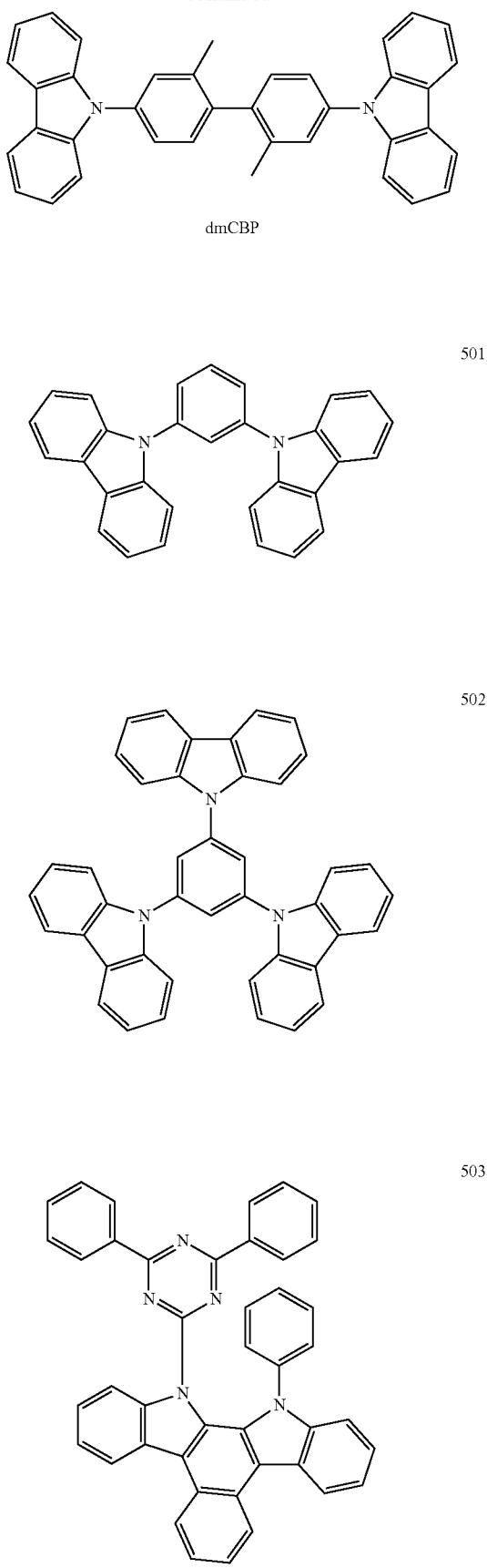

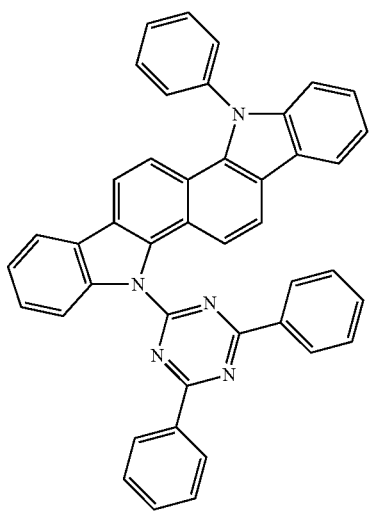

504

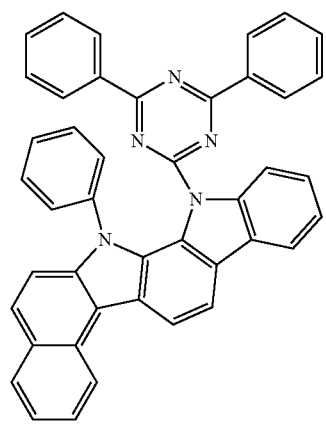

505

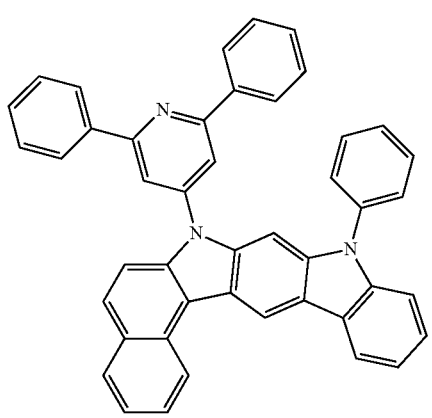

506

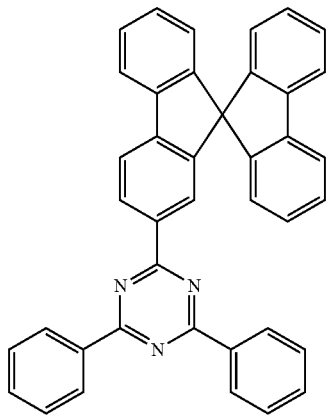

507

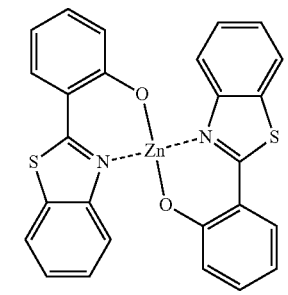

508

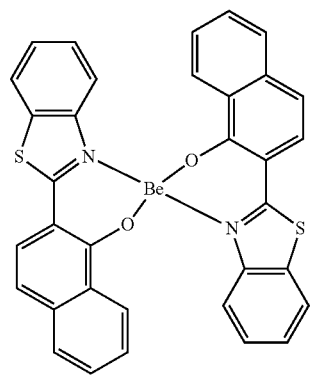

509

In some embodiments, an anthracene-based compound represented by Formula 400 below may be used as the host.

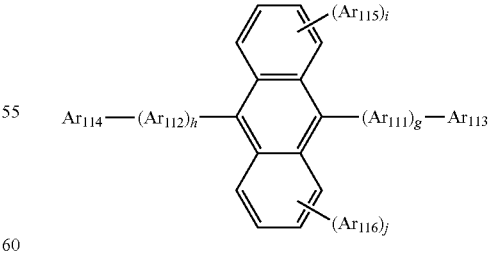

Formula 400

In Formula 400, $Ar_{111}$ and $Ar_{112}$ are each independently a substituted or unsubstituted $C_5$-$C_{60}$ arylene group; $Ar_{113}$ to $Ar_{116}$ are each independently a substituted or unsubstituted alkyl group or a substituted or unsubstituted C5-$C_{60}$ aryl group; and g, h, i, and j are each independently an integer from 0 to 4.

In some non-limiting embodiments, $Ar_{111}$ and $Ar_{112}$ in Formula 400 can be each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group.

In Formula 400 above, g, h, i, and j can be each independently 0, 1, or 2.

In some non-limiting embodiments, $Ar_{113}$ to $Ar_{116}$ in Formula 400 can be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

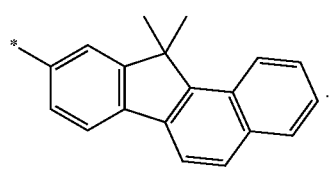 [SMILES: *c1ccc2c(c1)C(C)(C)c1c-2ccc2ccccc12]

For example, the anthracene compound of Formula 400 above may be one of the compounds represented by the following formulae, but is not limited thereto.

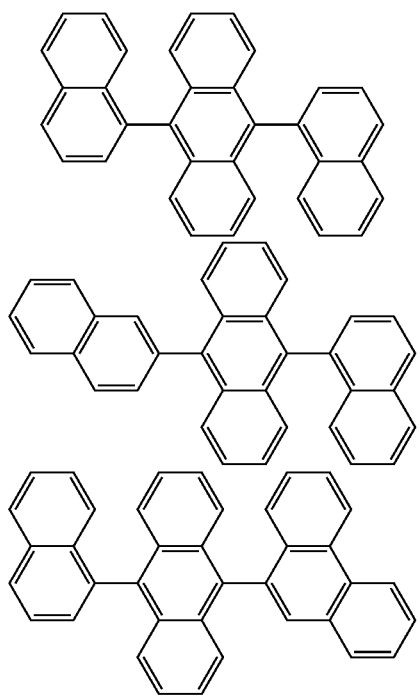

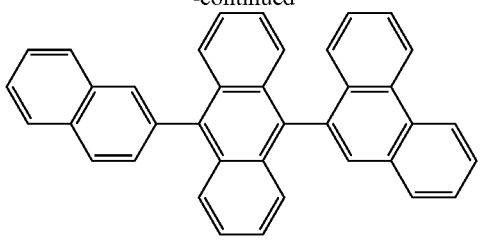

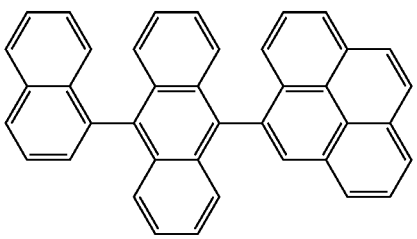

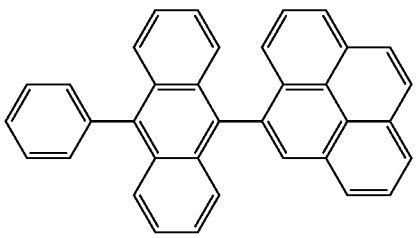

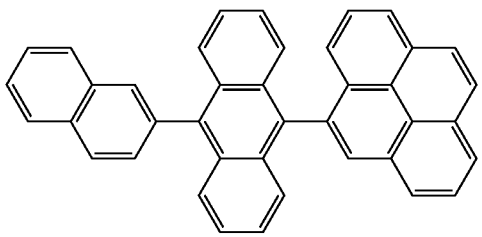

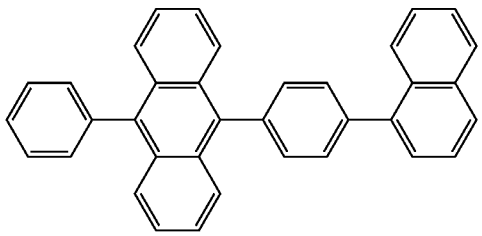

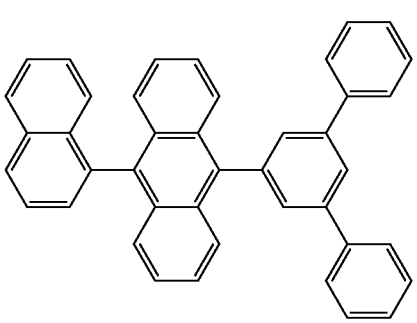

137
-continued
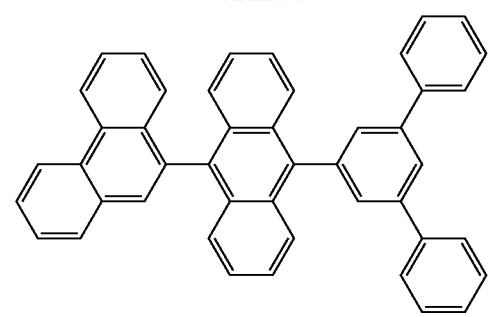
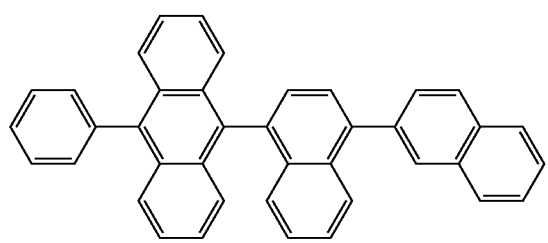
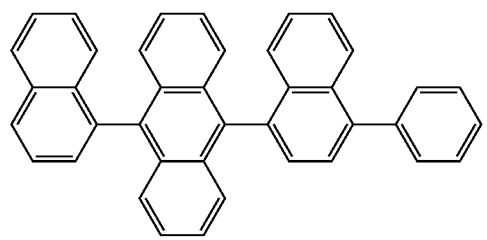
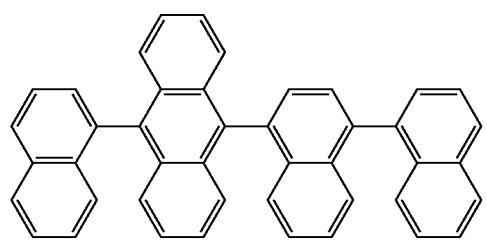
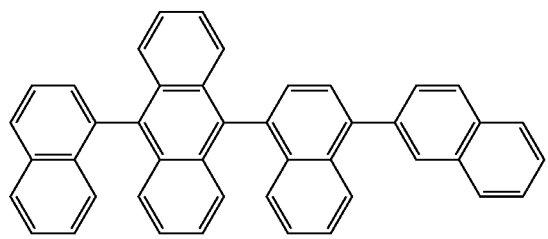
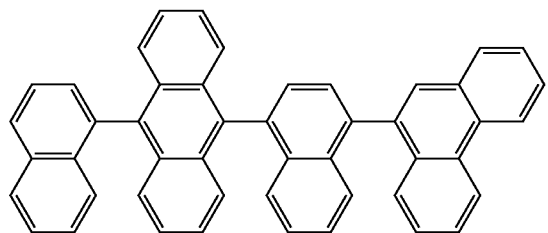
138
-continued
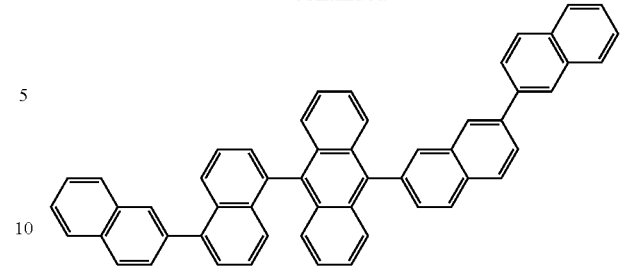
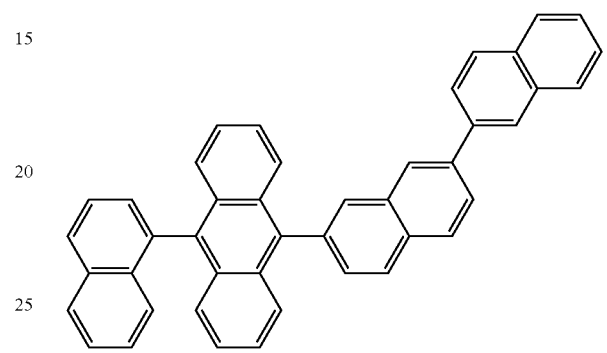
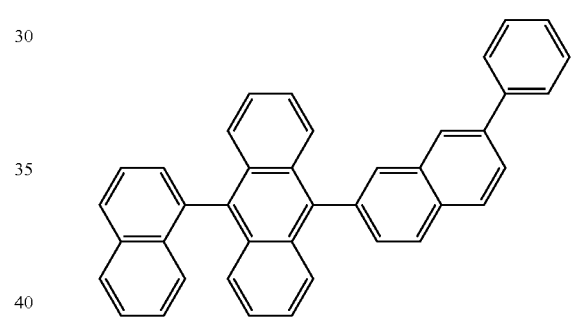
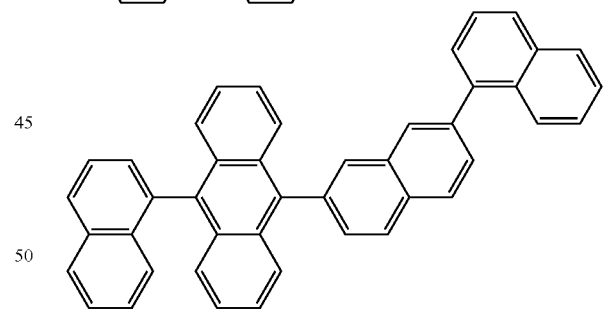
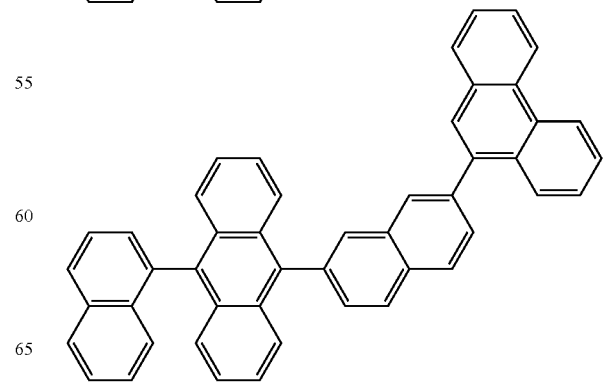

-continued
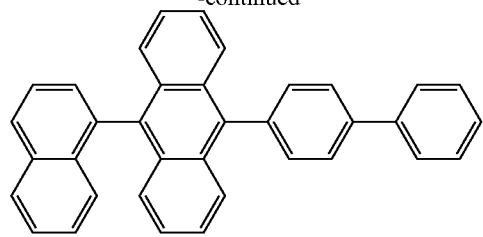
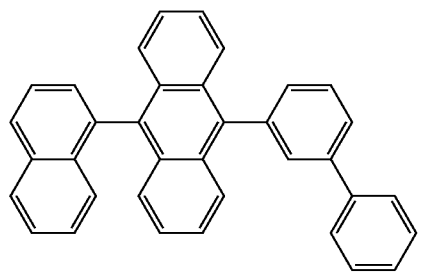
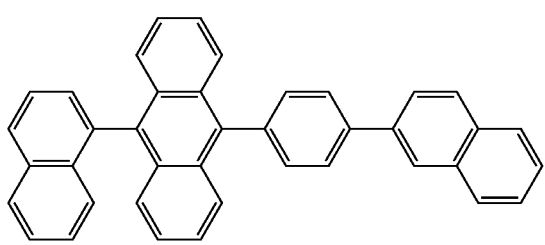
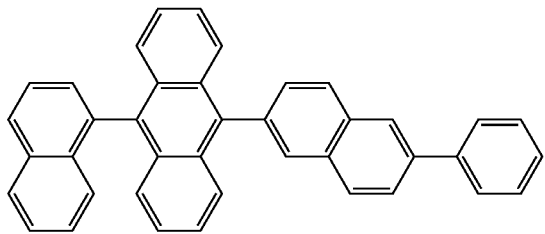
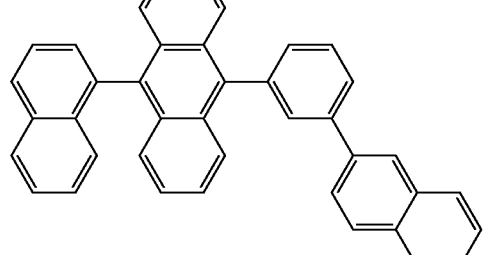
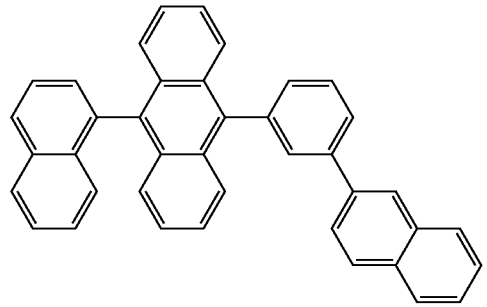
-continued
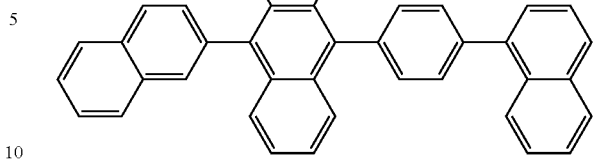
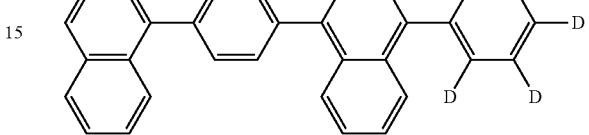
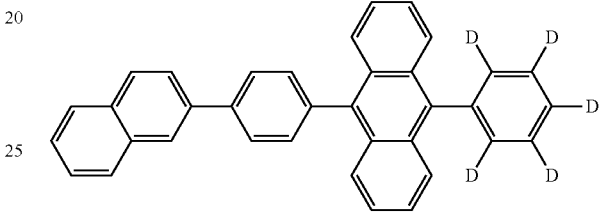
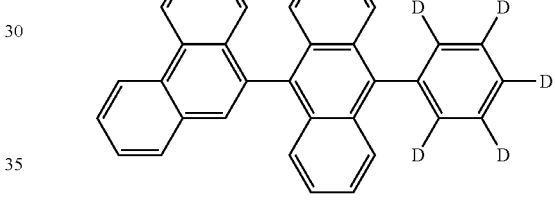
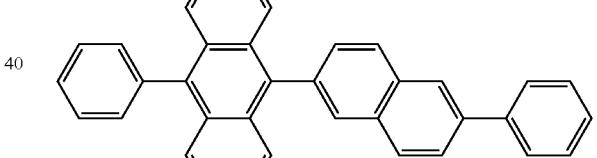
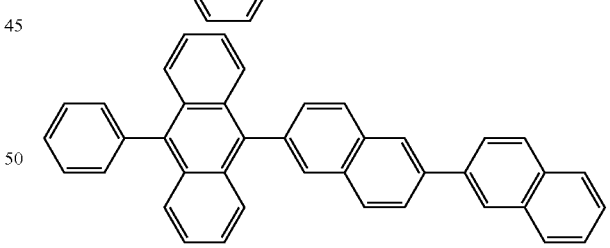
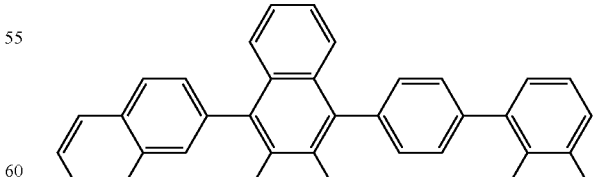
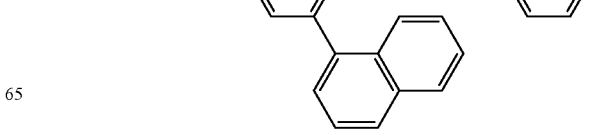

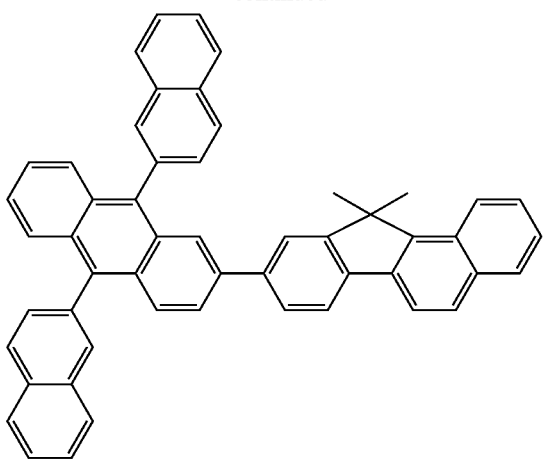
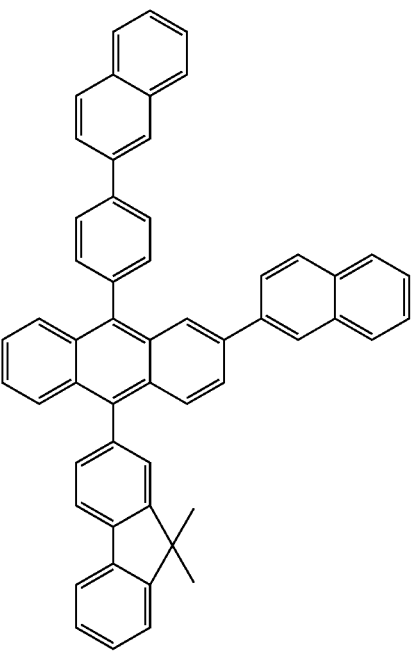
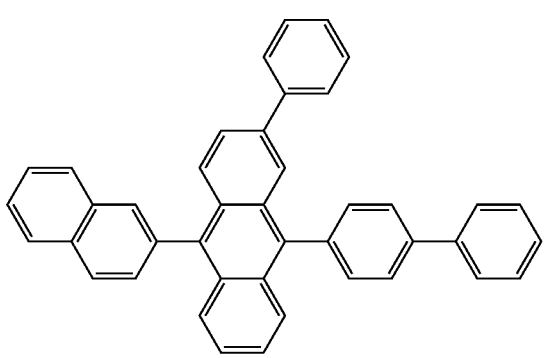
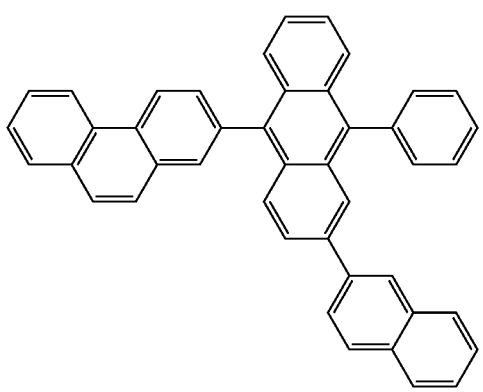
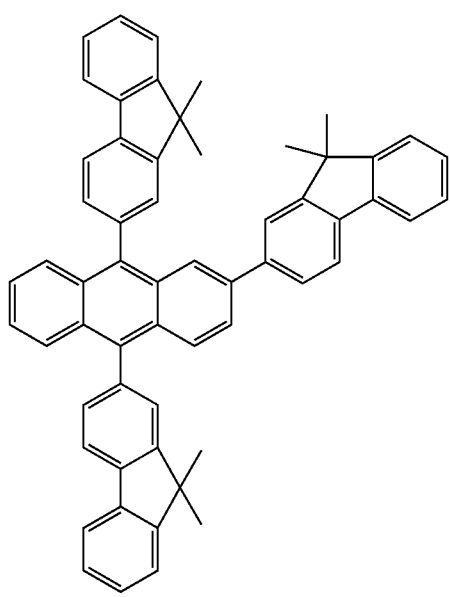
In some embodiments, an anthracene-based compound represented by Formula 401 below can be used as the host.
Formula 401
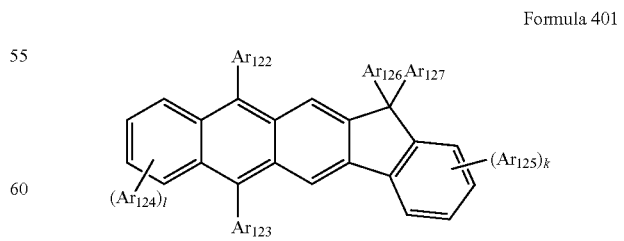
$Ar_{122}$ to $Ar_{125}$ in Formula 401 above can be defined as described above in conjunction with $Ar_{113}$ of Formula 400, and thus detailed descriptions thereof will not be provided here.

$Ar_{126}$ and $Ar_{127}$ in Formula 401 above can be each independently a $C_1$-$C_{10}$ alkyl group, for example, a methyl group, an ethyl group, or a propyl group.

In Formula 401, k and l can be each independently an integer from 0 to 4, for example, 0, 1, or 2.

For example, the anthracene compound of Formula 401 above can be one of the compounds represented by the following formulae, but is not limited thereto.

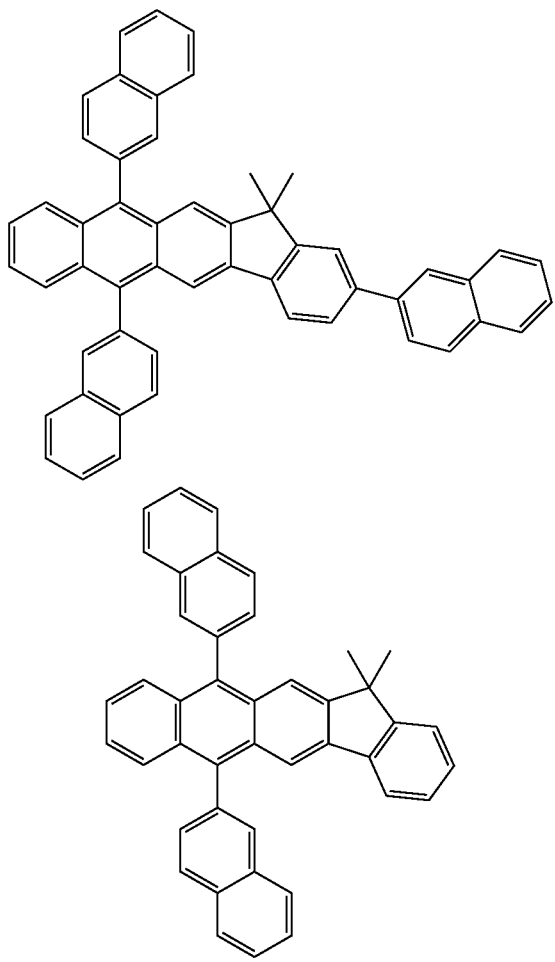

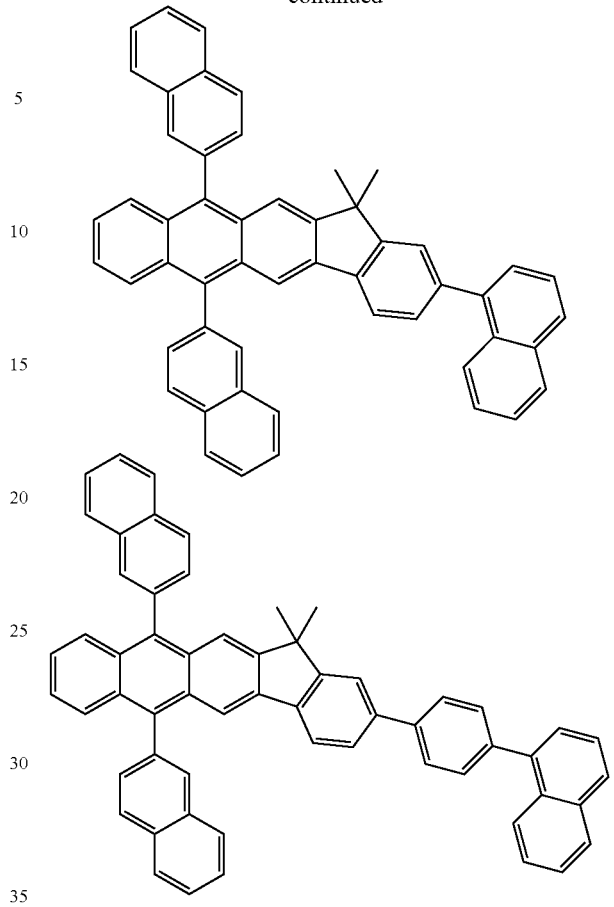

When the organic light-emitting device is a full color organic light-emitting device, the emission layer can be patterned into a red emission layer, a green emission layer, and a blue emission layer. For example, the blue emission layer can include any of the heterocyclic compounds of Formulae 1 to 4 as a blue fluorescent dopant. In some embodiments, the green emission layer can include any of the heterocyclic compounds of Formulae 1 to 4 as a green phosphorescent host.

At least one of the red EML, the green EML, and the blue EML can include a dopant below (ppy=phenylpyridine).

Further to the heterocyclic compound of Formulae 1 to 4, non-limiting examples of the blue dopant are compounds represented by the following formulae.

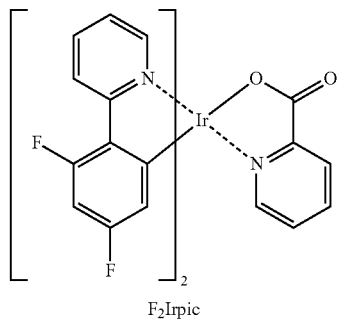

F₂Irpic

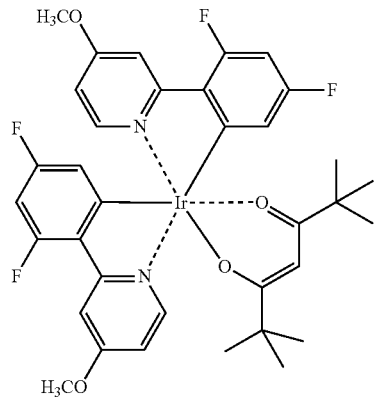

(F₂ppy)₂Ir(tmd)

-continued
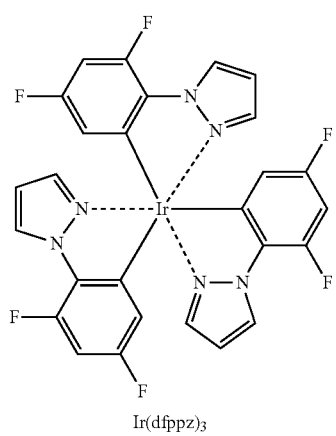
Ir(dfppz)₃
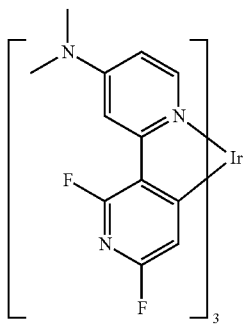
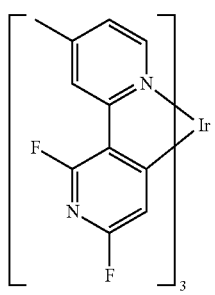
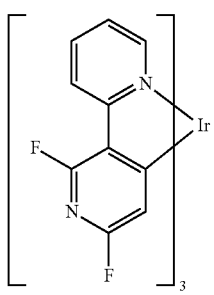
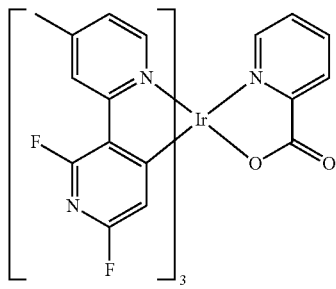
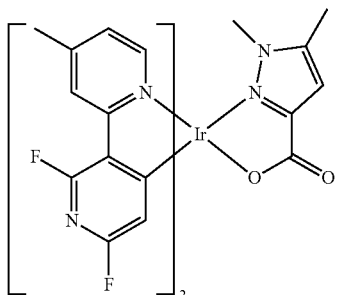
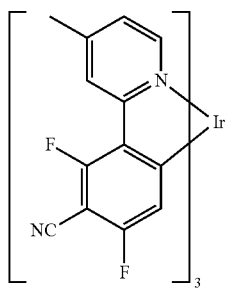
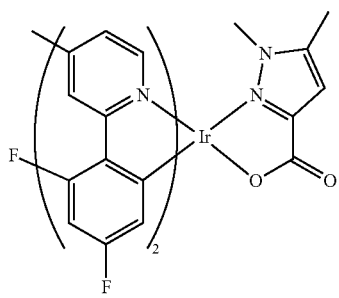
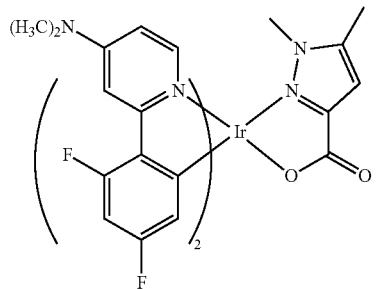
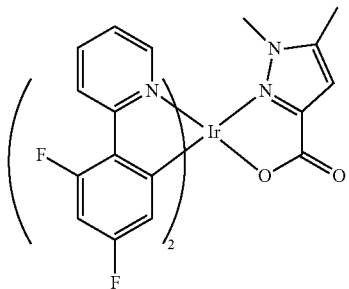

-continued
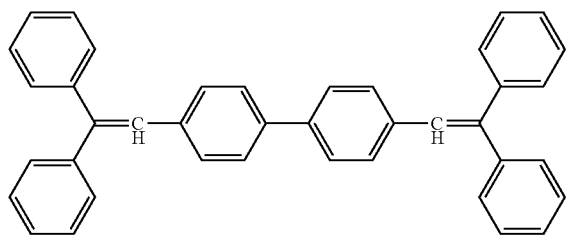
DPVBi
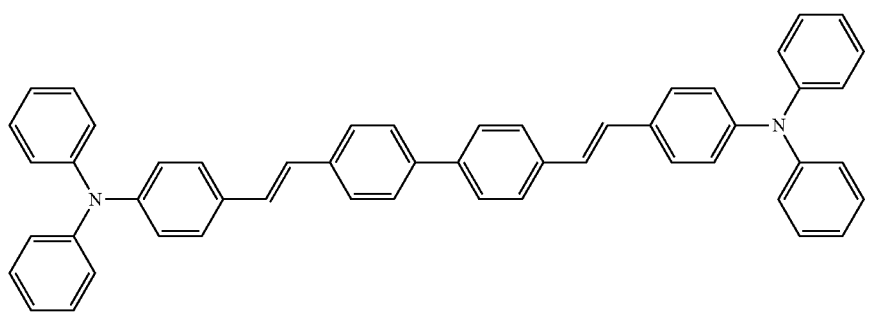
DPAVBi
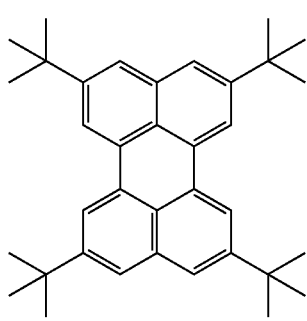
TBPe
Non-limiting examples of the red dopant are compounds represented by the following formulae.
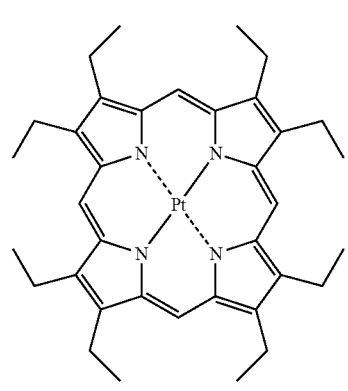
PtOEP
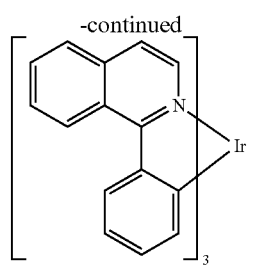
Ir(piq)$_3$
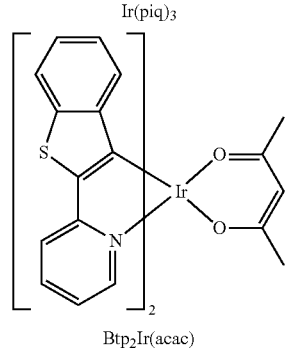
Btp$_2$Ir(acac)

-continued
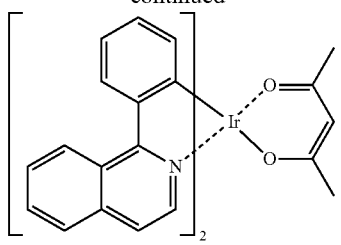
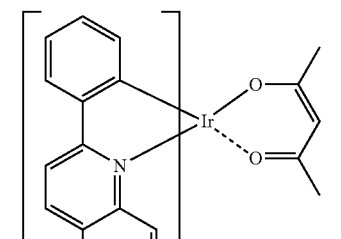
Ir(pq)₂(acac)
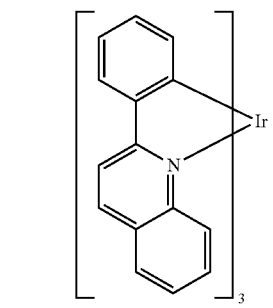
Ir(2-phq)₃
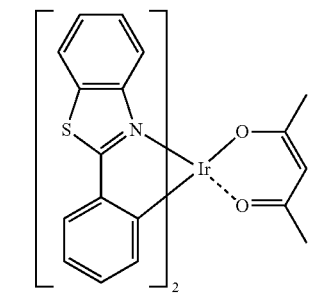
Ir(BT)₂(acac)
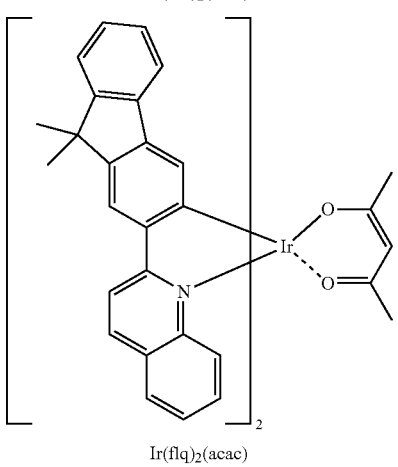
Ir(flq)₂(acac)
-continued
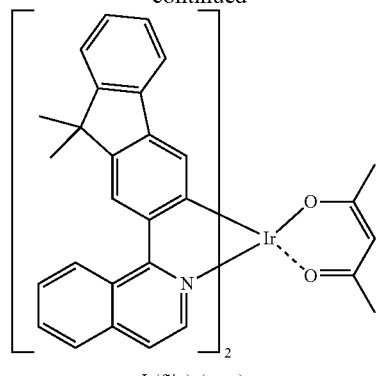
Ir(fliq)₂(acac)
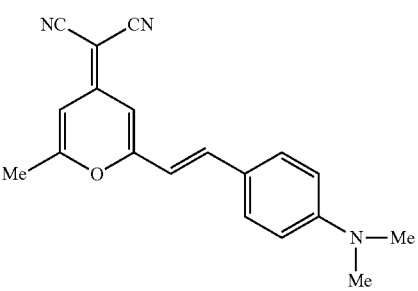
DCM
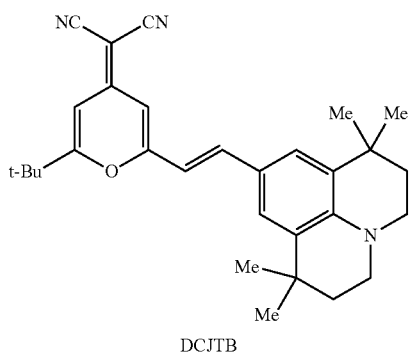
DCJTB
Non-limiting examples of the green dopant are compounds represented by the following formulae.
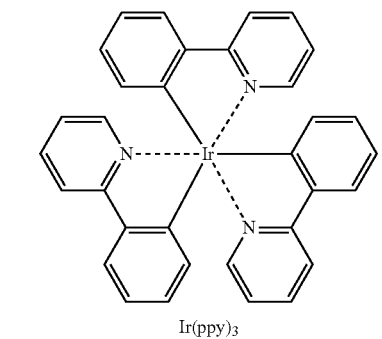
Ir(ppy)₃

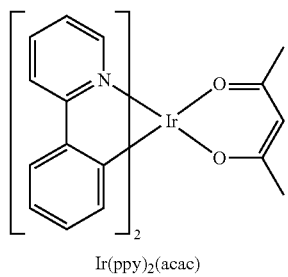
Ir(ppy)₂(acac)
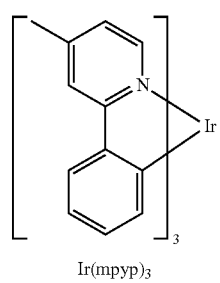
Ir(mpyp)₃
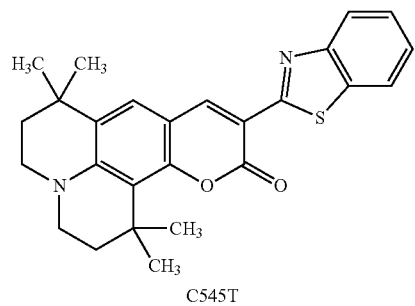
C545T
Non-limiting examples of the dopant that can be used in the EML are Pt complexes represented by the following formulae.
D1
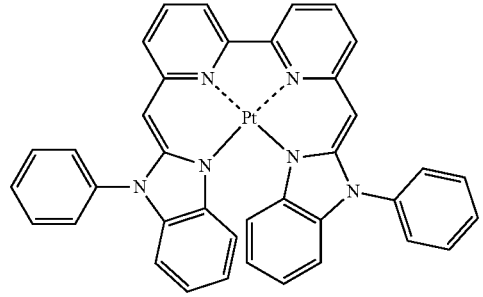
D3
D2
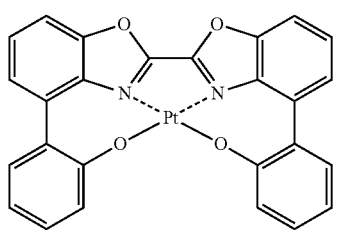
D4
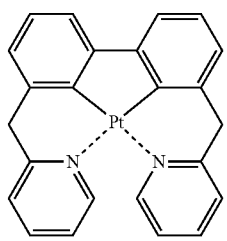
D5
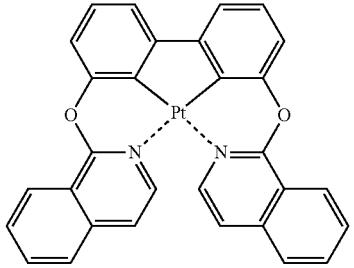
D6
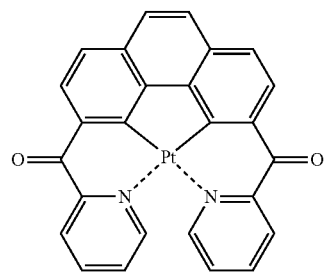
D7
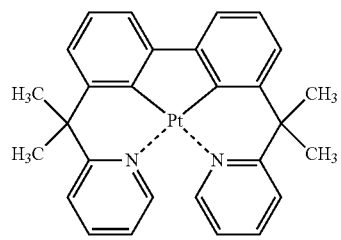
D8

D9
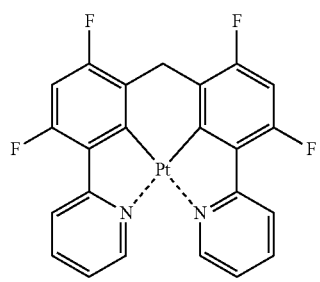
D10
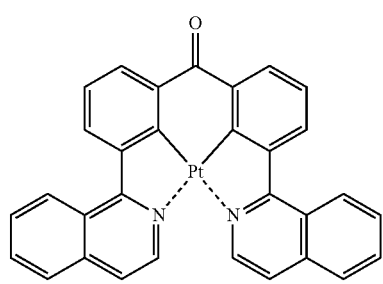
D11
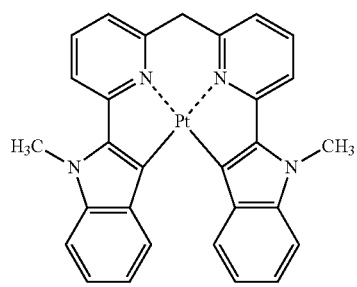
D12
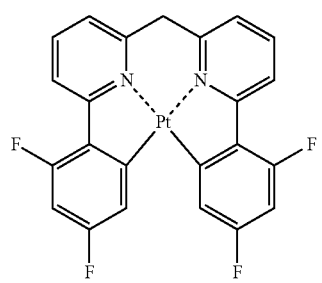
D13
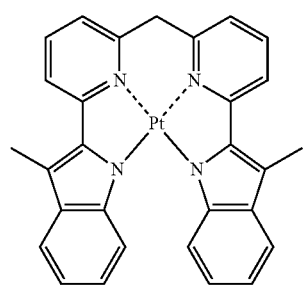
D14
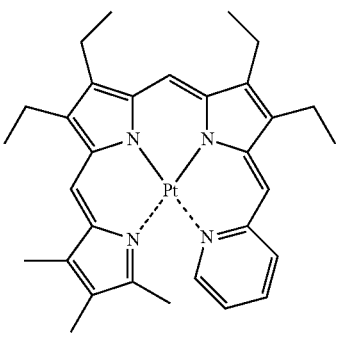
D15
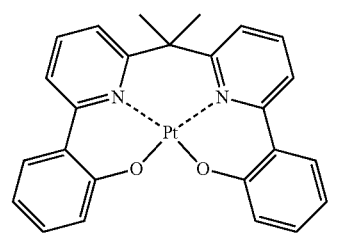
D16
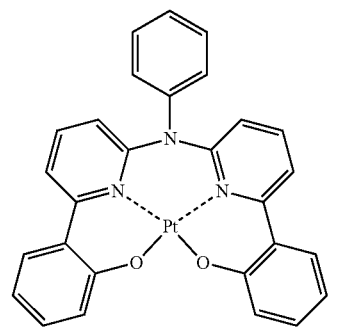
D17
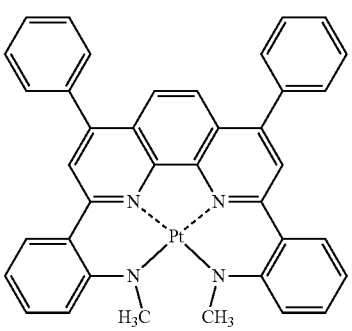
D18
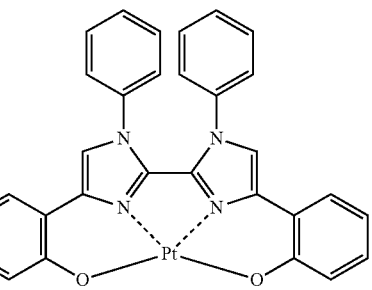

-continued
D19 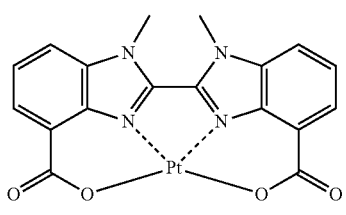
D20 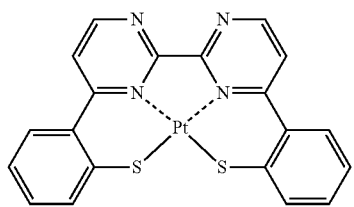
D21 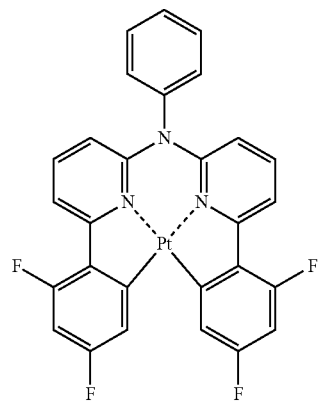
D22 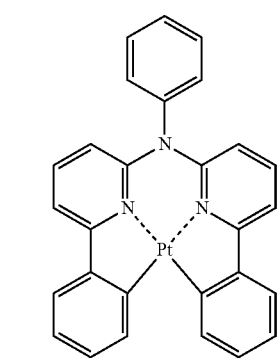
D23 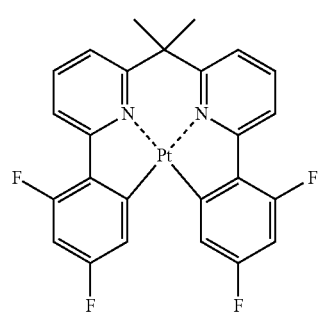
-continued
D24 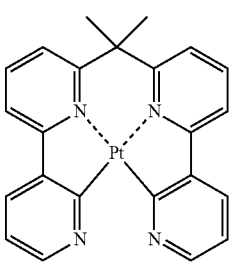
D25 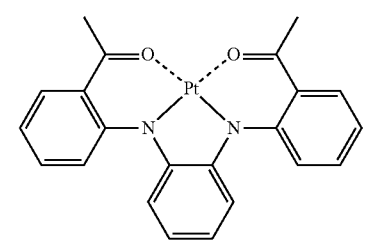
D26 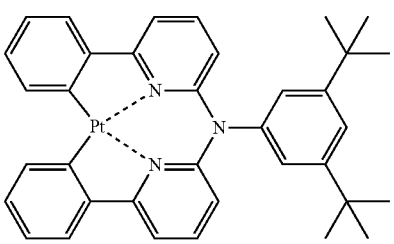
D27 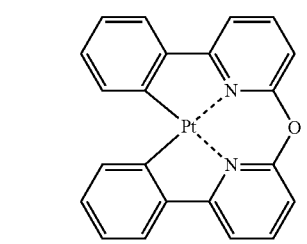
D28 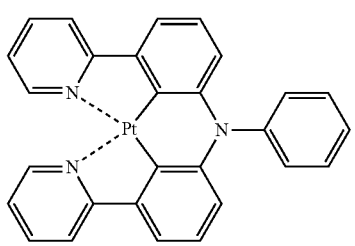
D29 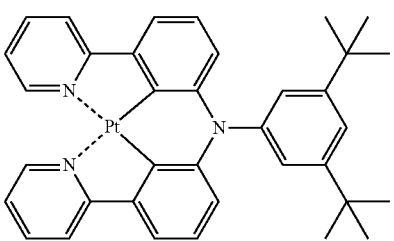

D30 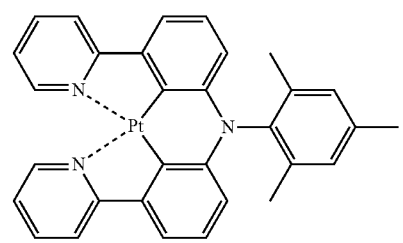
D31 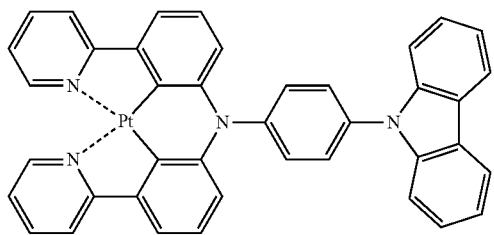
D32 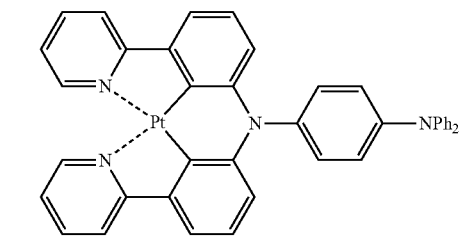
D33 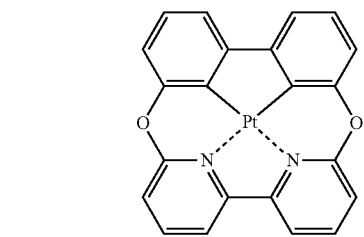
D34 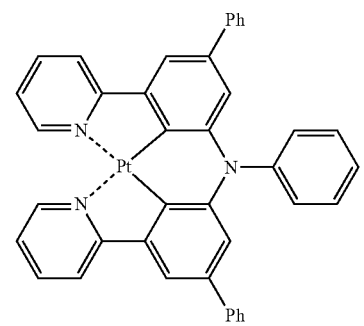
D35 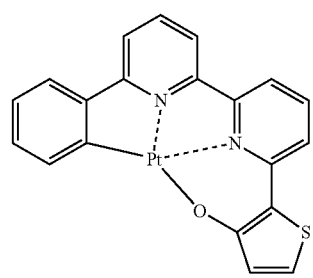
D36 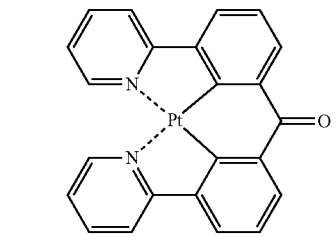
D37 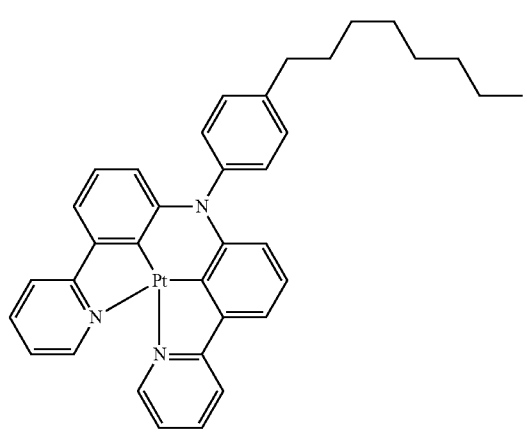
D38 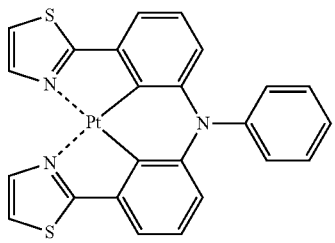
D39 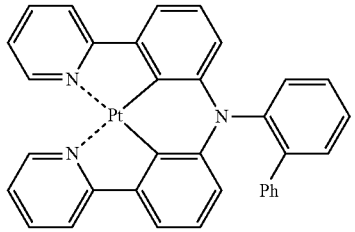
D40 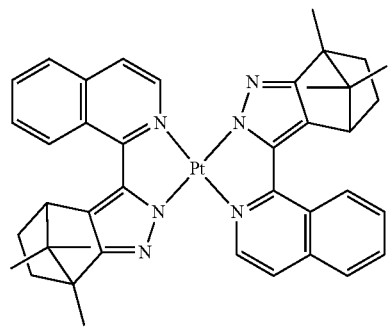

D41 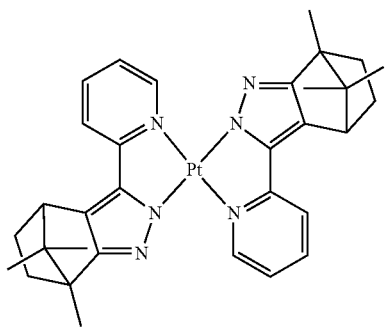
D42 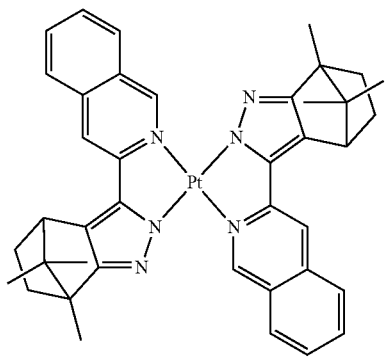
D43 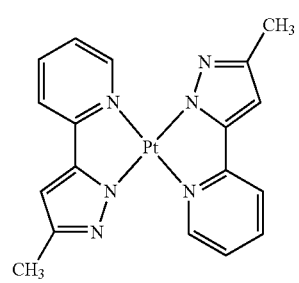
D44 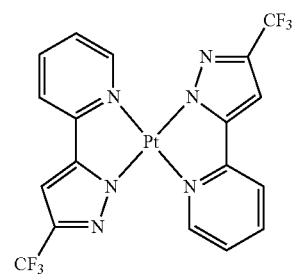
D45 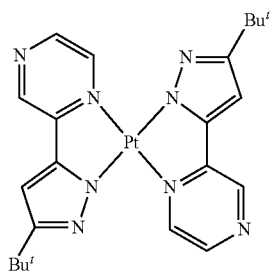
D46 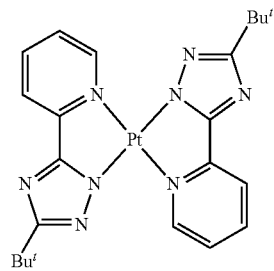
D47 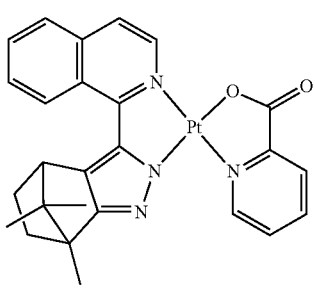
D48 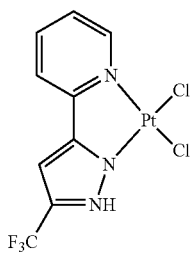
D49 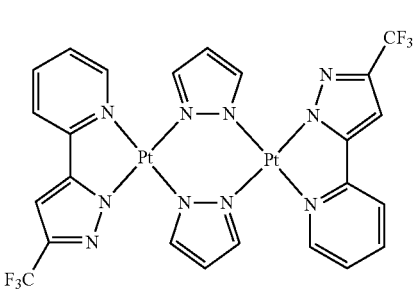
D50 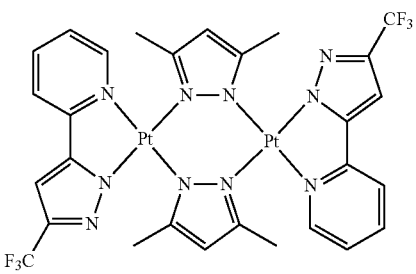
Non-limiting examples of the dopant that can be used in the EML are osmium complexes represented by the following formulae.

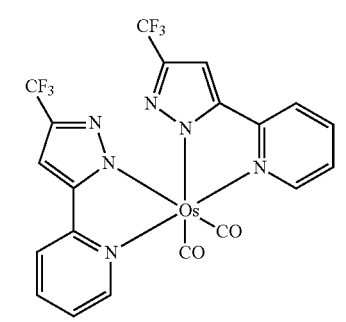

Os(fppz)₂(CO)₂

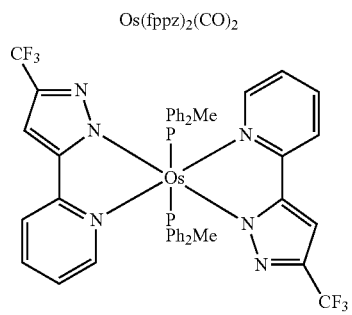

Os(fppz)₂(PPh₂Me)₂

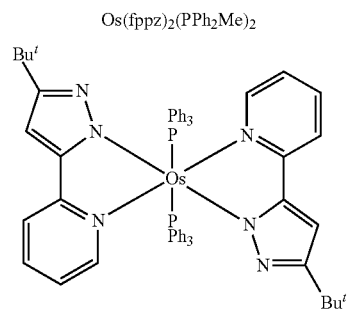

Os(bppz)₂(PPh₃)₂

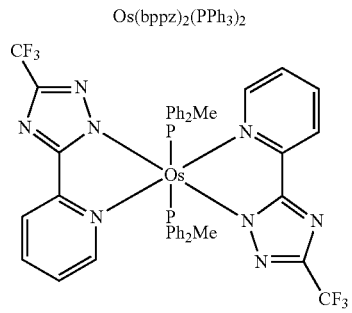

Os(fptz)₂(PPh₂Me)₂

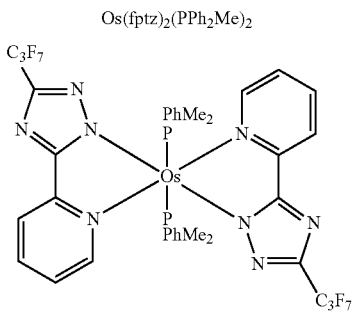

Os(hptz)₂(PPhMe₂)₂

When the EML includes both a host and a dopant, the amount of the dopant can be from about 0.01 to about 15 parts by weight based on 100 parts by weight of the host. However, the amount of the dopant is not limited to this range.

The thickness of the EML can be from about 100 Å to about 1000 Å, and in some embodiments, can be from about 200 Å to about 600 Å. When the thickness of the EML is within these ranges, the EML can have good light emitting ability without requiring a driving voltage that is too high to be of economical use.

Then, an ETL can be formed on the EML by vacuum deposition, spin coating, casting, or the like. When the ETL is formed using vacuum deposition or spin coating, the deposition and coating conditions can be similar to those for the formation of the HIL, though the deposition and coating conditions can vary according to the compound or compounds that are used to form the ETL. A material for forming the ETL can be any known material that can stably transport electrons injected from an electron injecting electrode (cathode). Non-limiting examples of materials for forming the ETL are a quinoline derivative, such as tris(8-hydroxyquinolinato)aluminum (III) (Alq3), TAZ, BAlq, beryllium bis(benzoquinolin-10-olate (Bebq₂), 9,10-di(naphth-2-yl)anthracene (ADN), Compound 201, and Compound 202, but are not limited thereto.

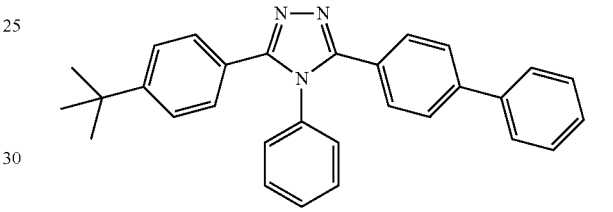

TAZ

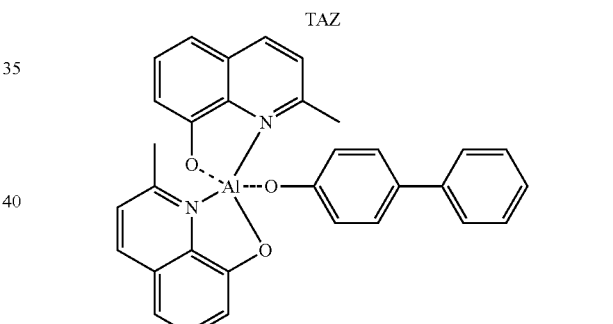

Balq

Compound 201

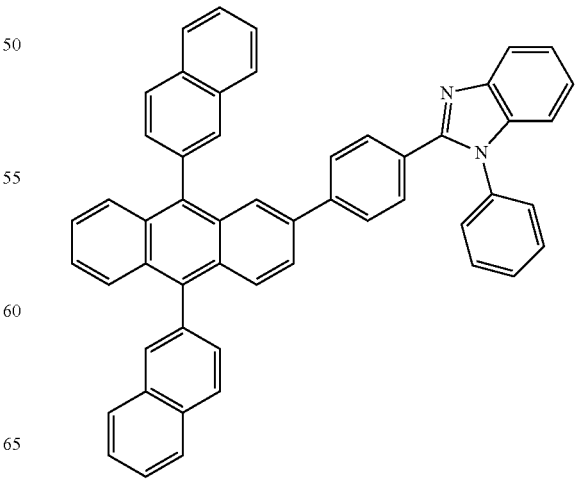

Compound 202

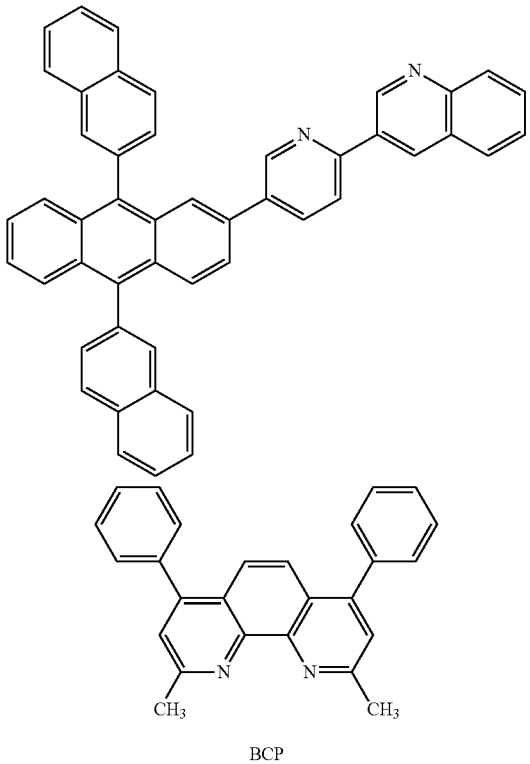

BCP

The thickness of the ETL can be from about 100 Å to about 1,000 Å, and in some embodiments, can be from about 150 Å to about 500 Å. When the thickness of the ETL is within these ranges, the ETL can have satisfactory electron transporting ability without a driving voltage that is too high for economical use.

In some embodiments the ETL can further include a metal-containing material, in addition to any known electron-transporting organic compound.

The metal-containing material can include a lithium (Li) complex. Non-limiting examples of the Li complex are lithium quinolate (LiQ) and Compound 203 below.

Compound 203

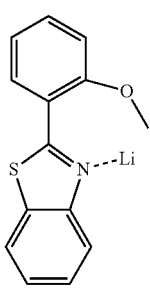

Then, an EIL, which facilitates injection of electrons from the cathode, can be formed on the ETL. Any suitable electron-injecting material can be used to form the EIL.

Non-limiting examples of materials for forming the EIL are LiF, NaCl, CsF, $Li_2O$, and BaO, which are known in the art. The deposition and coating conditions for forming the EIL 18 can be similar to those for the formation of the HIL, though the deposition and coating conditions can vary according to the material that is used to form the EIL 18.

The thickness of the EIL can be from about 1 Å to about 100 Å, and in some embodiments, can be from about 3 Å to about 90 Å. When the thickness of the EIL is within these ranges, the EIL can have satisfactory electron injection ability without a substantial increase in driving voltage.

Finally, the second electrode is disposed on the organic layer. The second electrode can be a cathode that is an electron injection electrode. A material for forming the second electrode can be a metal, an alloy, or an electro-conductive compound that has a low work function, or a mixture thereof. In this regard, the second electrode can be formed of lithium (Li), magnesium (Mg), aluminum (Al), aluminum (Al)-lithium (Li), calcium (Ca), magnesium (Mg)-indium (In), magnesium (Mg)-silver (Ag), or the like, and can be formed as a thin film type transmission electrode. In some embodiments, to manufacture a top-emission light-emitting device, the transmission electrode can be formed of indium tin oxide (ITO) or indium zinc oxide (IZO).

Although the organic light-emitting device of FIG. 1 is described above, the present invention is not limited thereto.

When a phosphorescent dopant is used in the EML, a hole buffer layer (HBL) can be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating can be similar to those for the formation of the HIL, although the conditions for deposition and coating can vary according to the material that is used to form the HBL. Any known hole-blocking material can be used. Non-limiting examples of hole-blocking materials are oxadiazole derivatives, triazole derivatives, and phenanthroline derivatives. For example, 2,9-dimethyl-4,7-diphenyl-1,10-phenanthroline (BCP) represented by the following formula can be used as a material for forming the

BCP

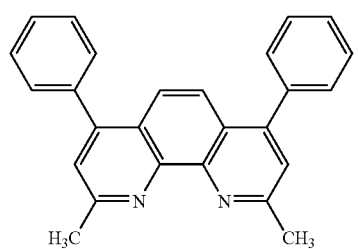

The thickness of the HBL can be from about 20 Å to about 1000 Å, and in some embodiments, can be from about 30 Å to about 300 Å. When the thickness of the HBL is within these ranges, the HBL can have improved hole blocking ability without a substantial increase in driving voltage.

According to embodiments of the present invention, the organic light-emitting device can be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate can function as a pixel electrode, electrically connected to a source electrode or a drain electrode of the thin-film transistor. Moreover, the organic light-emitting device can also be included in flat panel display devices having double-sided screens.

In some embodiments the organic layer of the organic light-emitting device can be formed of a compound according to Formula 1 by using a deposition method or can be formed using a wet method of coating a solution of the compound of Formula 1.

Hereinafter, the present invention will be described in detail with reference to the following synthesis examples and other examples. However, these examples are for illustrative purposes only and are not intended to limit the scope of the present invention.

EXAMPLES

Examples of reactants involved in the reaction schemes, which will be described later, are represented by the following formulae.

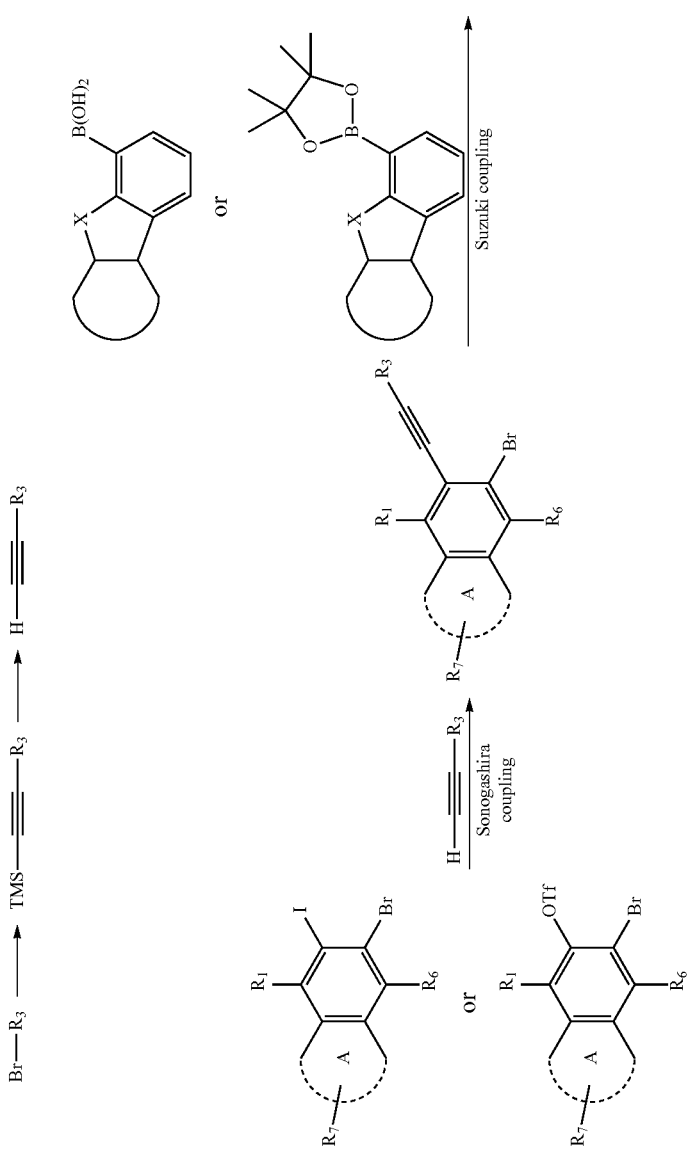

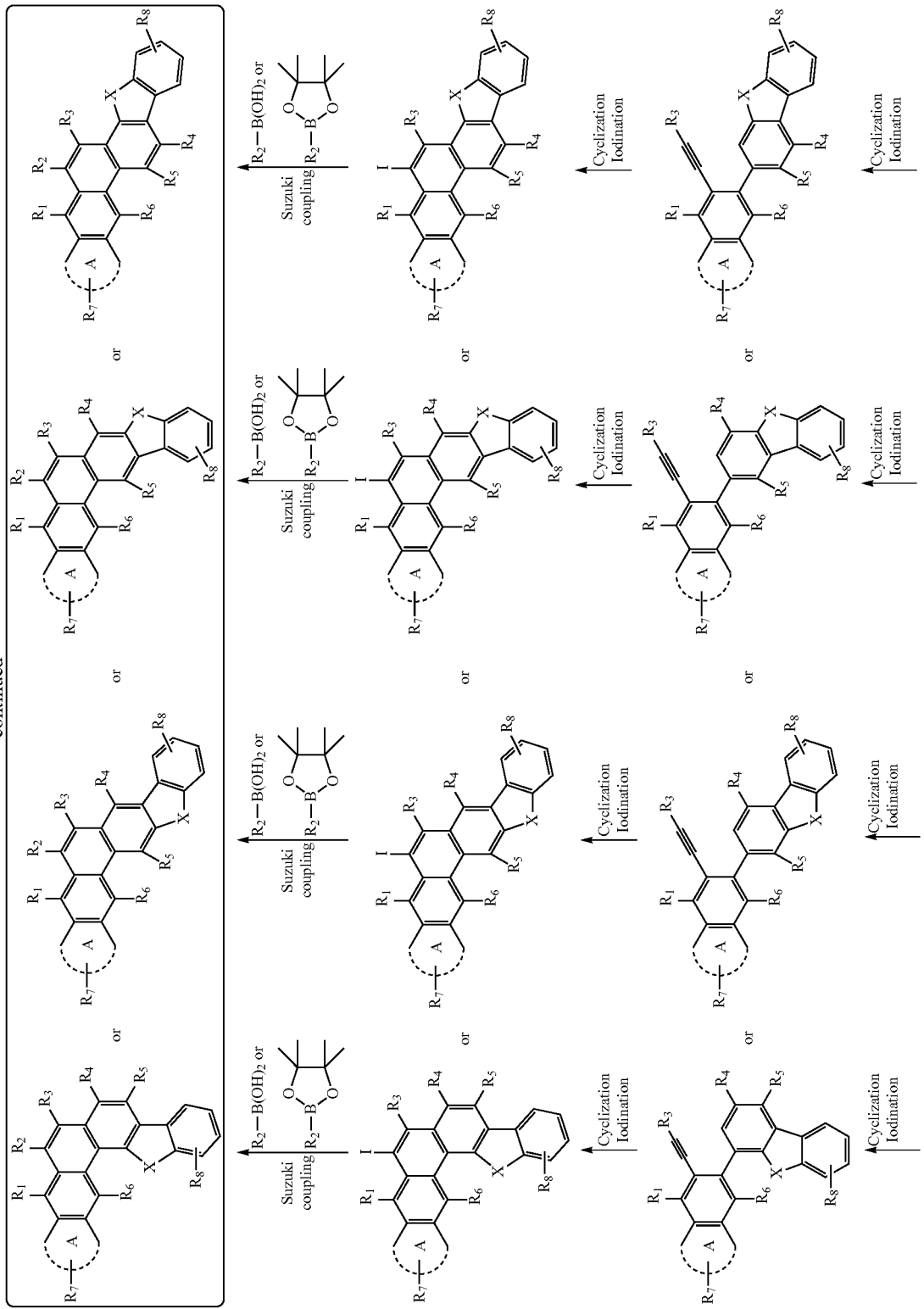

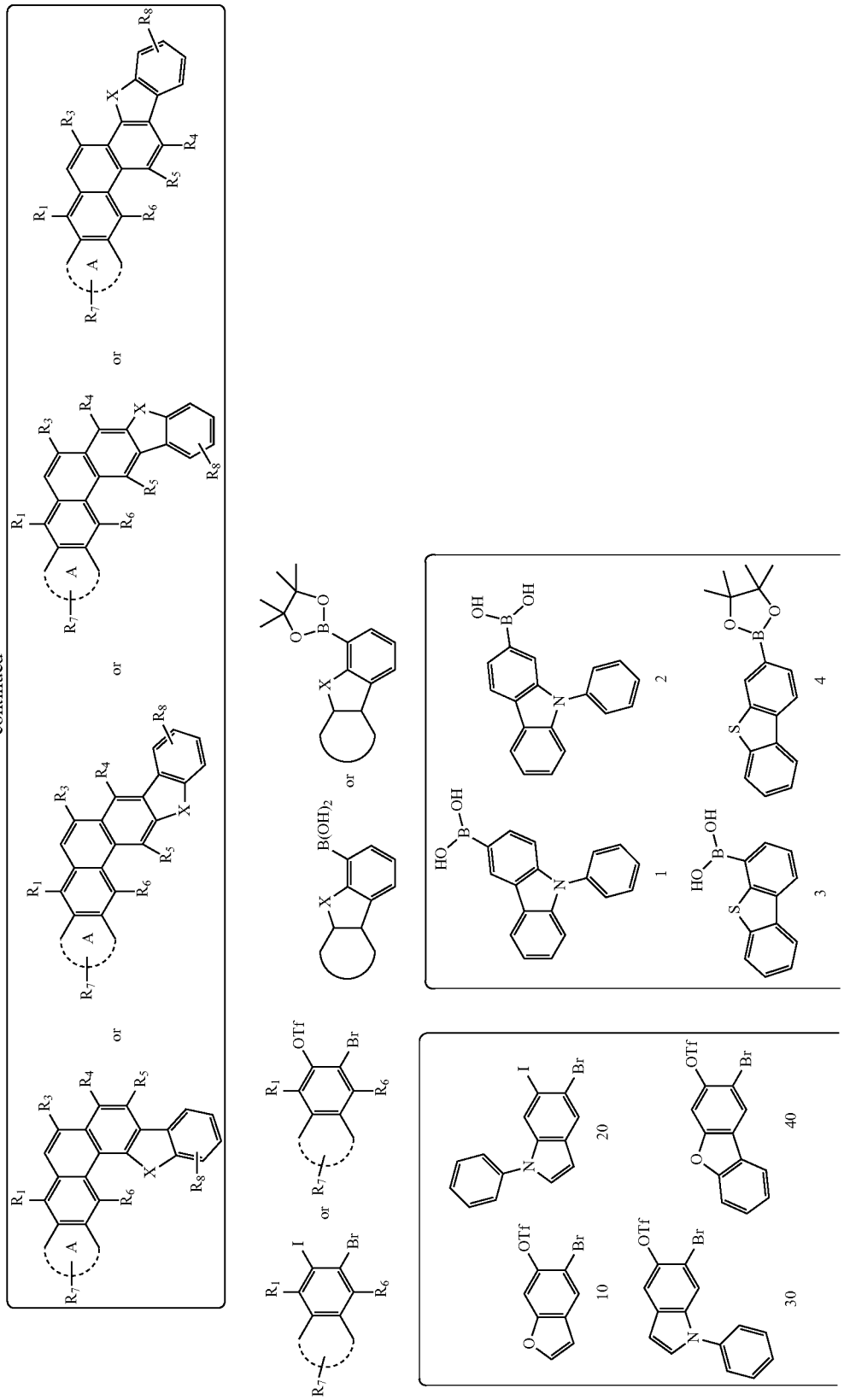

-continued
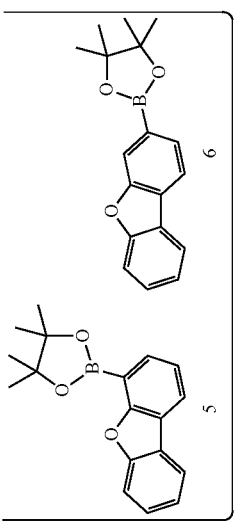
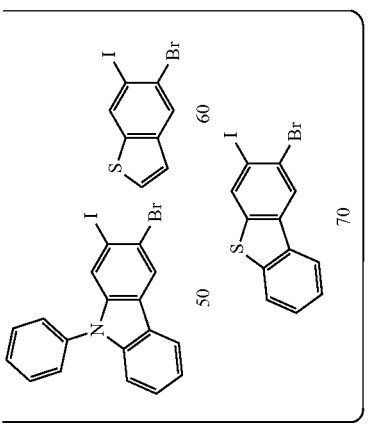
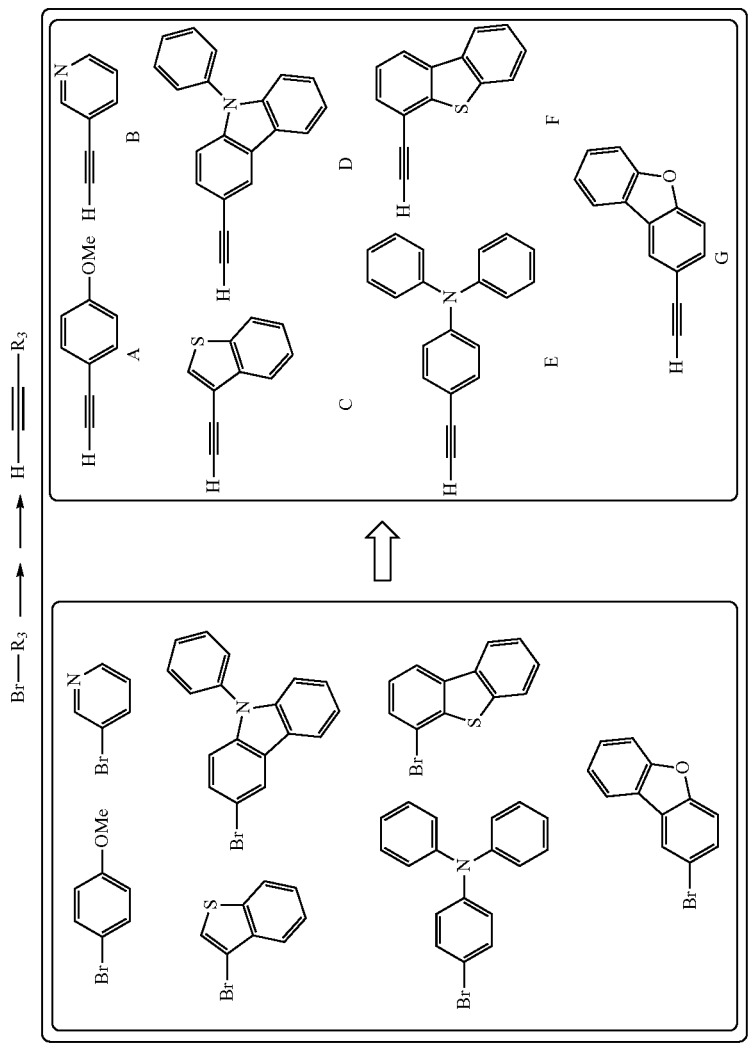

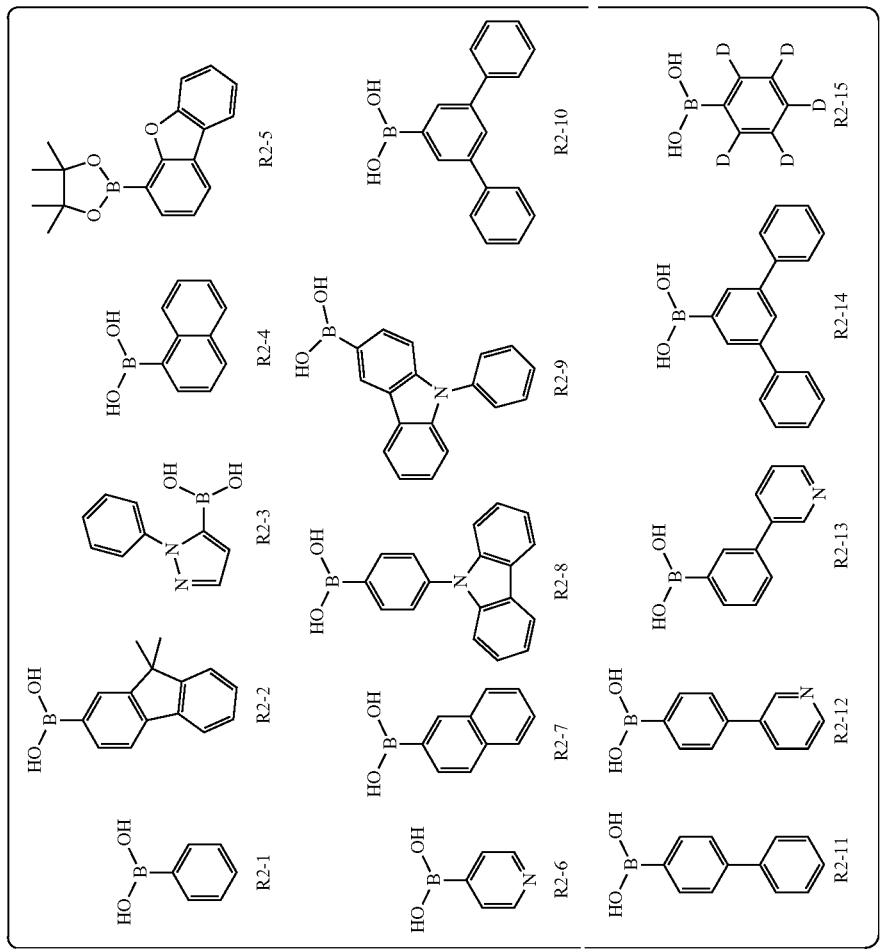

Representative Synthesis Example 1
Synthesis of Compounds 15-D
Compound 1 was synthesized according to Reaction Scheme 1 below.
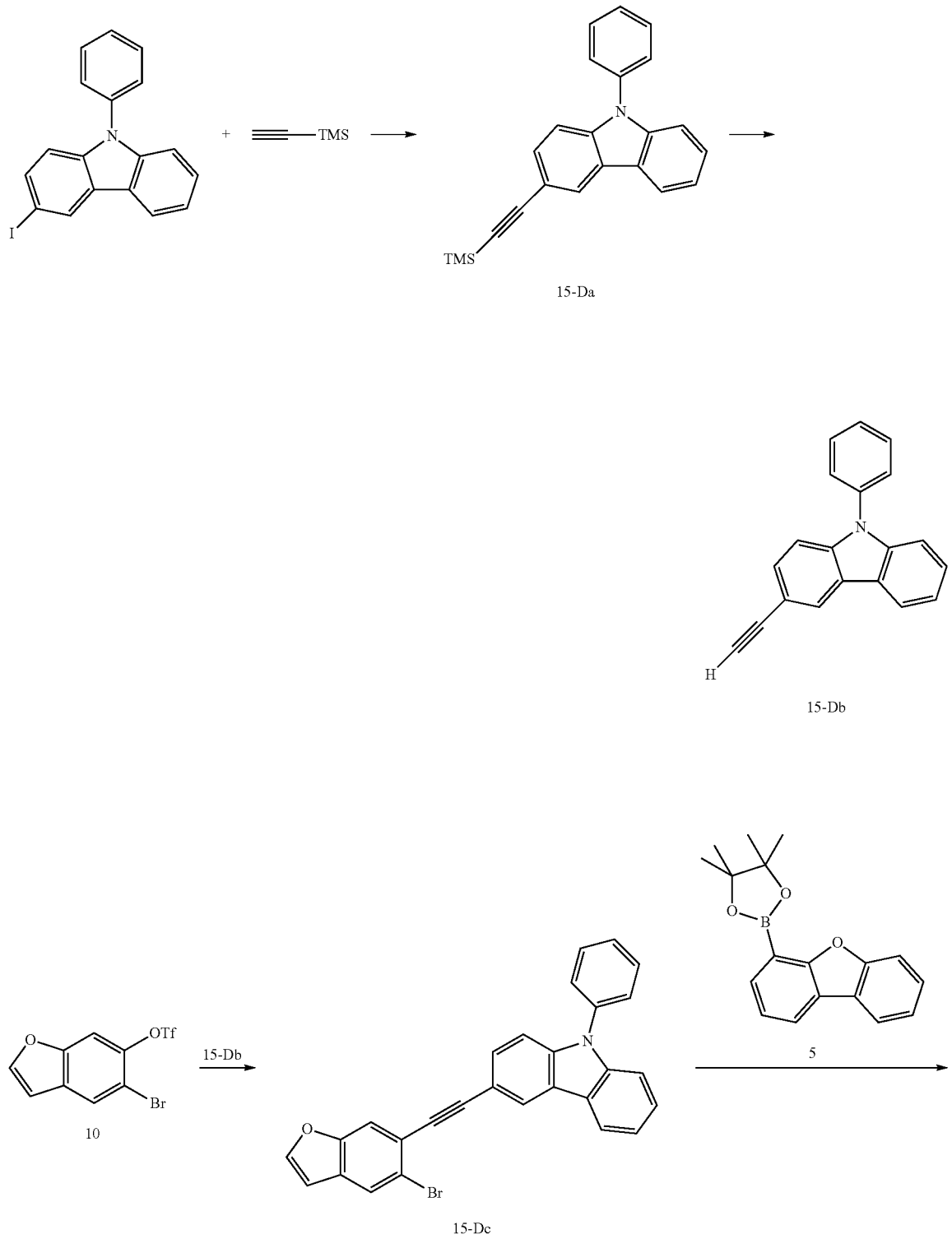

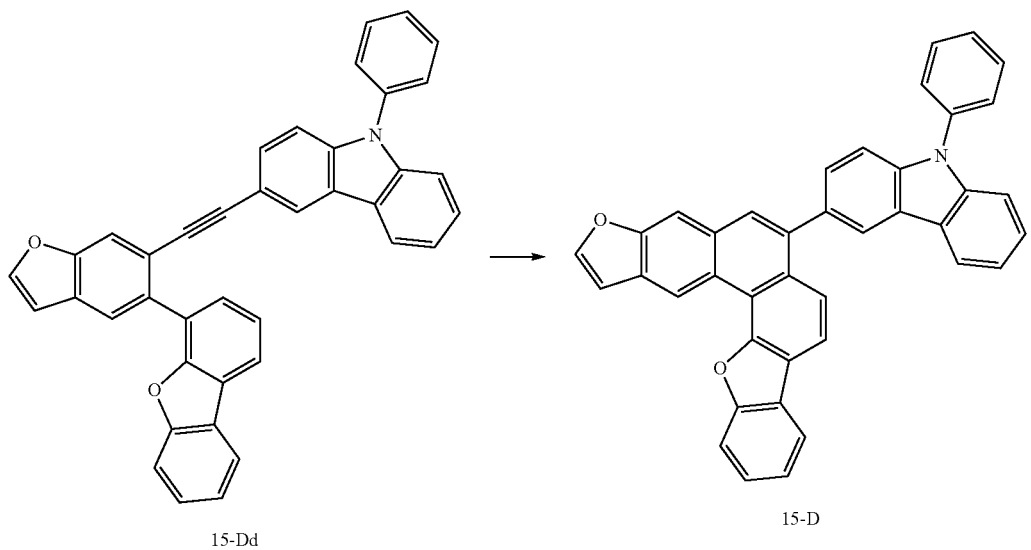

15-Dd                                                    15-D

Reaction Scheme 1: Synthesis of Intermediate 15-Da 22 g of 3-Iodo-9-phenyl-9H-carbazole, 2.8 g (0.04 eq) of Pd(PPh$_3$)$_4$, and 914 mg (0.08 eq) of CuI were put into a flask, which was then supplied with N$_2$ gas in a vacuum. After 200 mL of tetrahydrofuran (THF) was added into the flask and then stirred, 10 mL (1.2 eq) of triethylamine and 10.0 g (1.2 eq) of TMS-acetylene were slowly dropwise added thereinto and then stirred at room temperature for about 2 hours in a N$_2$ atmosphere. After removing the solvent using a rotary evaporator, the resulting reaction product was extracted two times each with 200 mL of Et$_2$O and 150 mL of water. The ether phase was collected and dried using magnesium sulfate, and the solvent was evaporated. The residue was separated and purified using silica gel column chromatography to obtain 20 g of Intermediate 15-Da with a yield of about 75%. This compound was identified using liquid chromatography-mass spectroscopy (LC-MS). C$_{23}$H$_{21}$N$_1$Si$_1$: M+339.14

Reaction Scheme 2: Synthesis of Intermediate 15-Db 4.2 g of Intermediate 15-Da was dissolved in 50 mL of THF, and 30 mL (3 eq) of tetrabutylammonium fluoride in THF (1.0M) was dropwise added thereinto and stirred for about 30 minutes. 50 mL of water was added to the solution. Then, the reaction solution was extracted three times each with 50 mL of ethylether. An organic layer was collected and dried using magnesium sulfate to evaporate the solvent. The residue was separated and purified using silica gel column chromatography to obtain 3.5 g of Intermediate 15-Db with a yield of about 95%. This compound was identified using LC-MS. C$_{20}$H$_{13}$N$_1$: M+267.10

Reaction Scheme 3: Synthesis of Intermediate 15-Dc 5.07 g (1.2 eq) of 5-bromo-6-iodo-benzofuran, 600 mg (0.04 eq) of Pd(PPh$_3$)$_4$, and 200 mg (0.08 eq) of CuI were put into a flask, which was then supplied with N$_2$ gas in a vacuum. After 50 mL of THF was added into the flask and then stirred, 2.2 mL (1.2 eq) of triethylamine and 3.5 g (1 eq) of Intermediate 15-Db were slowly dropwise added thereinto, and then stirred at room temperature for about 2 hours in a N$_2$ atmosphere. The solvent was removed by using a rotary evaporator. Then, 50 mL of water was added to the solution and the resulting reaction solution was extracted three times each with 50 mL of ethylether. An organic layer was collected and dried using magnesium sulfate to evaporate the solvent. The residue was separated and purified using silica gel column chromatography to obtain 3.45 g of Intermediate 15-Dc with a yield of about 57%. This compound was identified using LC-MS. C$_{23}$H$_{16}$Br$_1$N$_1$O$_1$: M+461.04

Reaction Scheme 4: Synthesis of Intermediate 15-Dd 3.28 g of Intermediate 15-Dc, 1.94 g (1.2 eq) of Compound 5, 410 mg (0.05 eq) of Pd(PPh$_3$)$_4$, and 4.9 g (5 eq) of K$_2$CO$_3$ were dissolved in 50 mL of THF and 15 mL of distilled water to obtain a mixed solution, which was then refluxed for about 24 hours while being stirred after a temperature increase to about 120° C. The reaction solution was cooled to room temperature, followed by extraction three times each with 100 mL of water and 100 mL of diethylether. The combined ether extracts were then dried using magnesium sulfate, and the solvent was evaporated. The residue was separated and purified using silica gel column chromatography to obtain 2.85 g of Intermediate 15-Dd with a yield of about 73%. This compound was identified using LC-MS. C$_{40}$H$_{23}$N$_1$O$_2$ M+549.17

Reaction Scheme 5: Synthesis of Compound 15-D 3.14 g of Intermediate 15-Dd was dissolved in 50 mL of methylene chloride (MC), and 8 mL (20 eq) of trifluoroacetic acid was dropwise added thereinto and stirred at room temperature for about 1 hour. After completion of the reaction, the reaction solution was extracted three times each with 100 mL of water and 100 mL of diethylether. The combined ether extracts were then dried using magnesium sulfate, and the solvent was evaporated. The residue was separately purified using silica gel column chromatography to obtain 2.86 g of Compound 15-D with a yield of about 91%. This compound was identified using LC-MS. C$_{40}$H$_{23}$N$_1$O$_2$: M+549.17

$^1$H NMR (CDCl$_3$, 400 MHz) δ (ppm) 8.93 (s, 1H), 8.12 (m, 2H), 7.93 (s, 1H), 7.82-7.77 (m, 2H), 7.55-7.00 (m, 16H), 6.66 (d, 1H)

Synthesis of Intermediates A, B, C, D, E, F, and G
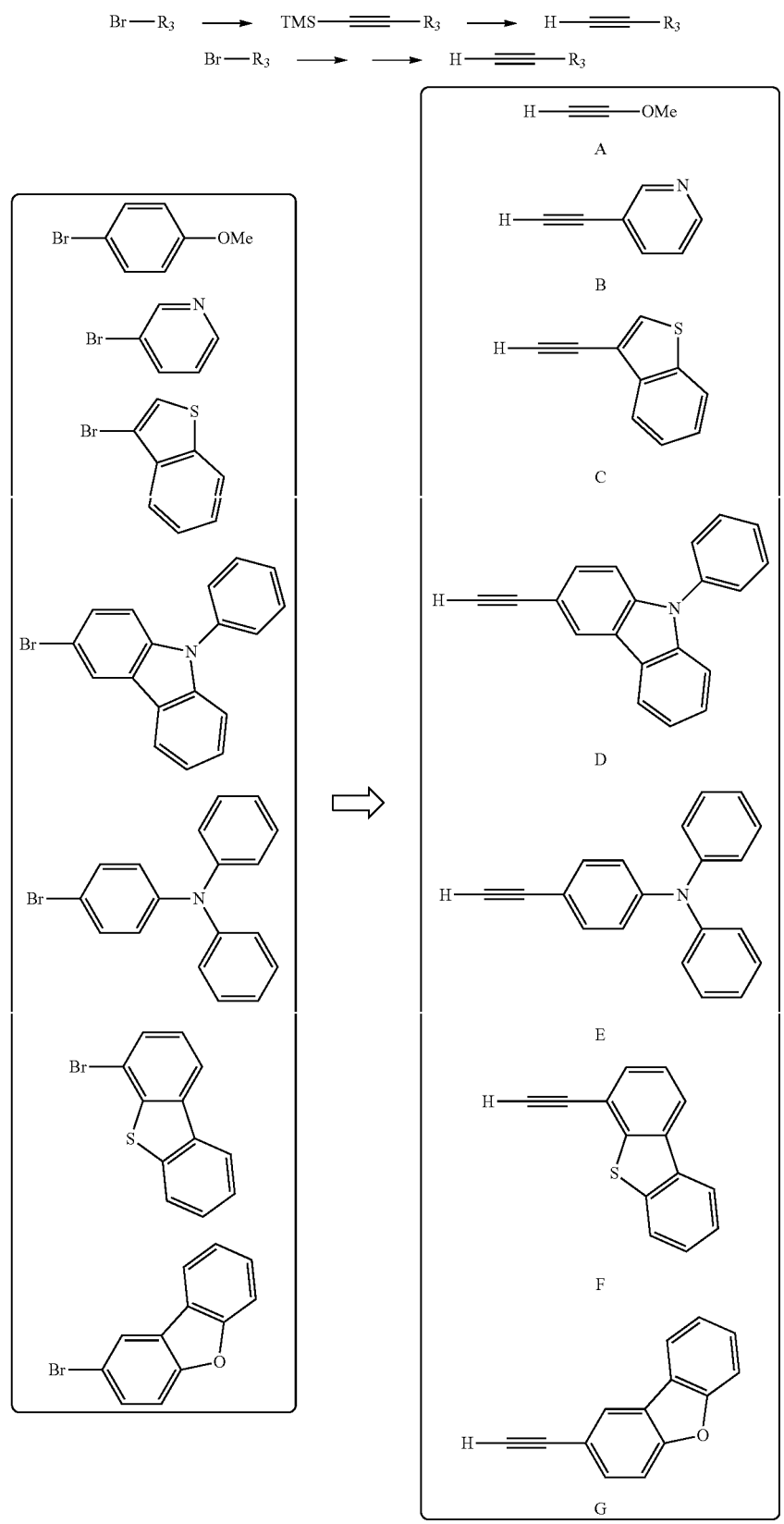

Intermediates A to G were synthesized in the same manner as in Reaction. Schemes 1 and 2 in Representative Synthesis Example 1 using the same equivalents of reactants.

| Intermediate | Yield Reaction Scheme 1 | Reaction Scheme 2 | LC-MS |
|---|---|---|---|
| A | 98 | 95 | 132.06 |
| B | 97 | 94 | 132.04 |
| C | 98 | 96 | 158.02 |
| D | 95 | 92 | 267.10 |
| E | 98 | 97 | 269.12 |
| F | 99 | 96 | 208.03 |
| G | 97 | 97 | 192.06 |

Synthesis of Compounds 11-A, 12-B, 13-D, 14-G, 15-F, 16-E, 21-B, 21-F, 22-C, 23-D, 24-E, 25-F, 26-G, 31-C, 32-D, 33-E, 34-F, 35-G, 36-A, 36-G, 41-D, 42-E, 43-D, 43-E, 44-G, 45-A, and 46-E A total of 17 compounds were synthesized in the same manner as in Reaction Schemes 3, 4 and 5 in Representative Synthesis Example 1 using the same equivalents of reactants.

| Compound | Yield Reaction Scheme 3 | Reaction Scheme 4 | Reaction Scheme 5 | LC-MS |
|---|---|---|---|---|
| 11-A | 58 | 78 | 89 | 489.17 |
| 12-B | 48 | 80 | 92 | 460.16 |
| 13-D | 62 | 69 | 93 | 565.15 |
| 14-G | 49 | 72 | 87 | 490.1 |
| 15-F | 51 | 73 | 91 | 490.1 |
| 16-E | 59 | 76 | 91 | 551.19 |
| 21-B | 45 | 77 | 87 | 535.2 |
| 21-F | 52 | 72 | 92 | 640.2 |
| 22-C | 50 | 74 | 96 | 590.18 |
| 23-D | 63 | 67 | 89 | 640.2 |
| 24-E | 61 | 71 | 94 | 642.21 |
| 25-F | 47 | 72 | 90 | 565.15 |
| 26-G | 52 | 66 | 87 | 549.17 |
| 31-C | 43 | 70 | 86 | 590.18 |
| 32-D | 57 | 74 | 91 | 699.27 |
| 33-E | 56 | 78 | 94 | 642.21 |
| 34-F | 53 | 76 | 90 | 581.13 |
| 35-G | 55 | 68 | 88 | 549.17 |
| 36-A | 65 | 66 | 91 | 489.17 |
| 36-G | 51 | 65 | 92 | 549.17 |
| 41-D | 61 | 82 | 87 | 674.24 |
| 42-E | 64 | 78 | 84 | 676.25 |
| 43-D | 67 | 74 | 89 | 615.17 |
| 43-E | 64 | 75 | 93 | 617.76 |
| 44-G | 52 | 69 | 93 | 540.12 |
| 45-A | 58 | 65 | 88 | 464.14 |
| 46-E | 57 | 80 | 87 | 601.2 |

$^1$H NMR (CDCl$_3$, 400 MHz) data

| Compound | NMR data |
|---|---|
| 11-A | 8.93 (s, 2H), 8.12 (s, 2H), 7.93 (s, 1H), 7.55-52 (t, 2H), 7.40-7.30 (m, 8H), 7.08-7.00 (m, 2H), 6.83 (d, 2H), 6.66 (d, 1H), 3.73 (s, 3H) |
| 12-B | 8.93 (s, 2H), 8.81 (s, 1H), 8.55 (d, 1H), 8.12 (d, 2H), 7.97-7.93 (t, 2H), 7.55-7.40 (m, 4H), 7.30 (m, 5H), 7.08-7.00 (m, 2H), 6.66 (s, 1H) |
| 13-D | 8.93 (s, 1H), 8.12 (s, 2H), 7.93-7.78 (m, 5H), 7.55-7.30 (m, 12H), 7.10-6.98 (m, 2H), 6.66 (d, 1H) |
| 14-G | 8.93 (s, 2H), 8.12 (s, 2H), 7.93-7.71 (m, 8H), 7.52-7.13 (m, 5H), 6.66 (d, 1H) |
| 15-F | 8.93 (s, 1H), 8.12 (s, 2H), 7.93-7.74 (m, 5H), 7.53-7.13 (m, 9H), 6.66 (d, 1H) |
| 16-E | 8.93 (s, 2H), 8.12 (s, 2H), 7.93 (s, 1H), 7.52-7.42 (m, 3H), 7.23-7.13 (m, 4H), 7.01 (m, 4H), 6.66-6.46 (m, 9H) |
| 21-B | 8.93 (s, 2H), 8.81 (s, 1H), 8.55 (d, 1H), 8.12 (s, 2H), 7.97 (s, 1H), 7.93 (s, 1H), 7.60-7.55 (m, 2H, 7.44-7.40 (m, 2H), 7.30 (m, 10H), 7.08-7.00 (m, 2H), 6.59 (d, 1H) |
| 21-F | 8.93 (s, 2H), 8.12 (s, 2H), 7.93 (s, 1H), 7.86 (s, 1H), 7.78-7.74 (m, 2H), 7.60-7.53 (m, 3H), 7.40-7.31 (m, 4H), 7.30 (m, 10H), 7.08-7.00 (m, 2H), 6.59 (d, 1H) |
| 22-C | 8.93 (s, 2H), 8.12 (s, 2H), 7.93-7.80 (m, 3H), 7.60-7.55 (m, 2H), 7.40-7.30 (m, 14H), 7.08-7.00 (m, 2H), 6.59 (d, 1H) |
| 23-D | 8.93 (s, 1H), 8.12 (s, 2H), 7.93-7.78 (m, 5H), 7.60-7.30 (m, 17H), 7.08-7.00 (m, 2H), 6.59 (m, 1H) |
| 24-E | 8.93 (s, 2H), 8.12 (s, 2H), 7.93-7.78 (m, 3H), 7.60 (d, 1H), 7.33-7.23 (m, 9H), 7.01 (t, 4H), 6.62-6.46 (m, 9H) |
| 25-F | 8.93 (s, 1H), 8.12 (s, 2H), 7.93.-7.74 (m, 5H), 7.60-7.13 (m, 14H), 6.59 (d, 1H) |
| 26-G | 8.93 (s, 2H), 8.12 (s, 2H), 7.93 (s, 1H), 7.71 (s, 1H), 7.60 (d, 1H), 7.49-7.42 (m, 6H), 7.30-7.13 (m, 9H), 6.59 (d, 1H) |
| 31-C | 8.93 (s, 2H), 8.12 (s, 2H), 7.93 (s, 1H), 7.90 (d, 1H), 7.80 (d, 1H), 7.60 (d, 1H), 7.55 (d, 1H), 7.40 (d, 2H), 7.32-7.28 (m, 12H), 7.08-7.00 (m, 2H), 6.59 (d, 1H) |
| 32-D | 8.93 (s, 2H), 8.12 (s, 2H), 7.93 (s, 1H), 7.77 (s, 1H), 7.60 (d, 1H), 7.55 (m, 2H), 7.46 (d, 1H), 7.40 (d, 2H), 7.33-7.27 (m, 16H), 7.08-7.00 (m, 4H), 6.59 (d, 1H) |
| 33-E | 8.93 (s, 1H), 8.12 (s, 2H), 7.93 (s, 1H), 7.86-7.78 (m, 3H), 7.60 (d, 1H), 7.31-7.33 (m, 2H), 7.30-7.23 (m, 7H), 7.01 (m, 4H), 6.62-6.49 (m, 9H) |
| 34-F | 8.93 (s, 2H), 8.12 (s, 2H), 7.93 (s, 1H), 7.86 (d, 2H), 7.78-7.74 (d, 3H), 7.60 (d, 1H), 7.53 (d, 1H), 7.39-7.30 (m, 10H), 6.59 (d, 1H) |
| 35-G | 8.93 (s, 1H), 8.12 (s, 2H), 7.93 (s, 1H), 7.82 (d, 1H), 7.71 (s, 1H), 7.60 (d, 1H), 7.49-7.41 (m, 6H), 7.30-7.13 (m, 9H), 6.59 (d, 1H) |
| 36-A | 8.93 (s, 2H), 8.12 (s, 2H), 7.93 (s, 1H), 7.60 (d, 1H), 7.49-7.37 (m, 4H), 7.30 (m, 5H), 7.19-7.13 (m, 2H), 6.83 (d, 2H), 6.59 (d, 1H), 3.73 (s, 3H) |
| 36-G | 8.93 (s, 2H), 8.12 (s, 2H), 7.93 (s, 1H), 7.71 (s, 1H), 7.60 (d, 1H), 7.49-7.42 (m, 6H), 7.30-7.13 (m, 9H), 6.59 (d, 1H) |
| 41-D | 8.93 (s, 2H), 8.12 (s, 2H), 7.93 (s, 1H), 7.77 (s, 1H), 7.55-7.00 (m, 24H) |

-continued

| Compound | NMR data |
|---|---|
| 42-E | 8.93 (s, 2H), 8.12 (s, 2H), 7.93 (s, 1H), 7.55-7.40 (m, 4H), 7.30-7.00 (m, 15H), 6.62-6.46 (m, 8H) |
| 43-D | 8.93 (s, 1H), 8.12 (s, 2H), 7.93-7.77 (m, 5H), 7.55-7.00 (m, 17H)) |
| 43-E | 8.93 (s, 1H), 8.12 (s, 2H), 7.93-7.77 (m, 4H), 7.49-7.31 (m, 4H), 7.23-7.13 (m, 4H), 7.01 (t, 4H), 6.62 (t, 2H), 6.52 (d, 2H), 6.46 (d, 4H) |
| 44-G | 8.93 (s, 2H), 8.12 (s, 2H), 7.93 (s, 1H), 7.86 (d, 1H), 7.78 (d, 1H), 7.71 (s, 1H), 7.49-7.31 (m, 8H), 7.19 (t, 2H), 7.13 (m, 2H) |
| 45-A | 8.93 (s, 1H), 8.12 (s, 2H), 7.93 (s, 1H), 7.82 (d, 1H), 7.49-7.37 (m, 6H), 7.19-7.13 (m, 4H), 6.83 (d, 2H), 3.73 (s, 3H) |
| 46-E | 8.93 (s, 2H), 8.12 (s, 2H), 7.93 (s, 1H), 749-7.42 (m, 4H), 7.23-7.01 (m, 10H), 6.62-6.46 (m, 8H) |

Representative Synthesis Example 2

Synthesis of Compound 16-H

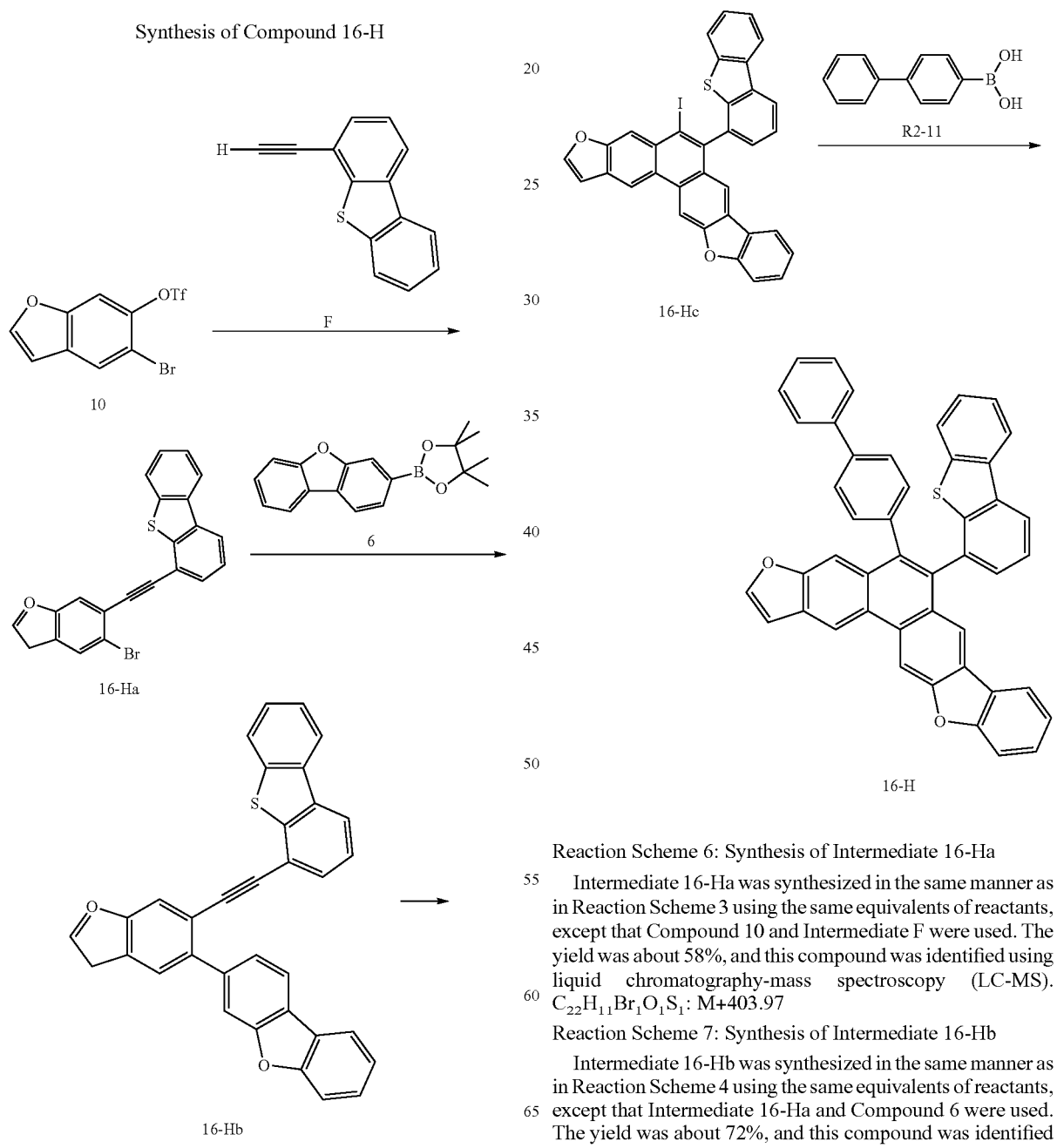

16-H

Reaction Scheme 6: Synthesis of Intermediate 16-Ha

Intermediate 16-Ha was synthesized in the same manner as in Reaction Scheme 3 using the same equivalents of reactants, except that Compound 10 and Intermediate F were used. The yield was about 58%, and this compound was identified using liquid chromatography-mass spectroscopy (LC-MS). $C_{22}H_{11}Br_1O_1S_1$: M+403.97

Reaction Scheme 7: Synthesis of Intermediate 16-Hb

Intermediate 16-Hb was synthesized in the same manner as in Reaction Scheme 4 using the same equivalents of reactants, except that Intermediate 16-Ha and Compound 6 were used. The yield was about 72%, and this compound was identified using LC-MS. $C_{34}H_{18}O_2S_1$: M+490.10

187

Reaction Scheme 8: Synthesis of Intermediate 16-Hc 7.9 g (2 eq) of bis(pyridine)iodonium tetrafluoroborate and 80 ml of dichloromethane were mixed together, and 3.11 mL (0.002 eq, d 1.696) of $CF_3SO_3H$ was added thereto and stirred at about −40° C. After a mixture of 20 ml of dichloromethane and 3 g (1 eq) of Intermediate 16-Hb was added to the reaction solution, the temperature was increased to about 10° C., and then stirred for about 2 hours. After the temperature of the reaction solution was increased to room temperature, the organic phase mixture was washed three times with 100 mL of water. The organic residue was extracted with 100 mL of diethyl ether three times. The combined ether phases were then dried using magnesium sulfate, and the solvent was evaporated. The residue was separated and purified by silica gel column chromatography to obtain 3.62 g of Intermediate 16-Hc with a yield of about 96%. This compound was identified using LC-MS. $C_{34}H_{17}I_1O_2S_1$: M+616.00

Reaction Scheme 9: Synthesis of Compound 16-H 3.0 g of Intermediate 16-Hc, 1.5 g (1.5 eq) of Compound R2-11, 281 mg (0.05 eq) of $Pd(PPh_3)_4$, and 3.36 g (5 eq) of $K_2CO_3$ were mixed with 100 mL of THF and 30 mL of distilled water to obtain a mixture, which was then refluxed for about 24 hours while being stirred after a temperature increase to about 120° C. The resulting reaction solution was cooled to room temperature, followed by extraction three times each with 100 mL of water and 100 mL of diethylether. The combined ether phases were dried using magnesium sulfate and the solvent was evaporated. The residue was separated and purified by silica gel column chromatography to obtain 2.25 g (72% Yield) of Compound 16-H. This compound was identified using LC-MS and nuclear magnetic resonance (NMR). $C_{46}H_{26}O_2S_1$: M+642.17

A peak is detected at a chemical shift of 9.15±0.5 (s, 1H), 8.30±0.5 (d, 2H), 7.92±0.5 (s, 1H), 7.75±0.5 (m, 3H), and 7.62±0.5 (m, 3H) using $^1$H-NMR operating at 400 MHz.

Synthesis of Compound 23-H

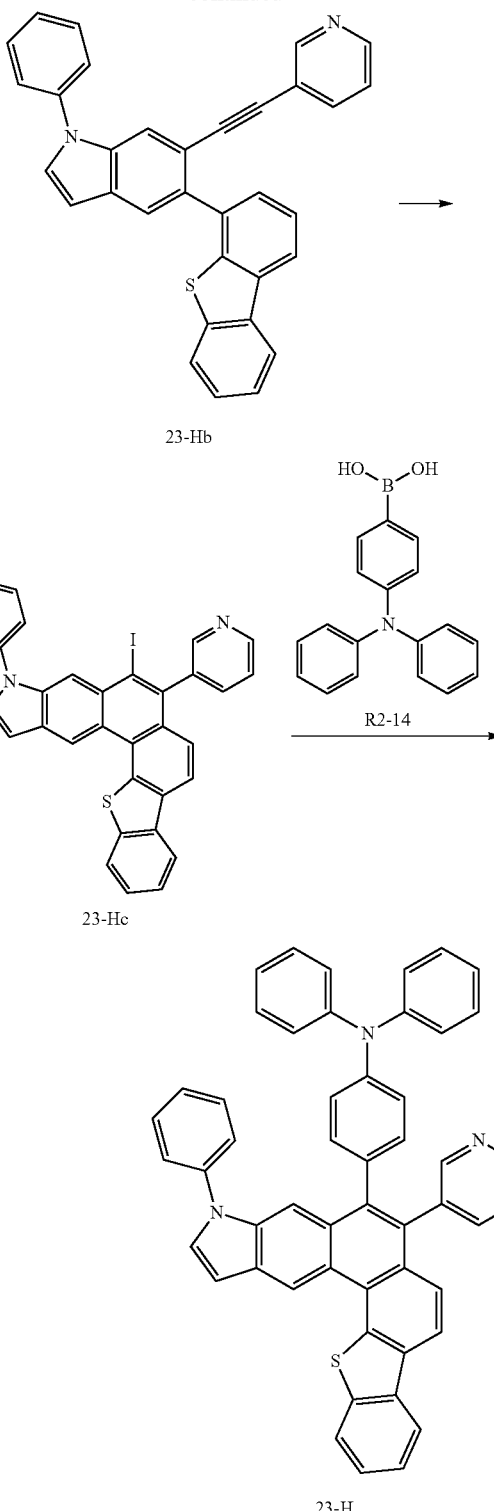

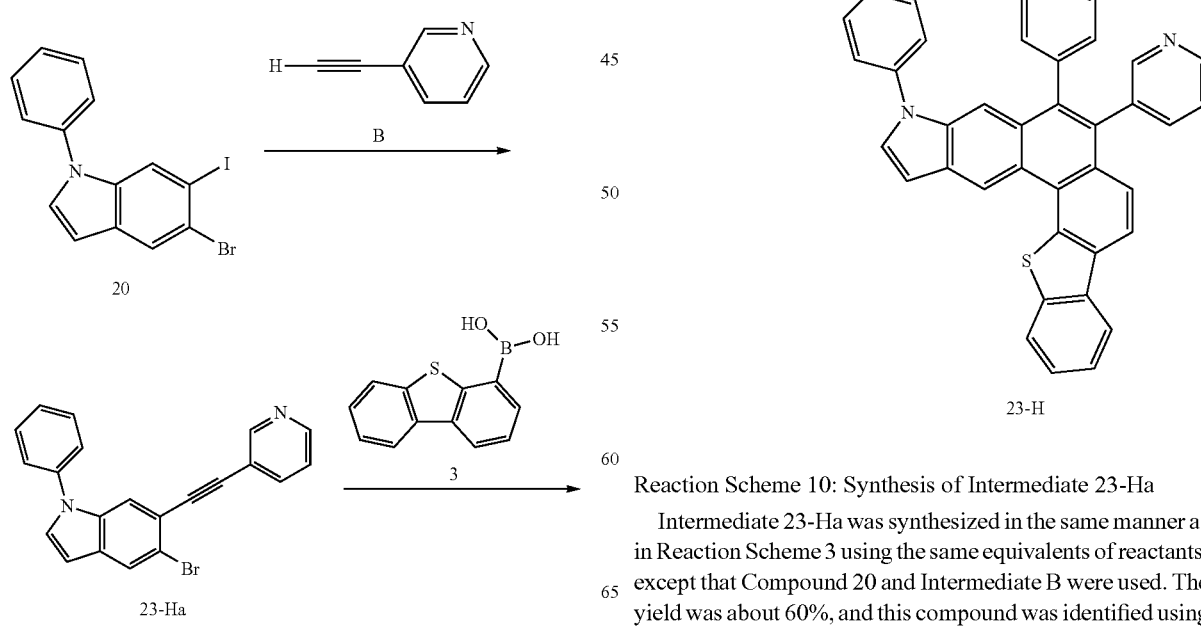

Reaction Scheme 10: Synthesis of Intermediate 23-Ha

Intermediate 23-Ha was synthesized in the same manner as in Reaction Scheme 3 using the same equivalents of reactants, except that Compound 20 and Intermediate B were used. The yield was about 60%, and this compound was identified using LC-MS. $C_{21}H_{13}Br_1N_2$: M+372.03

Reaction Scheme 11: Synthesis of Intermediate 23-Hb

Intermediate 23-Hb was synthesized in the same manner as in Reaction Scheme 4 using the same equivalents of reactants, except that Intermediate 23-Ha and Compound 3 were used. The yield was about 70%, and this compound was identified using LC-MS. $C_{33}H_{20}N_2S_1$: M+476.13

Reaction Scheme 12: Synthesis of Intermediate 23-Hc

Intermediate 23-Ha was synthesized in the same manner as in Reaction Scheme 8 using the same equivalents of reactants, except that Intermediate 23-Hb was used. The yield was about 93%, and this compound was identified using LC-MS. $C_{33}H_{19}I_1N_2S_1$: M+602.03

Reaction Scheme 13: Synthesis of Compound 23-H

Intermediate 23-H was synthesized in the same manner as in Reaction Scheme 9 using the same equivalents of reactants, except that 3.0 g of Intermediate 23-Hc and compound R12-14 were used. The yield was about 68%, and this compound was identified using LC-MS and NMR. $C_{51}H_{33}N_3S_1$: M+719.24

$^1$H NMR (CDCl$_3$, 400 MHz) δ (ppm) 8.93 (s, 1H), 8.81 (s, 1H), 8.55 (d, 1H), 8.12 (s, 2H), 7.97 (d, 1H), 7.86-7.78 (m, 3H), 7.60 (d, 1H), 7.44 (t, 1H), 7.33-7.31 (m, 2H), 7.30-7.23 (m, 7H), 7.01 (t, 4H), 6.62-6.46 (m, 9H)

Example 1

To manufacture an anode, a corning 15 Ω/cm² (1200 Å) ITO glass substrate was cut to a size of 50 mm×50 mm×0.7 mm, then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 4,4',4"-tris(N-(2-naphthyl)-N-phenylamino)triphenylamine (2-TNATA), which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

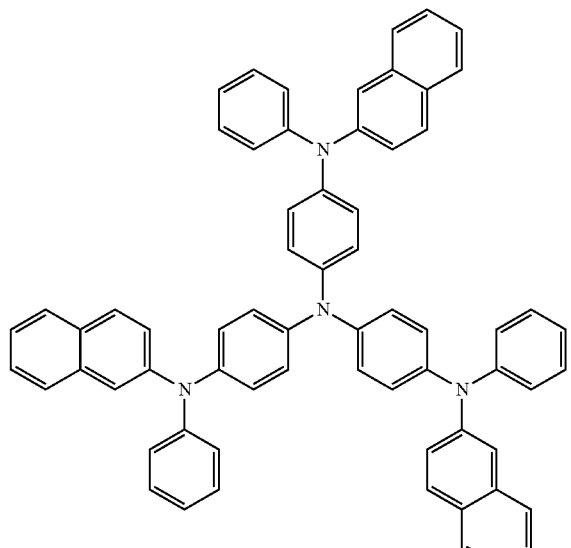

2-TNATA

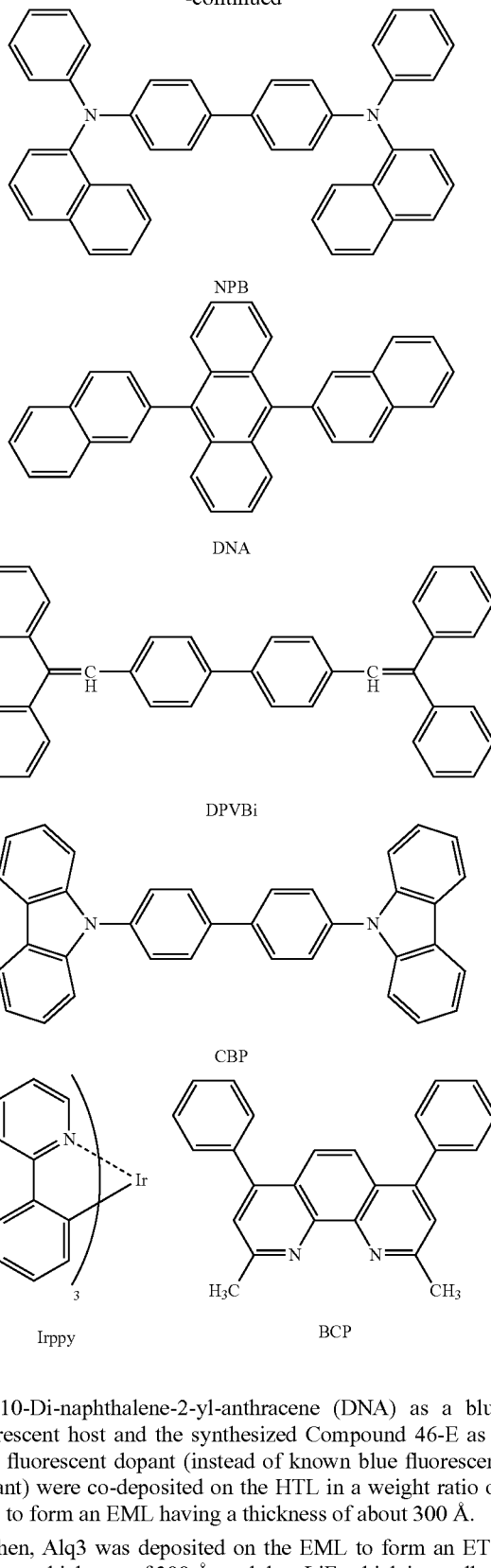

9,10-Di-naphthalene-2-yl-anthracene (DNA) as a blue fluorescent host and the synthesized Compound 46-E as a blue fluorescent dopant (instead of known blue fluorescent dopant) were co-deposited on the HTL in a weight ratio of 98:2 to form an EML having a thickness of about 300 Å.

Then, Alq3 was deposited on the EML to form an ETL having a thickness of 300 Å, and then LiF, which is an alkali metal halide, was deposited on the ETL to form an EIL having a thickness of 10 Å. Then, aluminum was vacuum-deposited on the EIL to form a cathode having a thickness of 3000 Å, thereby forming a LiF/Al electrode and completing the manufacture of an organic light-emitting device.

The organic light-emitting device thus formed had a driving voltage of about 6.21 V at a current density of 50 mA/cm$^2$, a luminosity of 2,280 cd/m$^2$, a luminescent efficiency of 4.68 cd/A, and a half life-span (hr@100 mA/cm$^2$) of about 32 hours.

Example 2

An organic light-emitting device was manufactured in the same manner as in Example 1, except that the synthesized Compound 15-D, instead of NPB, was used to form the HTL, and the blue fluorescent host 9,10-di-naphthalene-2-yl-anthracene (DNA) and the blue fluorescent dopant 4,4'-bis(2,2-diphenylvinyl)biphenyl (DPVBi) were used to form the EML.

Example 3

An organic light-emitting device was manufactured in the same manner as in Example 1, except that the synthesized Compound 23-H, instead of NPB, was used to form the HTL, and the blue fluorescent host 9,10-di-naphthalene-2-yl-anthracene (DNA) and the blue fluorescent dopant DPVBi were used to form the EML.

Example 4

An organic light-emitting device was manufactured in the same manner as in Example 1, except that the synthesized Compound 43-E, instead of NPB, was used to form the HTL, and the blue fluorescent host 9,10-di-naphthalene-2-yl-anthracene (DNA) and the blue fluorescent dopant DPVBi were used to form the EML.

Example 5

An organic light-emitting device was manufactured in the same manner as in Example 1, except that the synthesized Compound 15-F, instead of known compound CBP, as a green phosphorescent host, and a known compound, tris(2-phenylpyridine)iridium (Irppy), as a green phosphorescent dopant were co-deposited in a weight ratio of 91:9 to form an EML having a thickness of about 300 Å. BCP, which functions as a hole blocking compound, was then vacuum-deposited on the EML to form a HBL having a thickness of about 50 Å.

Example 6

An organic light-emitting device was manufactured in the same manner as in Example 5, except that the synthesized Compound 32-D, instead of compound CBP, was used as a green phosphorescent host to form the EML.

Example 7

An organic light-emitting device was manufactured in the same manner as in Example 5, except that the synthesized Compound 43-D, instead of compound CBP was used as a green phosphorescent host to form the EML.

Comparative Example 1

An organic light-emitting device was manufactured in the same manner as in Example 1, except that blue fluorescent dopant DPVBi, instead of Compound 46-E, was used to form the EML.

Comparative Example 2

An organic light-emitting device was manufactured in the same manner as in Example 5, except that green phosphorescent host CBP, instead of Compound 15-F, was used to form the EML.

The characteristics and lifetimes of the organic light-emitting devices of Examples 1-7 and Comparative Examples 1-2 are shown in Table 1 below.

TABLE 1

| | Dopant, host or Hole transport | Driving voltage (V) | Current density (mA/cm$^2$) | Luminance (cd/cm$^2$) | Efficiency (cd/A) | Emission color | Half-life span (hr @100 mA/cm$^2$) |
|---|---|---|---|---|---|---|---|
| Example 1 | Blue fluorescent dopant 46-E | 6.21 | 50 | 2,280 | 4.68 | blue | 32 |
| Example 2 | Hole transport 15-D | 6.18 | 50 | 2,183 | 4.37 | blue | 29 |
| Example 3 | Hole transport 23-H | 6.03 | 50 | 2,309 | 4.62 | blue | 27 |
| Example 4 | Hole transport 43-e | 6.32 | 50 | 2,366 | 4.73 | blue | 30 |
| Example 5 | Green phosphorescent host 15-F | 5.67 | 50 | 16,654 | 33.3 | green | 84 |
| Example 6 | Green phosphorescent host 32-d | 5.33 | 50 | 17,102 | 34.2 | green | 91 |
| Example 7 | Green phosphorescent host 43-d | 5.51 | 50 | 18,248 | 36.5 | green | 93 |
| Comparative Example 1 | DNA/DPBVi | 7.35 | 50 | 1,522 | 3.04 | blue | 15 |
| Comparative Example 2 | CBP/Irppy | 6.8 | 50 | 10,902 | 21.8 | green | 60 |

The organic light-emitting devices manufactured according to embodiments of the invention, each using the compounds represented by Formula 1 as a blue fluorescent dopant, a green phosphorescent host, or an ETL material, had lower driving voltages by about 1.0 V, improved I-V-L characteristics with much higher efficiencies, and remarkable improvements in luminance and lifetime, as compared to those manufactured using DPVBi and CBP. The organic light-emitting device of Example 1, which was manufactured using Compound 46-E as a blue fluorescent dopant, was found to have improvements in driving voltage, efficiency and lifetime when compared with Comparative Example 1. The organic light-emitting devices of Examples 2-4, which were manufactured using Compounds 15-D, 23-H, and 43-H, respectively, as the hole transport host, were found to show improvements in driving voltage, efficiency and lifetime, as compared with Comparative Example 1. The organic light-emitting devices of Examples 5-7, which were manufactured using Compounds 15-F, 32-D, and 43-D, respectively as the green phosphorescent host, were found to show improvements in driving voltage, efficiency, and lifetime, as compared with Comparative Example 2.

The heterocyclic compounds of Formula 1, described above, can each be used as a blue fluorescent dopant or a green phosphorescent host with high light-emission characteristics. Accordingly, organic light-emitting devices having high efficiency, low driving voltages, high luminance and long lifetime can be manufactured using the heterocyclic compounds of Formula 1 above.

While the present invention has been particularly shown and described with reference to exemplary embodiments thereof, it will be understood by those of ordinary skill in the art that various changes in form and details can be made therein without departing from the spirit and scope of the present invention as defined by the following claims.

What is claimed is:

1. A heterocyclic compound represented by one of Formulae 1 to 4 below:

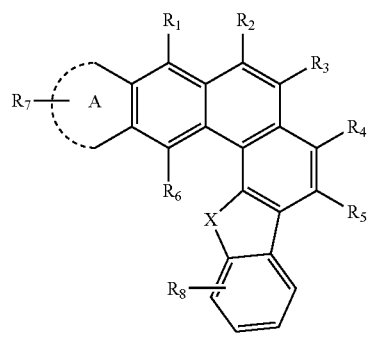

Formula 1

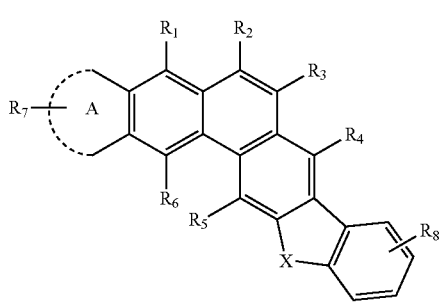

Formula 2

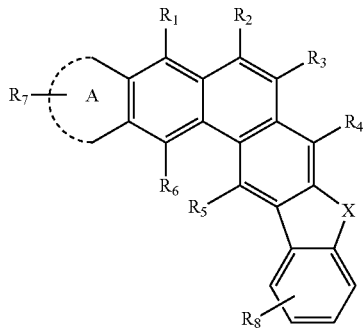

Formula 3

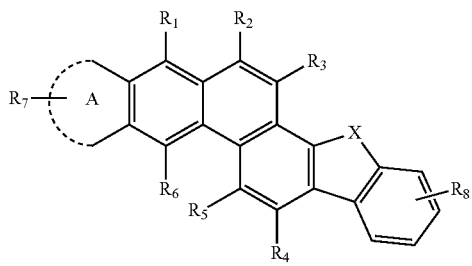

Formula 4

$R_1$ to $R_8$ in Formula 1 being each independently selected from a hydrogen atom, a deuterium atom, a halogen atom, a cyano group, a substituted or unsubstituted $C_1$-$C_{60}$ alkyl group, a substituted or unsubstituted $C_6$-$C_{60}$ aryl group, a substituted or unsubstituted $C_3$-$C_{60}$ heteroaryl group, and a substituted or unsubstituted $C_6$-$C_{60}$ condensed polycyclic group;

X is —O—, —S—, or —$NR_{20}$—; and $R_{20}$ is selected from a substituted or unsubstituted $C_1$-$C_{30}$ alkyl group and a substituted or unsubstituted $C_6$-$C_{30}$ aryl group; and A is a moiety selected from a substituted or unsubstituted furan group, a substituted or unsubstituted thiophene group, a substituted or unsubstituted pyrrole group, a substituted or unsubstituted benzofuran group, a substituted or unsubstituted benzothiophene group, and a substituted or unsubstituted benzopyrrole group, said moiety being fused to the skeleton of one of Formulae 1 to 4.

2. The heterocyclic compound of claim 1, comprised of $R_1$, $R_4$, $R_6$ and $R_8$ being each independently selected from a hydrogen atom and a deuterium atom.

3. The heterocyclic compound of claim 1, comprised of said moiety being fused at positions 2 and 3 in moiety Formula 11 below, or positions 2 and 3 in moiety Formula 12 below:

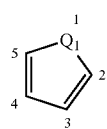

Formula 11

Formula 12

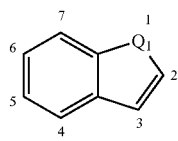

Q₁ being —O—, —NR₃₀—, or —S— in Formulae 11 and 12, R₃₀ being selected from a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, and a substituted or unsubstituted $C_6$-$C_{20}$ condensed polycyclic group.

4. The heterocyclic compound of claim 1, comprised of A in Formulae 1 to 4 indicating that a substituted or unsubstituted furan group, a substituted or unsubstituted benzofuran group, or a substituted or unsubstituted pyrrole group is fused to the skeleton of Formula 1, 2, 3, or 4.

5. The heterocyclic compound of claim 3, comprised of A in Formulae 1 to 4 being selected from a substituted or unsubstituted furan group, a substituted or unsubstituted benzofuran group, and a substituted or unsubstituted pyrrole group, Q₁ in Formulae 11 and 12 being selected from —O— and —NR₃₀—.

6. The heterocyclic compound of claim 1, R₂ and R₃ in Formulae 1 to 4 each independently being selected from one of the groups represented by Formulae 2a to 2f below:

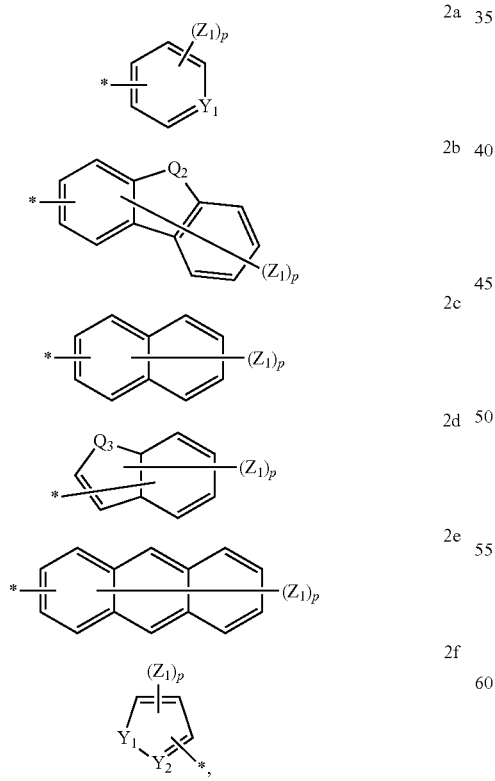

Q₂ in Formulae 2a to 2f being a linking group selected from —N(R₃₀)—, —CR₃₁R₃₂—, —S—, and —O—;

Q₃ is a linking group selected from —S— and —O—;

Y₁ and Y₂ are each independently selected from —N=, —N(R₃₀)—, and —CH=;

Z₁, R₃₀, R₃₁, and R₃₂ are each independently selected from a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group or a $C_3$-$C_{20}$ heteroaryl group, a halogen group, a cyano group, a nitro group, a hydroxyl group, and a carboxy group;

p is an integer from 1 to 9; and

* indicates a binding site.

7. The heterocyclic compound of claim 1, comprised of the compounds of Formulae 1 to 4 being selected from the compounds represented by the following formulae:

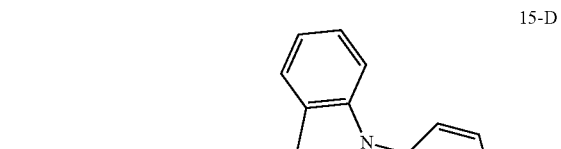

15-D

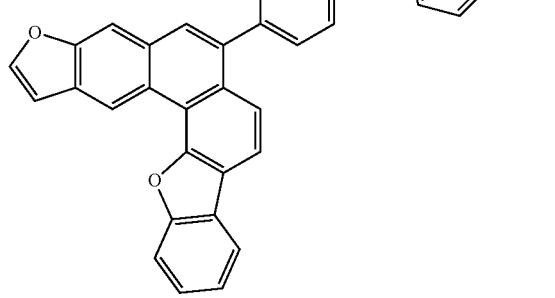

15-F

-continued

23-H
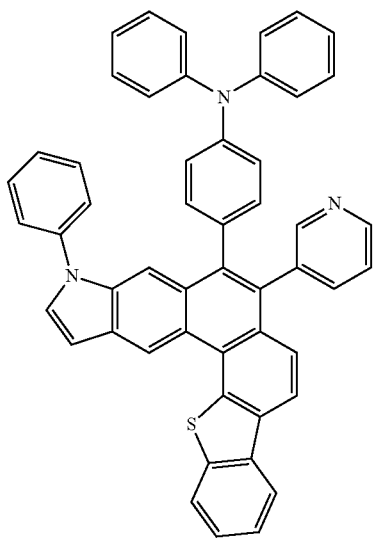

32-D
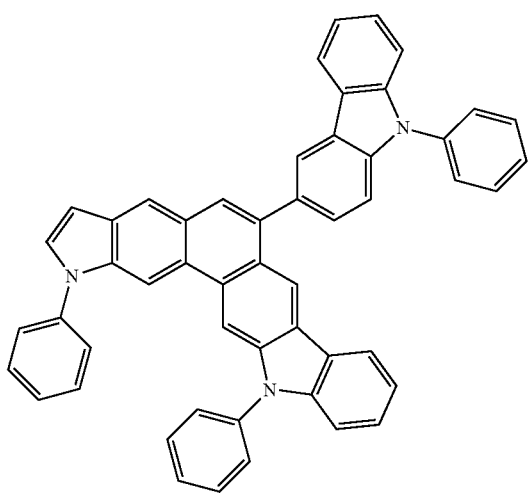

43-D
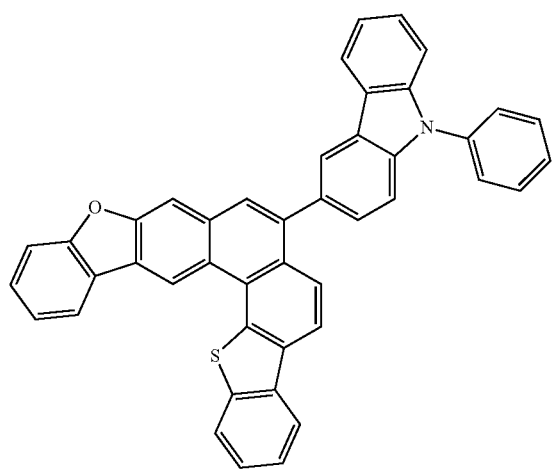

-continued

43-E
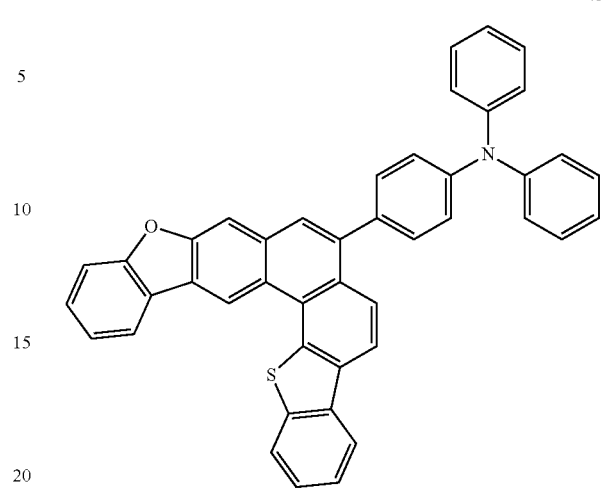

46-E
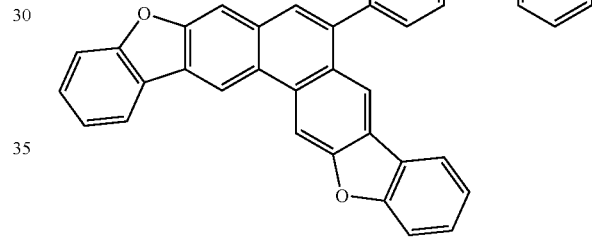

8. An organic light-emitting device comprising:
a first electrode;
a second electrode; and
an organic layer between the first electrode and the second electrode, the organic layer comprising a heterocyclic compound according to claim 1.

9. The organic light-emitting device of claim 8, comprised of the organic layer being an emission layer and the heterocyclic compound being used as a fluorescent dopant.

10. The organic light-emitting device of claim 8, comprised of the organic layer comprising an emission layer, the heterocyclic compound being used as a phosphorescent host.

11. The organic light-emitting device of claim 8, comprised of the organic layer being selected from a blue emission layer and a green emission layer.

12. The organic light-emitting device of claim 8, comprised of:
the organic layer comprising one of an emission layer, a hole injection layer, a hole transport layer, and a functional layer having both hole injection and hole transport capabilities;
at least one of the hole injection layer, the hole transport layer, and the functional layer having both hole injection and hole transport capabilities and further comprising the heterocyclic compound of one of Formulae 1 to 4; and
the emission layer comprising an anthracene compound, an arylamine compound, or a styryl compound.

13. The organic light-emitting device of claim 8, comprised of:
the organic layer comprising an emission layer, a hole injection layer, a hole transport layer, or a functional layer having both hole injection and hole transport capabilities;
at least one of the hole injection layer, the hole transport layer, and the functional layer having both hole injection and hole transport capabilities and further comprising a heterocyclic compound of one of Formulae 1 to 4; and
the emission layer comprising red, green, blue, and white emission layers, one of said emission layers comprising a phosphorescent compound.

14. The organic light-emitting device of claim 13, comprised of at least one of the hole injection layer, the hole transport layer, and the functional layer further comprising a charge-generating material.

15. The organic light-emitting device of claim 14, comprised of the charge-generating material being a p-dopant, the p-dopant being selected from a quinine derivative, a metal oxide, and a cyano group-containing compound.

16. The organic light-emitting device of claim 8, comprised of the organic layer further comprising an electron transport layer, the electron transport layer comprising an electron transporting organic compound and a metal complex.

17. The organic light-emitting device of claim 16, comprised of the metal complex being lithium quinolate (LiQ).

18. The organic light-emitting device of claim 16, comprised of the metal complex being Compound 203 below:

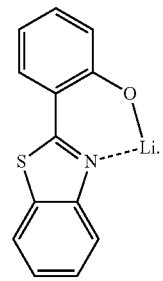

<203>

19. The organic light-emitting device of claim 8, comprised of the organic layer being formed from the heterocyclic compound of one of Formulae 1 to 4 using a wet process.

20. A flat panel display device comprising the organic light-emitting device of claim 8, and the first electrode of the organic light-emitting device being electrically connected to a source electrode of a thin-film transistor or a drain electrode of a thin-film transistor.

* * * * *